(12) United States Patent
Guzman et al.

(10) Patent No.: US 9,962,707 B2
(45) Date of Patent: *May 8, 2018

(54) PIPETTING DEVICE, PIPETTE TIP COUPLER, AND PIPETTE TIP: DEVICES AND METHODS

(71) Applicant: Hamilton Company, Reno, NV (US)

(72) Inventors: Jose Eduardo Guzman, Sparks, NV (US); Thomas Barresi, Reno, NV (US); Dana A. Belton, Sparks, NV (US)

(73) Assignee: Hamilton Company, Reno, NV (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/838,759

(22) Filed: Dec. 12, 2017

(65) Prior Publication Data

US 2018/0099284 A1 Apr. 12, 2018

Related U.S. Application Data

(63) Continuation of application No. 15/348,298, filed on Nov. 10, 2016.
(Continued)

(51) Int. Cl.
*B01L 3/00* (2006.01)
*B01L 3/02* (2006.01)

(52) U.S. Cl.
CPC ............ *B01L 3/563* (2013.01); *B01L 3/0275* (2013.01); *B01L 2200/025* (2013.01);
(Continued)

(58) Field of Classification Search
CPC combination set(s) only.
See application file for complete search history.

(56) References Cited

U.S. PATENT DOCUMENTS

| 4,023,716 A | 5/1977 | Shapiro |
| 4,187,724 A | 2/1980 | Citrin |

(Continued)

FOREIGN PATENT DOCUMENTS

| DE | 102015213005 | 12/2017 |
| EP | 2311566 | 4/2011 |

(Continued)

*Primary Examiner* — Brian R Gordon
(74) *Attorney, Agent, or Firm* — Weintraub Tobin

(57) ABSTRACT

Pipette assembly comprising a pipette device, a pipette tip, and an expanding mandrel collet coupling device coupling the tip to the pipette device, the coupling device comprising: circumferentially spaced apart segments, an annular base disposed below the segments and comprising a distal portion, an elastomeric element circumscribing the distal portion, and upwardly extending circumferentially spaced apart arms attached at first ends to the annular base and having upper free ends each supporting a different one of the segments configured to expand between a first and a second greater circumference for engaging a first interior working surface of the tip in concurrence with the elastomeric element sealing against a second interior working surface below the first surface and in concurrence with an abutment between a disk exteriorly disposed about a medial portion of the arms and a stepped interior shoulder of the tip disposed between the first and second working surfaces.

30 Claims, 44 Drawing Sheets

Related U.S. Application Data

(60) Provisional application No. 62/350,302, filed on Jun. 15, 2016, provisional application No. 62/350,291, filed on Jun. 15, 2016.

(52) U.S. Cl.
CPC .. *B01L 2200/026* (2013.01); *B01L 2200/0689* (2013.01); *B01L 2300/0832* (2013.01); *B01L 2300/123* (2013.01)

(56) References Cited

U.S. PATENT DOCUMENTS

| | | | |
|---|---|---|---|
| 4,284,604 A * | 8/1981 | Tervamaki | B01L 3/0224 |
| | | | 422/517 |
| 4,830,832 A | 5/1989 | Arpagaus | |
| 4,863,695 A | 9/1989 | Fullemann | |
| 4,967,604 A | 11/1990 | Arpagaus | |
| 5,121,642 A * | 6/1992 | Davidowicz | B01L 3/02 |
| | | | 422/919 |
| 5,200,151 A | 4/1993 | Long | |
| 5,232,669 A * | 8/1993 | Pardinas | B01L 3/0275 |
| | | | 206/562 |
| 5,525,302 A * | 6/1996 | Astle | B01L 3/0279 |
| | | | 422/511 |
| 5,620,660 A | 4/1997 | Belgardt | |
| 5,948,359 A * | 9/1999 | Kalra | G01N 1/312 |
| | | | 422/510 |
| 6,168,761 B1 | 1/2001 | Kelly | |
| 6,171,553 B1 | 1/2001 | Petrek | |
| 6,248,295 B1 | 6/2001 | Petrek | |
| 6,399,024 B1 | 6/2002 | Bevirt | |
| 6,495,106 B1 | 12/2002 | Kalra | |
| 6,499,363 B1 * | 12/2002 | Morimoto | B01L 3/0231 |
| | | | 73/864.01 |
| 6,568,288 B2 | 5/2003 | Rainin | |
| 6,596,240 B2 * | 7/2003 | Taggart | B01L 3/0275 |
| | | | 422/525 |
| 6,673,318 B1 * | 1/2004 | Nishimura | B01L 3/0279 |
| | | | 222/542 |
| 6,737,023 B1 | 5/2004 | Kelly | |
| 6,745,636 B2 | 6/2004 | Rainin | |
| 6,780,381 B2 | 8/2004 | Yiu | |
| 6,955,077 B2 | 10/2005 | Blaszcak | |
| 6,967,004 B2 | 11/2005 | Rainin | |
| 6,973,845 B2 | 12/2005 | Bell | |
| 7,033,543 B1 | 4/2006 | Panzer | |
| 7,047,828 B2 | 5/2006 | Blaszcak | |
| 7,320,259 B2 | 1/2008 | Jessop | |
| 7,335,337 B1 * | 2/2008 | Smith | B01L 3/0275 |
| | | | 422/513 |
| 7,344,680 B2 | 3/2008 | Mahler | |
| 7,641,859 B2 | 1/2010 | Cote | |
| 7,662,343 B2 | 2/2010 | Mathus | |
| 7,662,344 B2 | 2/2010 | Mathus | |
| 7,690,293 B2 | 4/2010 | Bensley | |
| 7,785,466 B1 * | 8/2010 | Smith | B01L 3/0275 |
| | | | 210/321.75 |
| 8,163,256 B2 | 4/2012 | Cote | |
| 8,202,495 B1 * | 6/2012 | Smith | B01L 3/0275 |
| | | | 422/500 |
| 8,277,757 B2 | 10/2012 | Kelly | |
| 8,337,782 B2 | 12/2012 | Bensley | |
| 8,398,934 B2 | 3/2013 | Bensley | |
| 8,501,118 B2 | 8/2013 | Mathus | |
| 8,512,650 B2 | 8/2013 | Jungheim | |
| 8,524,170 B2 | 9/2013 | Petrek | |
| 8,557,197 B2 | 10/2013 | Leckebusch | |
| 8,703,071 B2 | 4/2014 | Cerra | |
| 8,877,513 B2 | 11/2014 | Mathus | |
| 9,079,178 B2 | 7/2015 | Sheldon | |
| 9,333,500 B2 | 5/2016 | Mathus | |
| 9,346,045 B2 | 5/2016 | Blumentritt | |
| 9,415,388 B2 | 8/2016 | Panzer | |
| 2002/0001545 A1 * | 1/2002 | Cronenberg | B01L 3/0279 |
| | | | 422/525 |
| 2003/0082078 A1 * | 5/2003 | Rainin | B01L 3/0279 |
| | | | 422/522 |
| 2003/0177849 A1 * | 9/2003 | Matsuda | B01L 3/0279 |
| | | | 73/864.14 |
| 2005/0175511 A1 | 8/2005 | Cote | |
| 2005/0184516 A1 | 8/2005 | Seguin | |
| 2005/0204832 A1 | 9/2005 | Jessop | |
| 2005/0255005 A1 | 11/2005 | Motadel | |
| 2006/0093527 A1 * | 5/2006 | Buss | A61M 1/0084 |
| | | | 422/501 |
| 2006/0233669 A1 | 10/2006 | Panzer | |
| 2008/0078258 A1 | 4/2008 | Price | |
| 2010/0196210 A1 * | 8/2010 | Jungheim | B01L 3/0275 |
| | | | 422/526 |
| 2011/0076205 A1 | 3/2011 | Kelly | |
| 2013/0136672 A1 | 5/2013 | Blumentritt | |
| 2013/0216705 A1 | 8/2013 | Sprung | |
| 2014/0056781 A1 | 2/2014 | Jaaskelainen | |
| 2014/0219887 A1 * | 8/2014 | Sheldon | B01L 3/0279 |
| | | | 422/509 |
| 2015/0037227 A1 * | 2/2015 | Ding | B01L 3/0293 |
| | | | 422/509 |
| 2015/0086447 A1 | 3/2015 | Mathus | |
| 2015/0239129 A1 | 8/2015 | Buchloh | |
| 2015/0276107 A1 | 10/2015 | Stadler | |
| 2016/0051979 A1 | 2/2016 | Herbst | |
| 2017/0361323 A1 * | 12/2017 | Guzman | B01L 3/563 |

FOREIGN PATENT DOCUMENTS

| | | |
|---|---|---|
| JP | 3748231 | 2/2006 |
| KR | 20120008943 | 12/2012 |

* cited by examiner

2251

2252

2253

2254

2255

2256

PIPETTING DEVICE, PIPETTE TIP COUPLER, AND PIPETTE TIP: DEVICES AND METHODS

CROSS-REFERENCE TO RELATED APPLICATIONS

This application is a continuation of and claims the benefit of priority from U.S. patent application Ser. No. 15/348,298, which is entitled "Pipetting Device, Pipette Tip Coupler, and Pipette Tip: Devices and Methods" and filed on Nov. 10, 2016, which claims the benefit of priority from two (2) U.S. Provisional Patent Application Nos. 62/350,291 filed Jun. 15, 2016, and 62/350,302 filed Jun. 15, 2016, all of which are fully incorporated herein by reference.

FIELD

This disclosure pertains generally to pipetting devices, and more particularly to pipette tip couplers, disposable pipette tips, pipette tip and coupler combinations, and coupling and decoupling methods of at least one disposable pipette tip to or from at least one pipette tip coupler operatively carried by a pipette device.

BACKGROUND

Pipette devices are used in a multitude of industries for the transfer of liquids to conduct experimental analysis. As such, to provide control within the experiments being performed, disposable pipette tips are used and intended for one-time use. Disposable pipette tips are employed with both manual pipette devices and automated pipette devices having a large number of pipette units arranged in a row or in a matrix for aspirating samples simultaneously from a large number of vessels and dispensing them elsewhere.

Disposable pipette tips have been constructed historically to interface to either a conical or stepped coupling stud. In the cases where a conical coupling stud is used, the disposable pipette tip is constructed in a manner that it must be pre-stressed onto the coupling stud to provide an airtight seal. Due to the tolerances of the two interfacing components, the distance to the end of the pipette tip that comes in contact with liquid is not well controlled. In addition, high press forces are required to pre-stress the pipette tip to create the air tight seal. As a result, microfissures may be formed in the pipette tip which are a cause of leakage. Moreover, the high press forces upon placement of the pipette tip have the disadvantage that for the release of the pipette tip correspondingly high forces have to be applied.

The assignee of the present application, HAMILTON Company, teaches in U.S. Pat. No. 7,033,543, issued Apr. 25, 2006, a stepped coupling stud in conjunction with an O-ring that provides a solution for reducing the high press force required to create an air tight seal as well as providing well defined axial positioning of the end of the pipette tip that comes in contact with liquid. As the O-ring is compressed, it provides axially directed force to not only provide the air-tight seal, but to engage the axial coupling feature on the coupling stud to the counter axial coupling feature on the pipette tip.

Notwithstanding, current systems utilizing a stepped coupling stud and a solitary O-ring configuration are problematic when the O-ring becomes compromised because the result is an impairment in the air-tight seal and the performance of the pipette device.

Additionally, the compression of the O-ring results in the deformation of the O ring which in turn provides the axially directed force and air-tight seal against the working surface of the pipette tip. Counter to this operation, when the compression of the O-ring is removed, the O-ring must disengage from the working surface of the pipette tip to allow the pipette tip to be removed from the coupling stud and the pipette device for disposal. If the O-ring does not fully decompress, some residual force will remain resulting in keeping the pipette tip engaged to the coupling stud and thus requiring an automated external axial counterforce to remove the pipette tip for disposal.

Moreover, as the size of the holes to and/or from which liquid is transferred decreases, the need for precision positioning of all of the pipette tips in a controlled manner increases in order to allow successful targeting.

Hence, there is a need to ameliorate or overcome one or more of the significant shortcomings delineated hereinabove.

SUMMARY

Accordingly, and in one aspect, an embodiment of the present disclosure ameliorates or overcomes one or more of the shortcomings of the known prior art by providing a pipette tip coupler and disposable pipette tip combination which comprises a plurality of circumferentially disposed elements or segments engaging a circumferential interior working surface defining a first working surface formed into an interior circumscribing surface of a sidewall of the pipette tip in an area superior to a proximally facing axial stop surface of the pipette tip for providing a resultant pre-stress force which pre-stresses the pipette tip axially upward causing a distal elastomeric element of the coupler to be pre-stressed against a second interior working surface of the pipette tip forming a seal configuration that eliminates the seal deterioration or failure of the known prior art.

In addition, and in one aspect, the distal elastomeric element, when compressed against the second interior working surface, provides a counter axial force to the plurality of elements or segments wherein at least one benefit of this counter axial force is that additional force is applied to the first working surface by the plurality of individual elements or segments when the plurality of individual elements or segments are in a radially and axially interfacing state for providing a stronger distal seal.

A further benefit of the counter axial force is that when the plurality of individual elements or segments are disengaged to a radially retracted state, the counter axial force of the distal elastomeric element defines a counter axially directed disengaging force that aids in the removal of the pipette tip from the pipette tip coupler for disposal.

In another aspect, an embodiment of the present disclosure provides a pipette tip coupler and disposable pipette tip combination, the coupler comprising a plurality of circumferentially disposed elements or segments and a distal elastomeric element in the form of, but not limited to, an O-ring and the pipette tip comprising dual complemental interior working surfaces in the pipette tip to provide a resultant axial force achieved from an engagement of the plurality of elements or segments and the distal elastomeric element with the dual complemental working surfaces for pre-stressing the disposable pipette tip into an axial coupling position which is provided by a distally facing axial stop surface of the pipette tip coupler and a proximally facing complimentary counter axial stop surface of the disposable pipette tip such that a perpendicular datum is established to a longitudinal axis of a channel of a pipette device carrying the pipette tip coupler and disposable pipette tip combination which provides for pipette tip straightness and controlled concentricity.

Thus, one benefit of the resultant axial force coupling position over the known prior art is the establishment of this perpendicular datum which provides for pipette tip straightness and controlled concentricity. Concentricity becomes worse as an angle defined herein as "ø" between a transverse axis and the longitudinal axis perpendicular to the transverse axis is allowed to increase. Thus, controlled concentricity becomes especially important on a multi-channel system and targeting multiple wells. Accordingly, the pipette tip coupler and disposable pipette tip combination provides tighter concentricity to allow for tighter precision of all the pipette tips in a controlled manner allowing successful targeting of multiple wells and/or smaller holes to and/or from which liquid is transferred.

In another aspect, an embodiment of the present disclosure provides a pipette tip coupler and disposable pipette tip combination, the coupler comprising a plurality of circumferentially disposed elements or segments and a distal elastomeric element in the form of, but not limited to, an O-ring and the pipette tip comprising dual complementary working surfaces in the pipette tip to provide precise control of an axial coupled position defined as an axial distance from a distally facing axial stop surface of the pipette tip coupler to the end of the pipette tip that contacts liquid when the pipette tip coupler and disposable pipette tip are in a coupled configuration. This, combined with pipette tip straightness, allows for a pipette device carrying the pipette tip coupler and disposable pipette tip combination to target smaller holes. Additionally, smaller volumes of liquid can be transferred resulting from the known fixed distance of the disposable pipette tip allowing for a controlled touch of the pipette tip/liquid to a working surface onto or from which liquid is to be transferred.

In yet another aspect, an embodiment of the present disclosure provides a pipette tip coupler and disposable pipette tip combination comprising an angled squeeze mechanism that directs the motion of the plurality of individual elements into contact with the first working surface of the pipette tip. The result is more axial force to pre-stress the pipette tip into the axial coupling position.

Further aspects of the embodiments of the present disclosure will become apparent from the detailed description provided below, when taken together with the attached drawings and claims. It should be understood, however, that numerous modifications and adaptations may be resorted to without departing from the scope and fair meaning of the claims as set forth below following the detailed description of preferred embodiments of the present disclosure.

BRIEF DESCRIPTION OF THE SEVERAL VIEWS OF THE DRAWINGS

The foregoing summary, as well as the following detailed description of the disclosure, will be more fully understood by reference to the following drawings which are for illustrative purposes only, and are not intended to limit the scope of the present disclosure. Also, it is appreciable that the drawings are not necessarily in scale as some components may be shown to be enlarged or to be out of proportion relative to the size in actual implementation in order to more clearly illustrate one or more concepts of the present disclosure. In the drawings.

DETAILED DESCRIPTION

Figure 1:
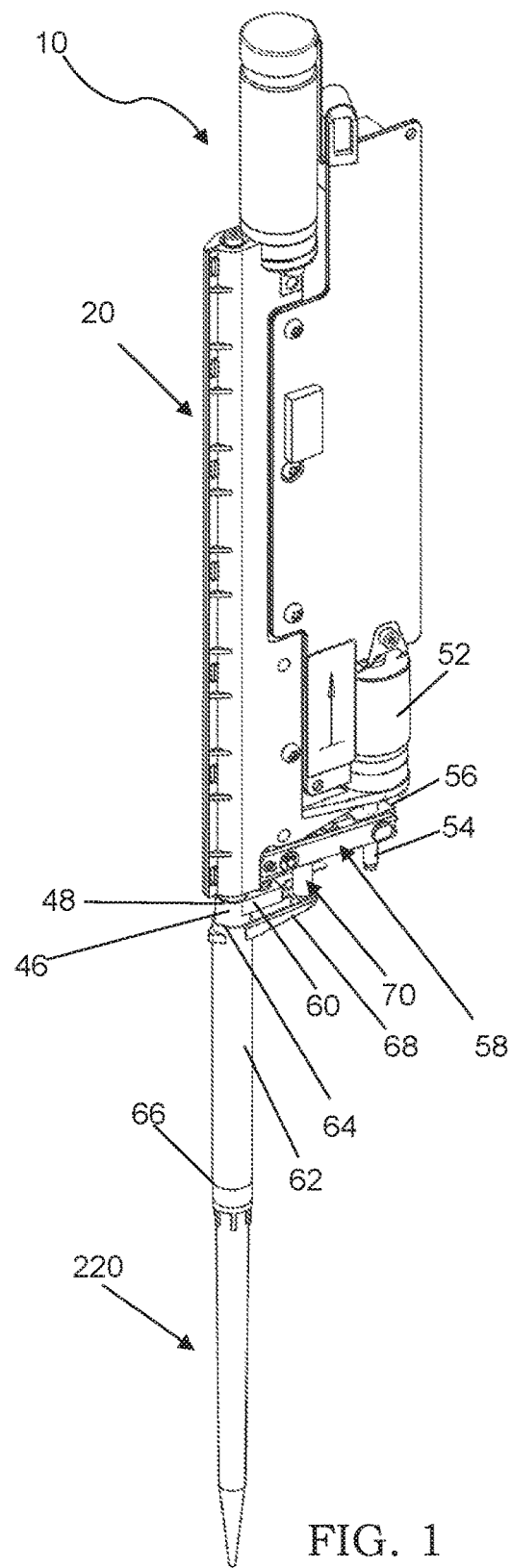
FIG. 1 is a perspective view of an example embodiment of an air displacement pipette device assembly of an automated liquid handling system.

For the purpose of illustrating the disclosure, there are shown in the drawings embodiments which are presently preferred. These example embodiments will now be described more fully with reference to the accompanying drawings wherein like reference numerals are used to denote like parts or portions throughout the description of the several views of the drawings.

Pipette Assembly with Expanding Mandrel Collet Coupling and Tip

Figure 2:
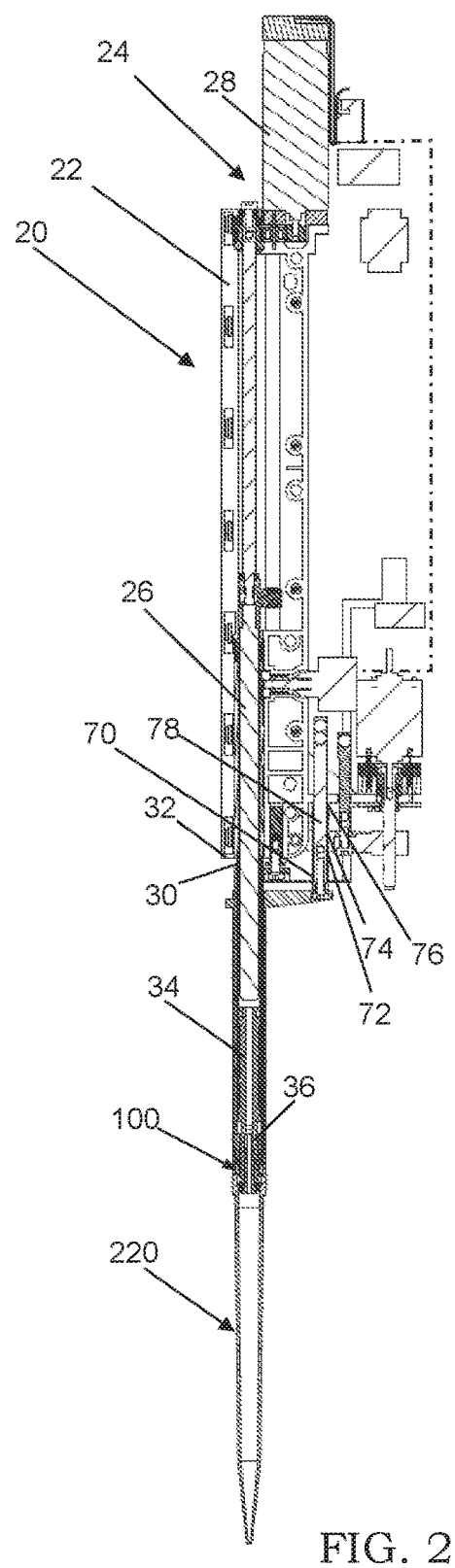
FIG. 2 is a longitudinal sectional, side elevational view of the example embodiment of the pipette device assembly.

FIGS. 1 and 2 illustrate an example embodiment of a pipette device assembly 10 comprising an example embodiment of a pipette device 20, an example embodiment of an expanding mandrel collet coupling device 100 or pipette tip coupler, and an example embodiment of a disposable pipette tip 220 removably coupled to the pipette device 20 by way of the expanding mandrel collet coupling device 100.

Pipette Device 20

Referring to FIG. 2, the pipette device 20 comprises a body 22 supporting an aspirating and dispensing device 24 comprising a plunger 26 operatively coupled to and driven by a motor 28. The plunger 26 resides within a plunger cylinder 30 extending from a distal or lower end 32 of the body 22 of the pipette device 20.

Pipette device 20 further comprises an aspirating and dispensing cylinder 34 that is at least partially disposed within plunger cylinder 30 at a location axially aligned with and distally below the plunger 26. The aspirating and dispensing cylinder 34 distally transitions into a distal mounting flange 36 for attaching with the expanding mandrel collet coupling device 100 which, in turn, removably couples with the disposable pipette tip 220.

Figure 3:
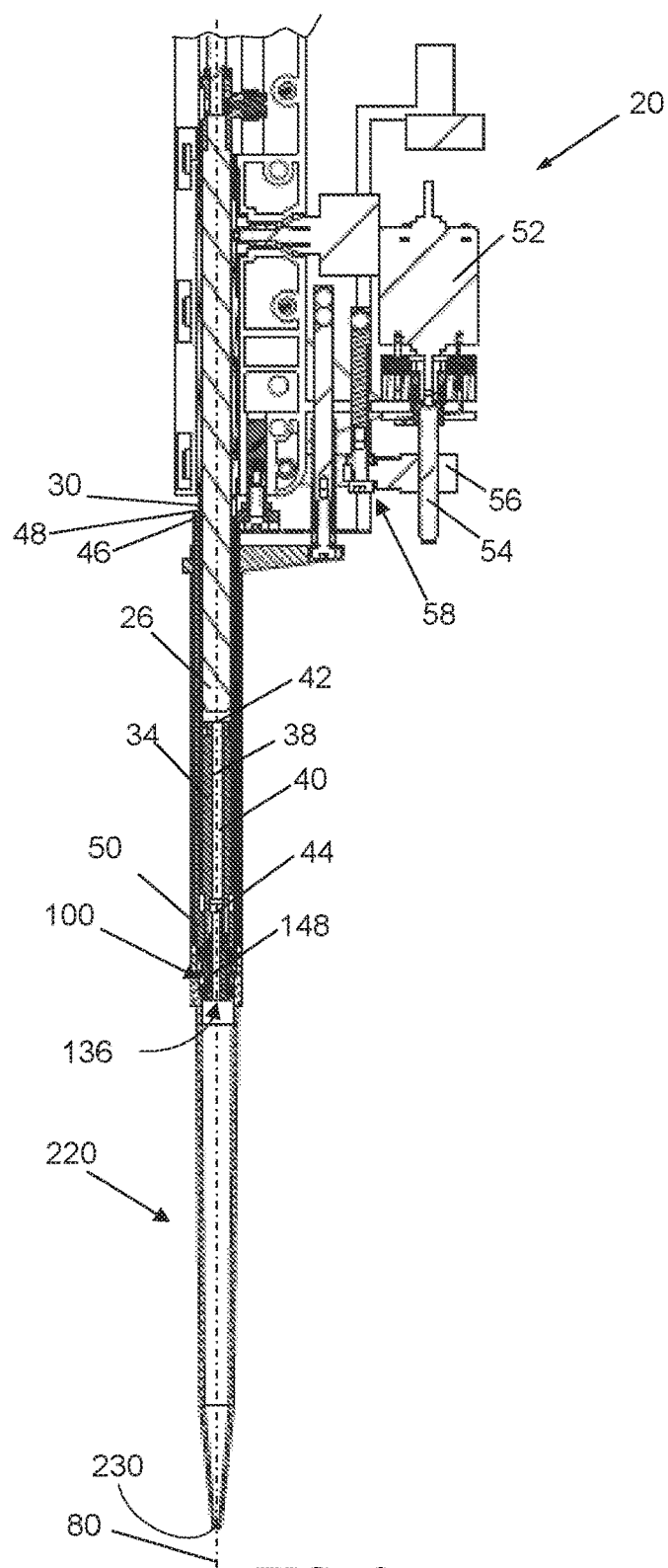
FIG. 3 is a fragmentary longitudinal sectional, side elevational view of the example embodiment of the pipette device assembly comprising a pipette device operatively coupled to an example embodiment of an expanding mandrel collet coupling device or pipette tip coupler that is operatively coupled to an example embodiment of a disposable pipette tip.
Figure 15:
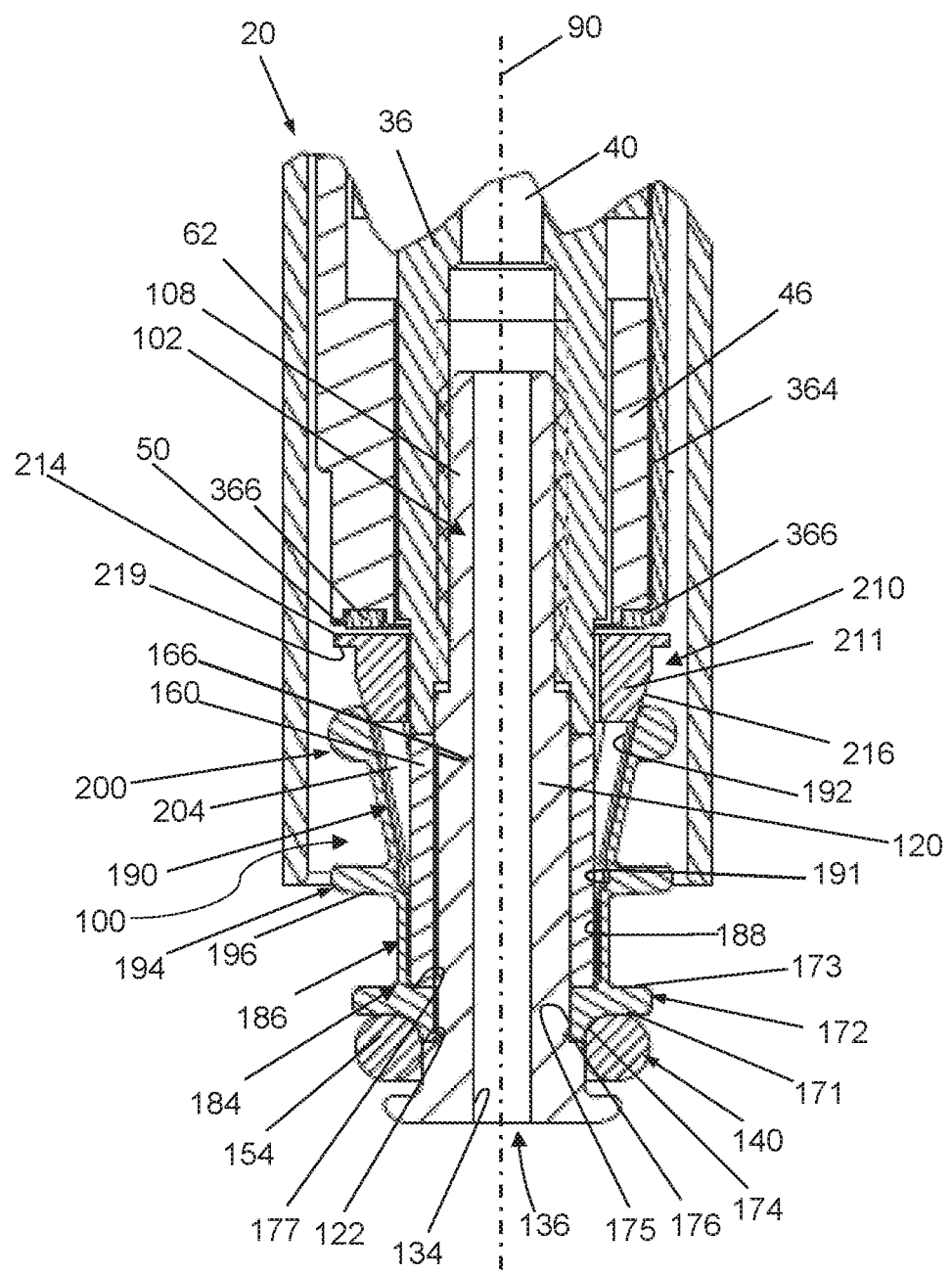
FIG. 15 is a fragmentary, longitudinal sectional, side elevational view of the example embodiment of the expanding mandrel collet of the expanding mandrel collet coupling device operatively coupled to the pipette device.

Referring to FIGS. 1, 3, and 15, the aspirating and dispensing cylinder 34 further comprises an interior circumscribing sidewall 38 that defines an open ended pipette channel 40 extending therethrough. The open ended pipette channel 40 longitudinally extends along a longitudinal channel axis 80 of the pipette device assembly 10 between an open upper end portion 42 and open lower end portion 44 of the aspirating and dispensing cylinder 34 for providing open communication between plunger 26 and an exterior area adjacent distal mounting flange 36 wherein the distal mounting flange 36 is operatively connected to a central body member 102 of the expanding mandrel collet coupling device 100 and the central body member 102 comprising an open ended central channel 136 extending through the central body member 102 to provide open communication between the tip 220 and the aspirating and dispensing cylinder 34 via the expanding mandrel collet coupling device 100.

Piston or Squeeze Sleeve 46

Figure 4:
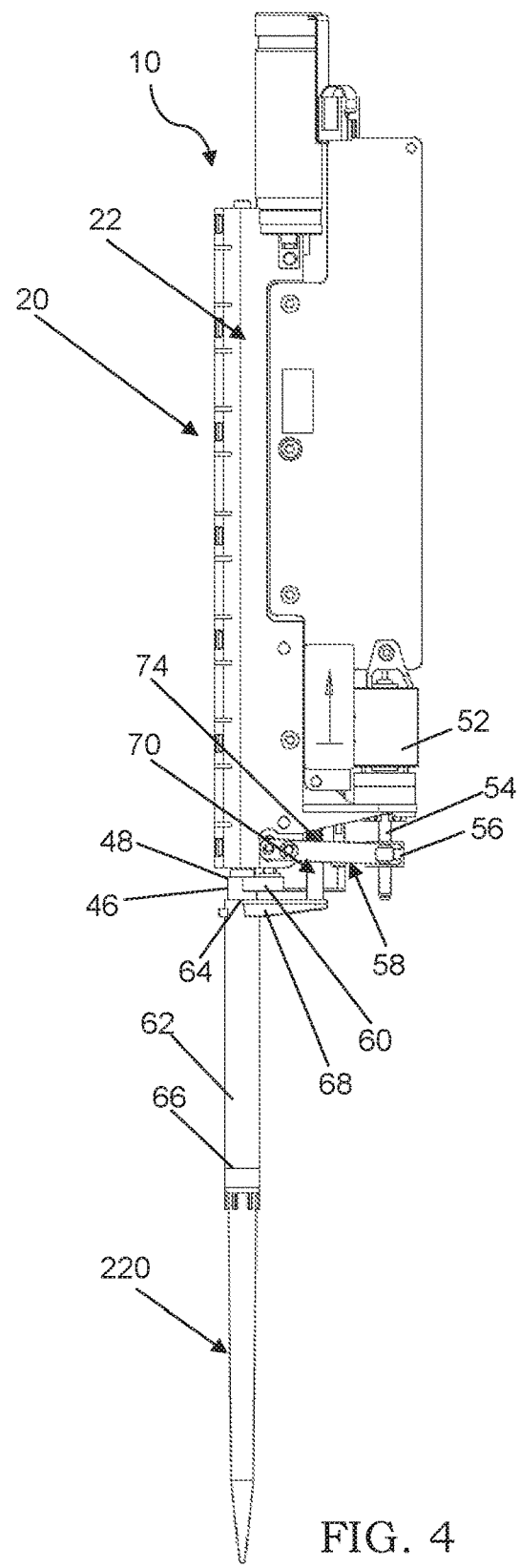
FIG. 4 is a side elevational view of the example embodiment of the pipette device assembly.

Referring to FIGS. 3 and 4, the pipette device 20 further comprises a hollow piston or squeeze sleeve 46 having a proximal or upper end 48 and a distal or lower end 50. The squeeze sleeve 46 circumscribes both the plunger cylinder 30 and the aspirating and dispensing cylinder 34 and is operatively coupled to a squeeze motor 52.

As illustrated in FIG. 4, the squeeze motor 52 of pipette device assembly 10 is supported on the body 22 of the device 20 and is operatively coupled to and drives a lead screw 54 which, in turn, couples to an axially translating lead nut 56 that is operatively coupled to a squeeze linkage 58. The squeeze linkage 58 is operatively coupled to the proximal or upper end 48 of the squeeze sleeve 46 via squeeze linkage arm 60 such that rotation of the squeeze motor 52 in a first direction results in linear axial translation of the squeeze sleeve 46 in a distal or vertically downward direction along longitudinal channel axis 80 (FIG. 3) and such that subsequent rotation of the squeeze motor 52 in a second or opposite direction results in linear counter axial translation of the squeeze sleeve 46 in a proximal or vertically upward direction opposite the downward direction along longitudinal channel axis 80 (FIG. 3).

Ejection Sleeve 62

Referring to FIG. 4, the pipette device 20 further comprises an ejection sleeve 62 used to eject the disposable pipette tip 220 from the pipette device 20 wherein the ejection sleeve 62 is axially movable relative to the aspirating and dispensing cylinder 34 (FIG. 2) and comprises a proximal or upper end 64, a distal or lower end 66, and an ejection sleeve arm 68 attached at a first end to the ejection sleeve 62 adjacent upper end 64 and having an opposing second end attached to a first end of a plunger device 70.

Figure 5:
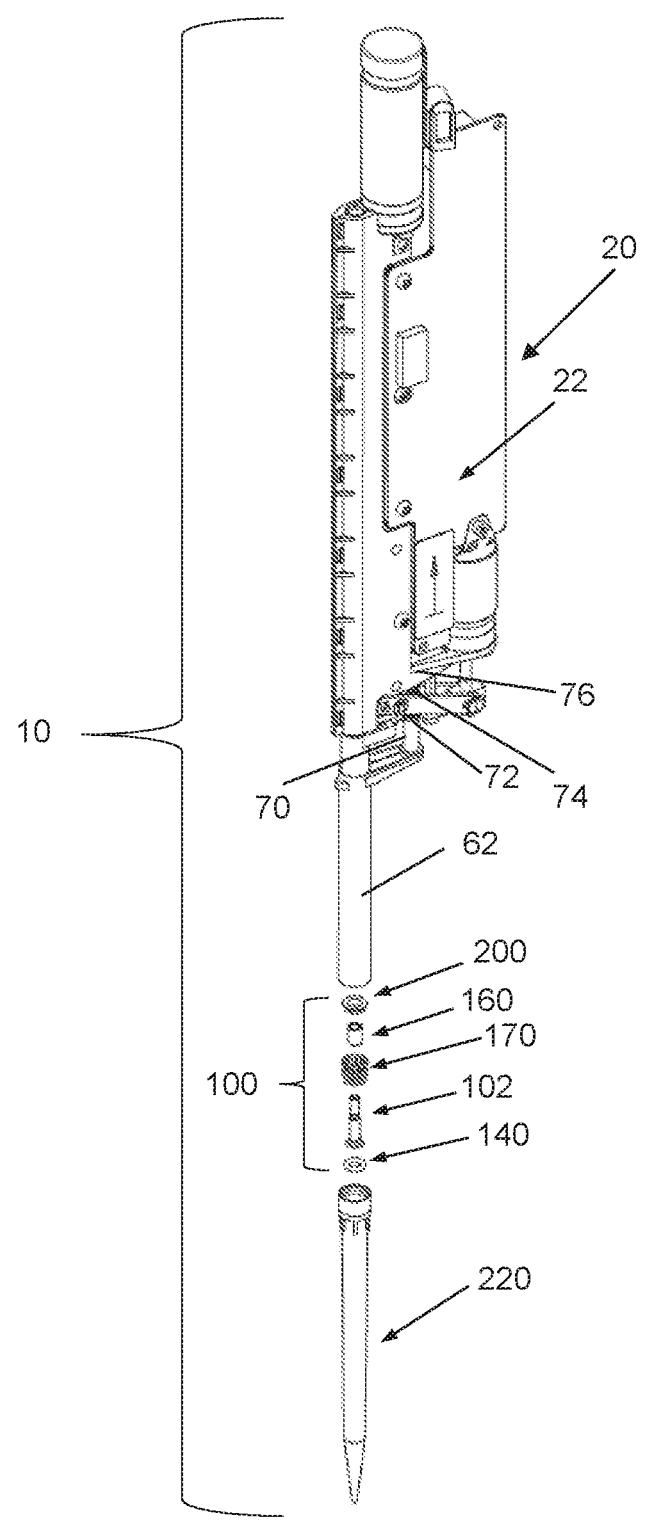
FIG. 5 is a partial exploded parts perspective view of the pipette device assembly detailing parts of the example embodiment of the expanding mandrel collet coupling device.

As illustrated in FIG. 5, the plunger device 70 comprises an opposing end surface 72 abutting one end of an ejection sleeve spring 74 having an opposing spring end abutting against an upper surface portion 76 of the body 22 of device 20 wherein the ejection sleeve spring 74 is captured between the surfaces 72, 76 to be spring loaded to bias the plunger device 70 and attached sleeve 62 in a normally pipette tip ejected state.

The normally pipette tip ejected state is configured to require a force, such as coupling to pipette tip 220, to overcome the ejection sleeve spring force in order to axially push the ejection sleeve 62 to a retracted state as illustrated in FIG. 2. FIG. 2 further illustrates that the spring 74 circumscribes a central spring guide member 78 for retaining the shape of the spring 74 and for preclude the spring 74 from buckling.

Furthermore, the spring 74 is dimensioned in such a way that the force exerted on the pipette tip 220 by sleeve 62 in the course of its relaxation is sufficient to assist in ejecting the tip 220 from the expanding mandrel collet coupling device 100.

It should be appreciated that the expanding mandrel collet coupling device 100 and the disposable pipette tip 220 can be practiced on other embodiments of pipette devices wherein the embodiment of pipette device 20 is provided by way of example only and not limitation.

Expanding Mandrel Collet Coupling Device 100

Figure 6:
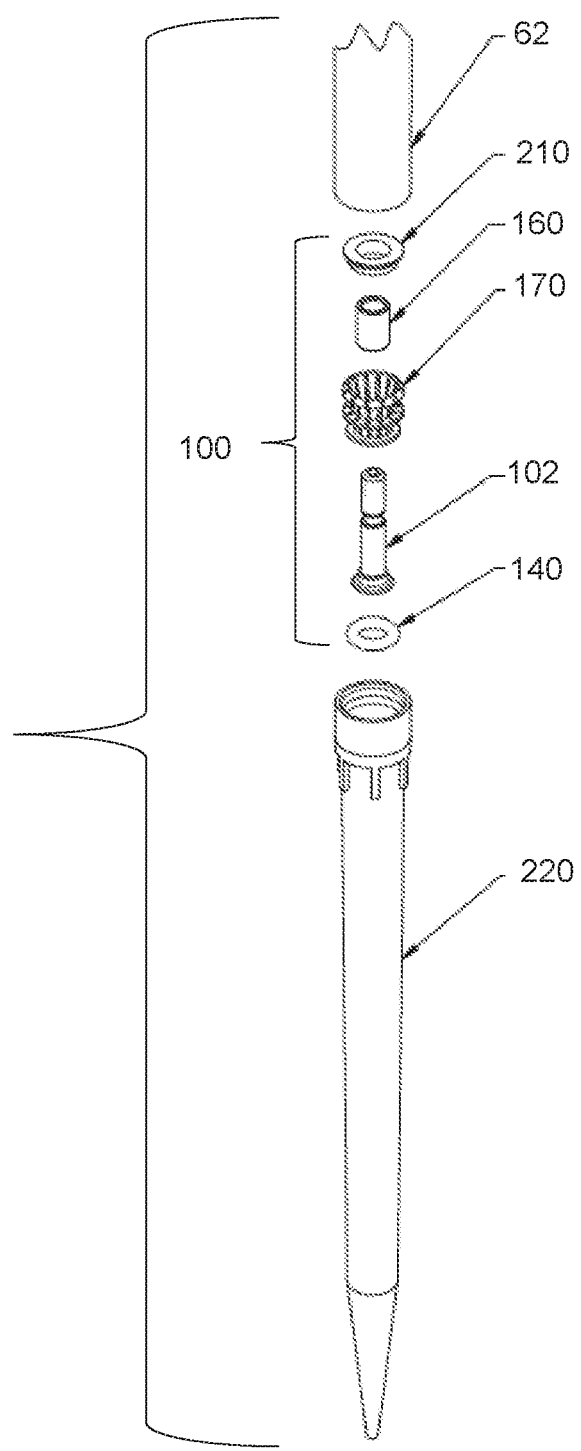
FIG. 6 is a fragmentary, partial exploded parts perspective view detailing parts of the example embodiment of the expanding mandrel collet coupling device interposed between the disposable pipette tip and the pipette device.
Figure 7:
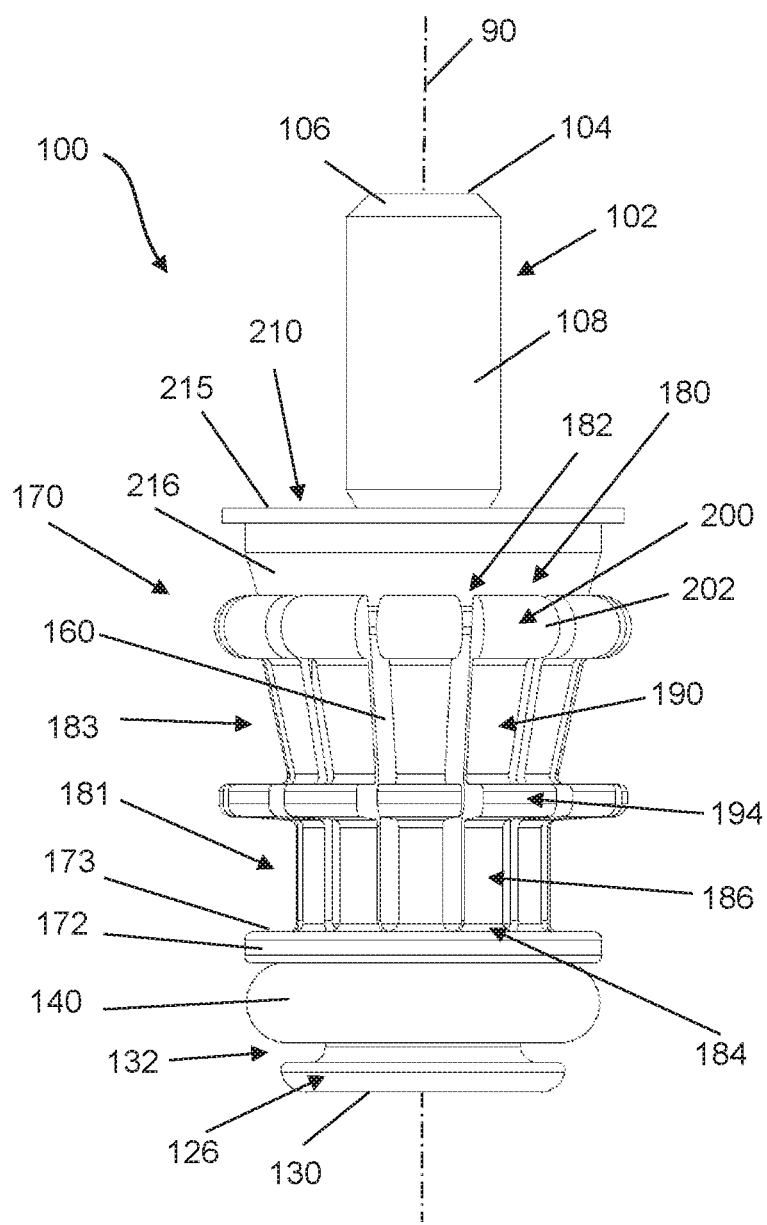
FIG. 7 is a side elevational view of the example embodiment of the expanding mandrel collet coupling device.

Referring to FIGS. 5 through 7, the expanding mandrel collet coupling device 100 comprises an elongated central body member 102; a distal or lower elastomeric element 140 carried at a distal or lower end portion of the elongated central body member 102; an expanding collet 170 configured to circumscribe the elongated central body member 102 and comprising a segmented collar 200; and an annular wedge or washer 210.

Figure 21:
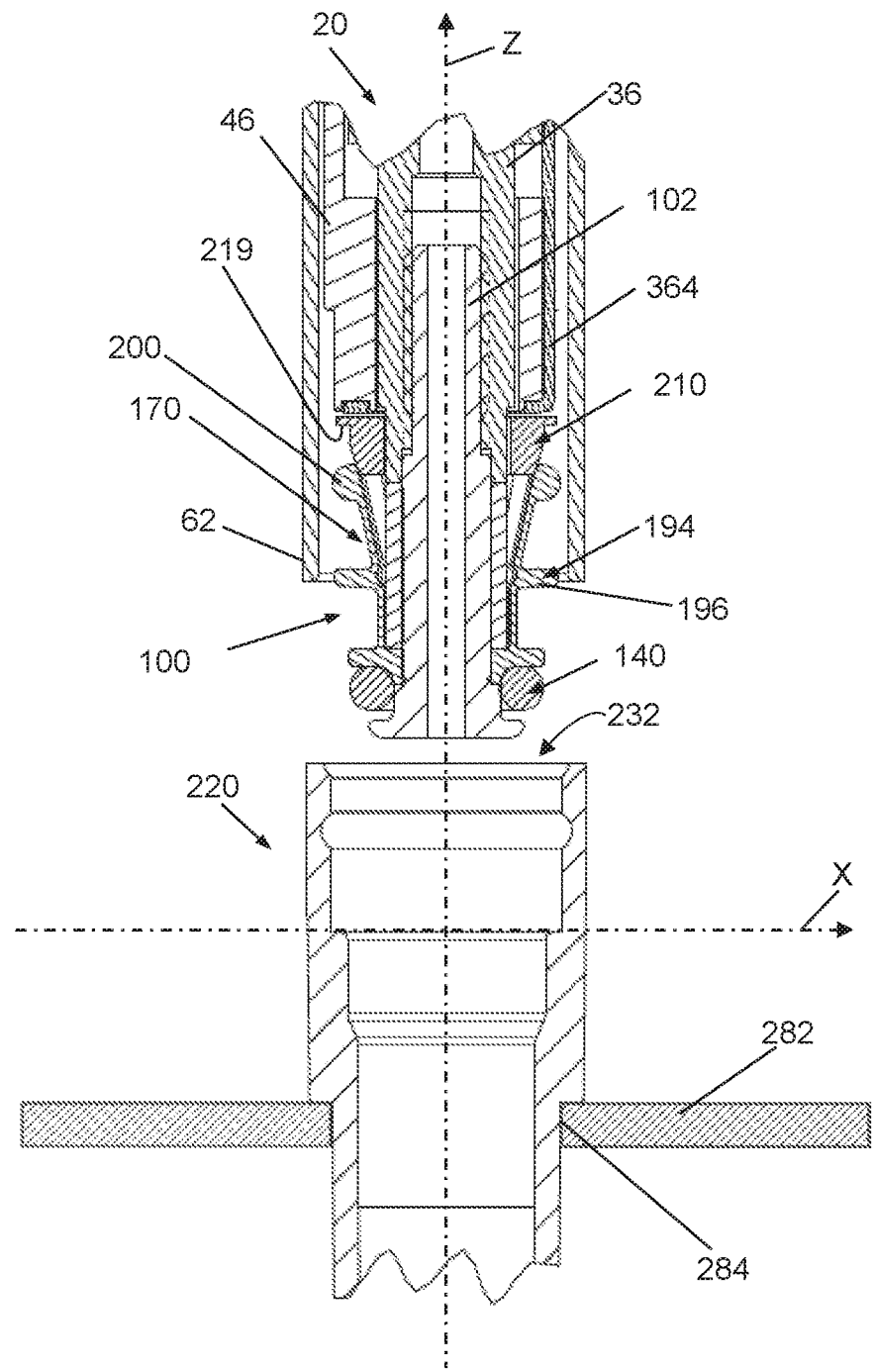
FIG. 21 is a fragmentary, longitudinal sectional, side elevational view of the example embodiment of the pipette device supporting the example embodiment of the expanding mandrel collet coupling device over the disposable pipette tip.
Figure 29:
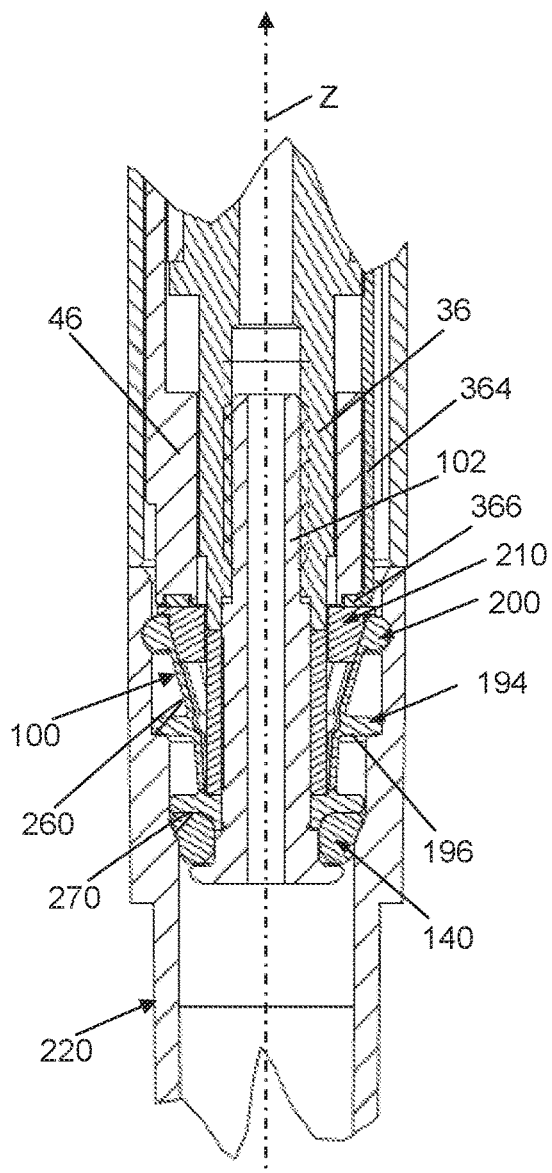
FIG. 29 is a fragmentary, longitudinal sectional, side elevational view of the example embodiment of the expanding mandrel collet coupling device positioned in the disposable pipette tip with the pipette tip being lifted up to its final seated state by the annular wedge being moved to its final position thereby defining a final coupling state with the distal elastomeric element in a final compressed seated sealing state against the sealing seat surface of the pipette tip.

The annular wedge 210 is configured to receive an upper portion of the elongated central body member 102 therethrough for axially movably surmounting an interior of the expanding collet 170 adjacent segmented collar 200 for radially outwardly expanding the segmented collar 200 from the unexpanded state having a first circumference to an expanded state having a second conference greater than the first circumference as a function of the axial location of the annular wedge 210 relative to the central body member 102 for engaging the interior of the pipette tip 220 as illustrated in FIG. 29 from a disengaged state as illustrated in FIG. 21.

Elongated Central Body Member 102

Figure 8:
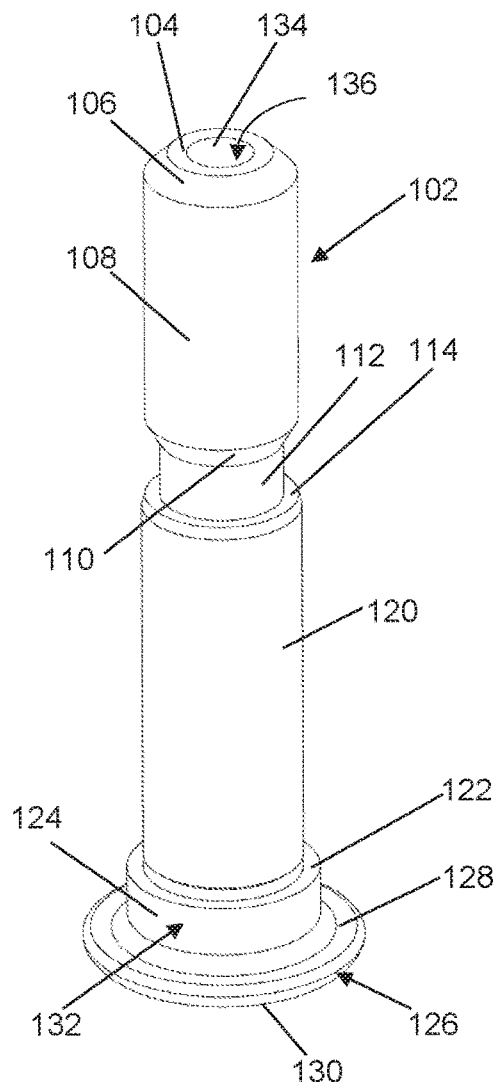
FIG. 8 is a top and side perspective view of a central coupler body of the example embodiment of the expanding mandrel collet coupling device.

More specifically, and referring to FIGS. 7 and 8, the expanding mandrel collet coupling device 100 comprises the elongated central body member 102 extending between a proximal or upper annular end face 104 and a distal or lower annular end face 130 along a longitudinal central axis 90.

As illustrated in FIG. 8, the upper annular end face 104 of central body member 102 comprises an outer chamfered periphery 106 that transitions into an elongated tubular upper shank member 108 that distally transitions into an annular tapered portion 110. In one embodiment, shank member 108 is threaded for assembly with distal mounting flange 36, which has corresponding threads. Annular tapered portion 110 decreases in diameter from shank member 108 and distally transitions into a cylindrical neck portion 112. The cylindrical neck portion 112 distally transitions into a cylindrical collar 114 that has a diameter greater than a diameter of the cylindrical neck portion 112.

The cylindrical collar 114 is followed by a lower cylindrical body member 120 that has a diameter greater than a diameter of the cylindrical neck portion 112. Body member 120 distally extends from the cylindrical collar 114 to an upper annular shoulder end or stop surface 122 of a distal cylindrical stem portion surface 124 that has a diameter greater than a diameter of the lower cylindrical body member 120.

As also illustrated in FIG. 8, the distal cylindrical stem portion surface 124 transitions from upper annular shoulder end 122 into a round end plate 126 having an upper surface 128 and a lower surface defined by the distal or lower annular end face 130. As illustrated, the end plate 126 has a diameter greater than a diameter of the stem portion surface 124 wherein the distal stem portion surface 124 defines a distal or lower groove portion 132 of the expanding mandrel collet coupling device 100.

Referring to FIGS. 8 and 15, the elongated central body member 102 comprises an interior cylindrical channel surface 134 defining an open ended cylindrically shaped central channel or passageway 136 extending through the central body member 102 between the upper annular end face 104 and the lower annular end face 130 along the longitudinal central axis 90 for providing open channel communication through the elongated central body member 102 and to the open ended pipette channel 40 longitudinally extending along the longitudinal channel axis 80 of the pipette device assembly 10.

Distal Elastomeric Element 140

As further illustrated in FIG. 7, the expanding mandrel collet coupling device 100 further comprises the distal or lower elastomeric element 140 coaxially carried at the distal end portion of the elongated central body member 102.

Figure 9:
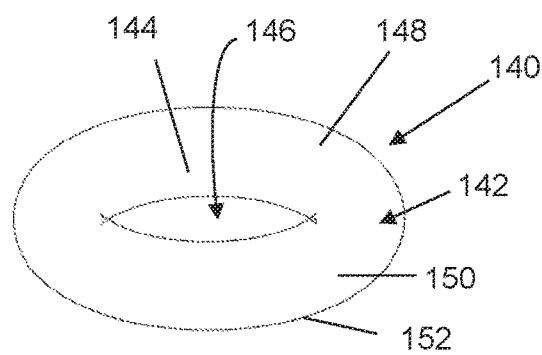
FIG. 9 is a top and side perspective view of an example embodiment of a lower or distal elastomeric element or O-ring of the example embodiment of the expanding mandrel collet coupling device.

In one embodiment, and referring FIG. 9, the distal elastomeric element 140 comprises an annular body 142. Annular body 142 comprises an interior surface 144 defining a central opening 146, a top surface 148, a peripheral exterior surface 150, and a bottom surface 152. Central opening 146 is dimensioned to closely or tightly circumscribe the distal cylindrical stem portion 124 of the expanding mandrel collet coupling device 100 while shaped to reside within groove 132 and extend radially outwardly circumferentially beyond end plate 126 as illustrated in FIG. 7. In a relaxed or unsqueezed state, the distal elastomeric element 140 comprises a circumferentially continuous, generally circular cross section area 154 as is illustrated in FIG. 15.

Spacer 160

Figure 10:
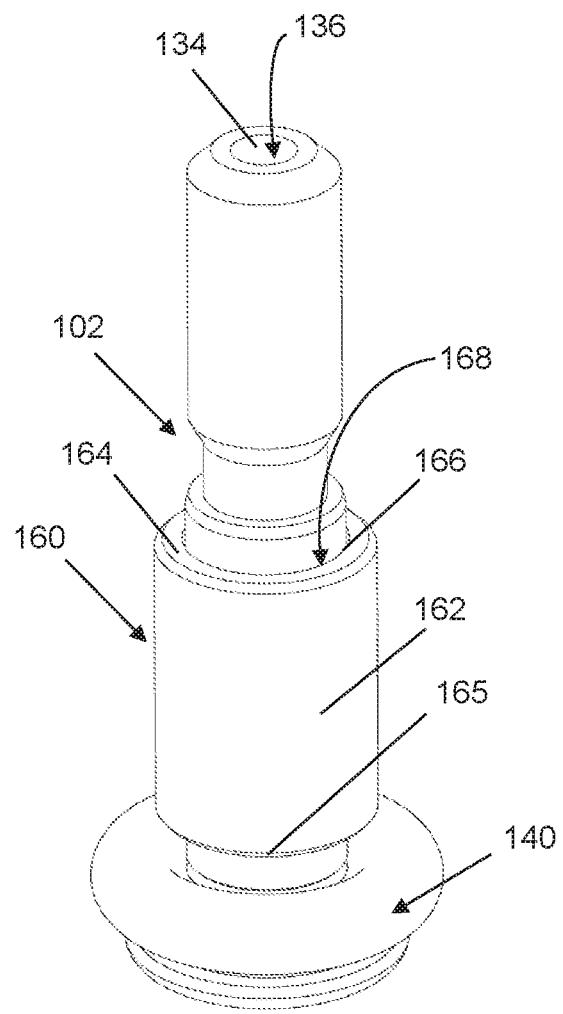
FIG. 10 is a top and side perspective view of the distal elastomeric element circumscribing a distal stem portion of the central coupler body and a cylindrical spacer circumscribing and mounted on the central body axially above the distal elastomeric element.

Referring to FIG. 10, the expanding mandrel collet coupling device 100 further comprises a spacer 160 configured to circumscribe or be integrally formed with the elongated central body member 102. As illustrated, spacer 160 comprises a cylindrical body 162 extending between a superior end 164 and an inferior end 165. The cylindrical body 162 comprises an interior circumscribing surface 166 (FIG. 15) that defines an open ended passageway 168 extending through the body 162 wherein the passageway 168 is dimensioned to closely or tightly circumscribe the lower cylindrical body member 120 of the elongated central body member 102.

Referring to FIGS. 7, 10, and 15, the spacer 160 is further configured to be circumscribed by the expanding mandrel collet 170 wherein the superior end 164 of spacer 160 abuts against the distal end of the mounting flange 36 and the inferior end 165 abuts against an interior annular shoulder stop surface 177 of a annular base portion 172 of the expanding mandrel collet 170 wherein the annular base portion 172 further comprise a distal or lower annular end 176 that mounts on the distal annular shoulder stop surface 122 of the distal cylindrical stem portion 124 (FIG. 8) of the elongated central body member 102 for securing the expanding mandrel collet 170 coaxially with the central body member 102 along the longitudinal central axis 90.

Figure 16:
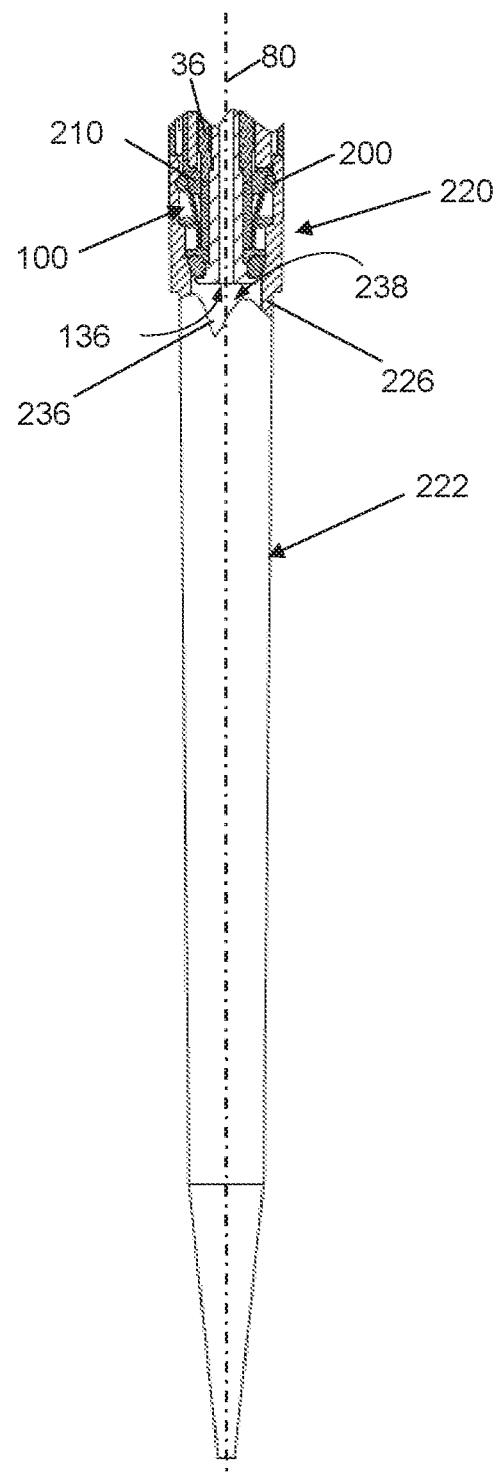
FIG. 16 is a fragmentary, partially sectional, side elevational view of the example embodiment of the disposable pipette tip operatively coupled to the pipette device by way of the embodiment of the expanding mandrel collet coupling device.

Referring to FIGS. 15 and 16, and as noted above, the shank member 108 of the expanding mandrel collet coupling device 100 is configured to fit within the distal mounting flange 36 of the aspirating and dispensing cylinder 34 for operatively coupling the expanding mandrel collet coupling device 100 to the pipette device 20 and removably coupling the disposable pipette tip 220 to the pipette device 20 by way of the expanding mandrel collet coupling device 100 such that the longitudinal channel axis 80 and central axis 90 form a coincident or common longitudinal channel axis.

Expanding Mandrel Collet 170

Figure 11:
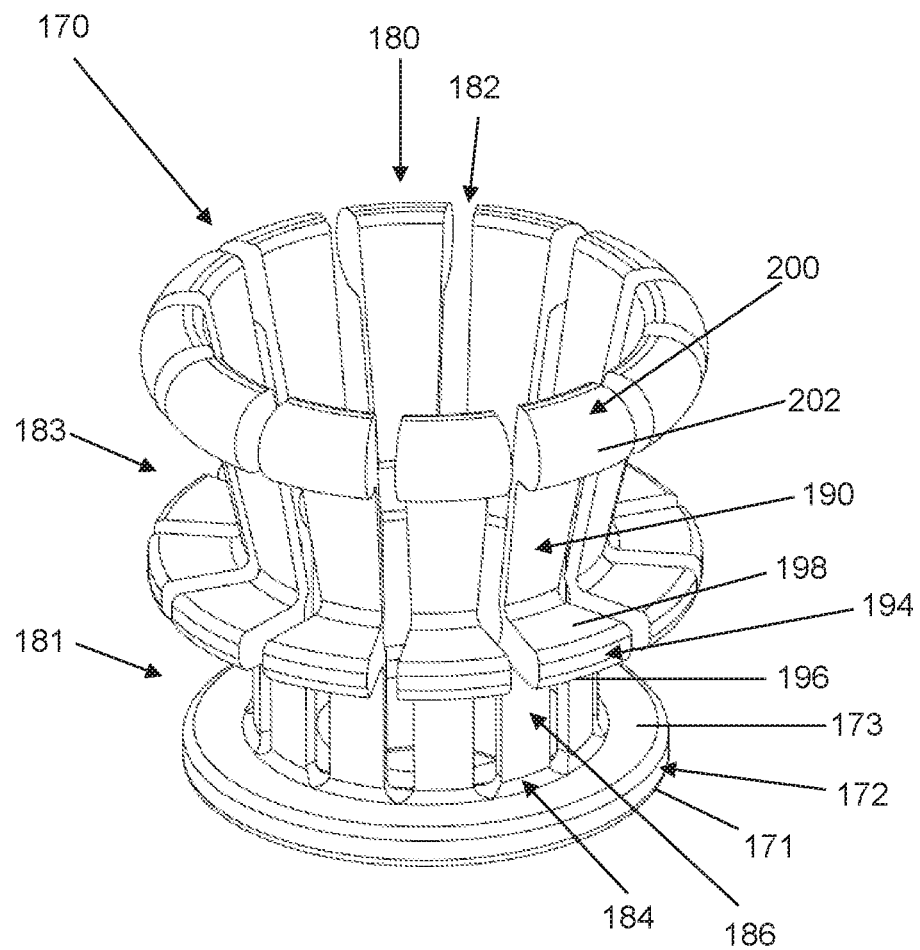
FIG. 11 is a top and side perspective view of an example embodiment of an expanding mandrel collet of the expanding mandrel collet coupling device.

Referring to FIGS. 7 and 11, the expanding mandrel collet 170 comprises a plurality of circumferentially spaced apart upwardly extending collet arms 180 transitioning upwardly from ends 184 attached to the lower annular base portion 172 to free segmented ends 200 defining the segmented collar disposed axially above the lower annular base portion 172. The plurality of circumferentially spaced apart upwardly extending collet arms 180 are separated from one another by one of a plurality of circumferentially spaced apart upwardly extending slots 182.

Figure 12:
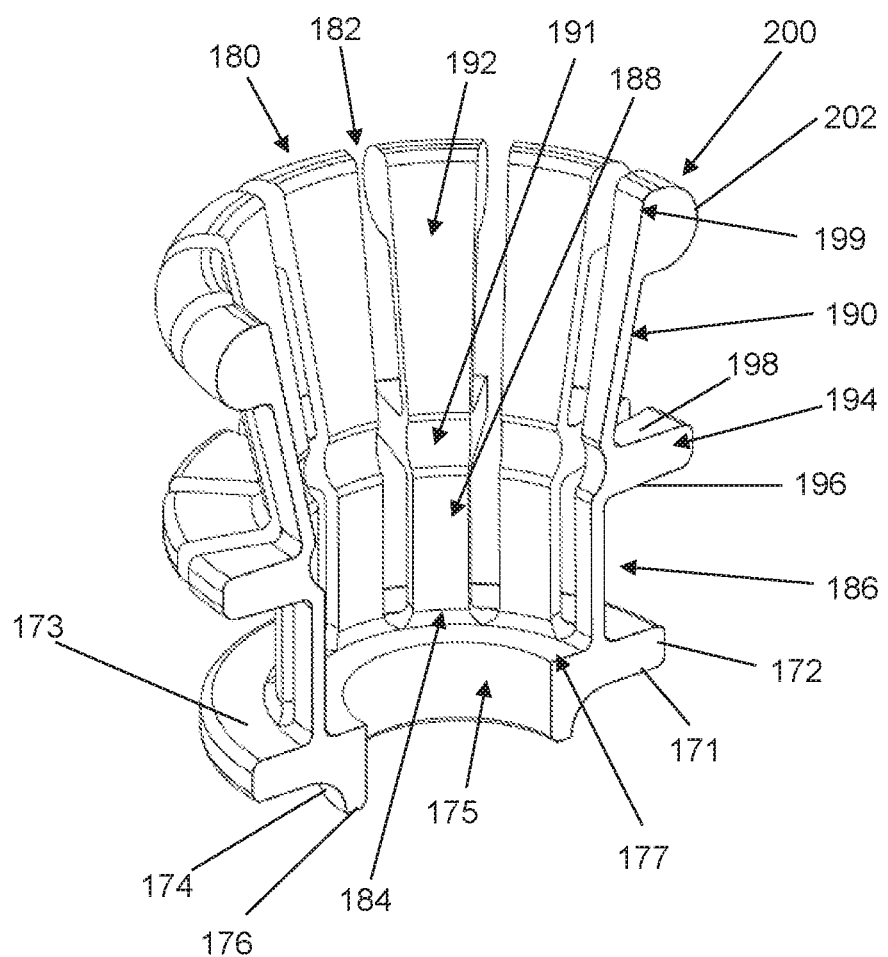
FIG. 12 is a longitudinal sectional, side perspective view of the example embodiment of the expanding mandrel collet of the expanding mandrel collet coupling device.

As illustrated in FIGS. 11 and 12, each of the plurality of upwardly extending collet arms 180 comprises a respective lower arm portion 186 transitioning into a respective upper arm portion 190. In one embodiment, the plurality of circumferentially spaced apart lower arm portions 186 form a generally cylindrically shaped circumscribing lower body portion 181 and the plurality of circumferentially spaced apart upper arm portions 190 form a frustoconically shaped circumscribing upper body portion 183 radially outwardly and upwardly transitioning from the lower body portion 181. The lower body portion 181 can be configured with a slight upward taper or increased circumference with respect the distal or lower annular base portion 172.

Base Portion 172

Figure 14:
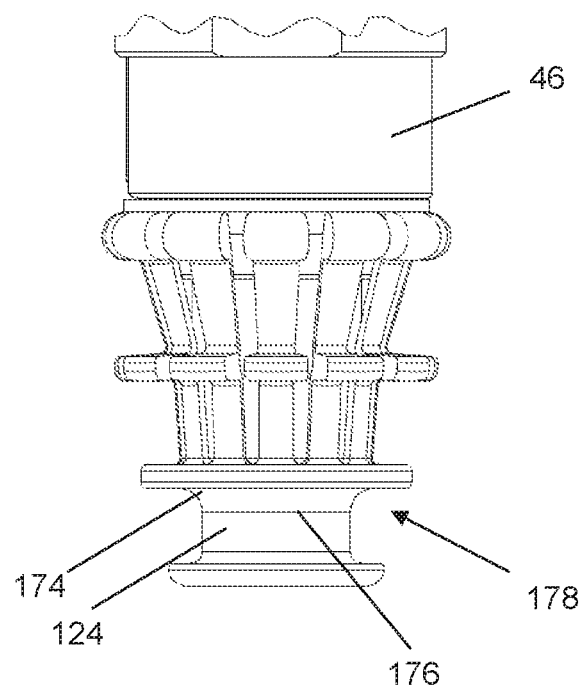
FIG. 14 is a side elevational view of the example embodiment of the expanding mandrel collet in an expanded configuration by application of a force from a piston sleeve or squeeze sleeve illustrated in fragment.

Referring to FIGS. 11 and 12, the distal or lower annular base portion 172 comprises a distally or downwardly facing base surface 171 and a proximally or upwardly facing base surface 173. The distally facing base surface 171 downwardly transitions into an abbreviated distal or lower end annular stem surface 174 that terminates to a distal or lower annular base portion end 176 of the lower annular base portion 172. The base surface 171 and base portion 172 define an abbreviated distal end annular groove 178 as illustrated in FIG. 14.

Referring to FIGS. 12 and 15, the lower annular base portion 172 further comprises an inner cylindrical surface 175 upwardly transitioning into the interior annular shoulder stop surface 177 on which spacer 160 is mounted on as illustrated in FIG. 15. Additionally, the inner cylindrical surface 175 is dimensioned with an inner diameter that closely circumscribes lower cylindrical body member 120 of central body member 102 at a location directly above the annular shoulder stop surface 122 of central body member 102 wherein the annular shoulder stop surface 122 defines the axial stop for the lower annular base portion end 176 of the expanding mandrel collet 170 such that the expanding mandrel collet 170 is centrally mounted on and about the elongated central body member 102.

Lower Arm Portions 186

As illustrated in FIG. 11, the lower arm portions 186 comprise distal or lower end portions 184 circumferentially spaced apart and attached to the lower annular base portion 172. As illustrated in FIG. 12, the lower arm portions 186 further comprise upper end portions defining medial arm portions having interior annular recessed segmented surfaces or grooves 191 and exterior radially outwardly extending annularly segmented stop disk portions 194.

Referring to FIGS. 11 and 12, the segmented stop disks 194 circumscribe and radially extend from an exterior of the medial arm portions of the plurality of circumferentially spaced apart upwardly extending collet arms 180 defining an annular segmented stop disk.

As illustrated in FIG. 12, each of the segmented stop disks 194 comprises a proximally or upwardly facing stop disk surface 198 and a distally or downwardly facing stop disk surfaces 196. Additionally, the plurality of lower arm portions 186 comprise inner cylindrical or interior segmented surfaces 188 dimensioned with an inner diameter that closely circumscribes the spacer 160 which circumscribes the elongated central body member 102.

The distal or lower end of the interior segmented surfaces 188 radially inwardly transition into the interior annular shoulder stop surface 177 that provide the stop surface for spacer 160 as detailed above. The proximal or upper end of the interior segmented surfaces 188 transition into the interior annular recessed segmented surface or groove 191.

Upper Arm Portions 190

Referring to FIGS. 11 and 12, the plurality of circumferentially spaced apart upper arm portions 190 upwardly and radially outwardly transition from the respective lower arm portions 186 and terminate into a plurality of free ends 199 disposed above and radially outwardly from the lower arm portions 186 wherein the plurality of free ends 199 comprise radially outwardly projecting segments defining segmented collar 200 wherein each segment comprises an exterior outwardly facing surface 202 which, in one embodiment is outwardly rounded or arcuate in shape corresponding to the arcuate groove of the example embodiment of the pipette tip.

Accordingly, the upper arm portions 190 upwardly and radially outwardly transition from the segmented stop disks 194 to a plurality of radially outwardly projecting segments defining segmented collar 200 wherein the segmented collar 200 is configured to circumscribe longitudinal central axis 90 of the expanding mandrel collet coupling device 100 as illustrated in FIG. 7.

Additionally, the plurality of circumferentially spaced apart radially outwardly and upwardly extending upper arm portions 190 including the segments respectively comprise interior surfaces 192 forming an inclined segmented interior surface complemental to the proximally inclined annular side surface 216 of the annular wedge 210 (FIG. 7) wherein each comprises a distally decreasing circumference relative to the Z axis and wherein the interior surfaces 192 of the upper arm portions 190 form a radially outwardly and upwardly extending conically shaped gap 204 with respect to the elongated central body member 102 (FIG. 15).

In particularly, and as illustrated in FIG. 15, the upwardly and radially outwardly inclined inner surfaces 192 of the plurality of circumferentially spaced apart upper arm portions 190 define a distally tapering cone gap 204 between the inner surfaces 192 of the upper arm portions 190 and the combination of the lower portion of the mounting flange 36 and the upper portion of spacer 160. The tapering cone gap 204 is configured to receive the lower portion of annular wedge 210 such that the annular wedge shaped or inclined exterior side surface 216 of the annular wedge 210 abuts the inner surfaces 192 of the plurality of free ends 199 supporting the projecting segments defining segmented collar 200.

Annular Wedge 210

Figure 13:
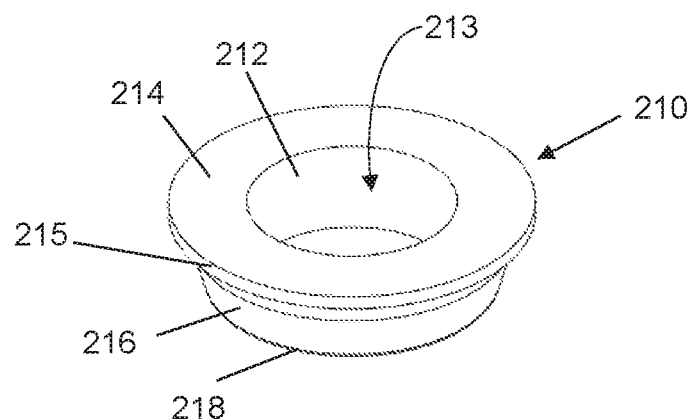
FIG. 13 is a top and side perspective view of an example embodiment of an annular wedge of the example embodiment of the expanding mandrel collet coupling device.

Referring to FIGS. 7, 13, and 15, the annular wedge 210 comprises a resilient wedge shaped annular body having a circumferentially continuous, generally wedge shaped cross section 211. The annular wedge 210 comprises a central interior annular surface 212 defining a central annular opening 213 extending through the annular wedge 210 configured to moveably circumscribe body 102.

Additionally, the annular wedge 210 comprises a top planar circular surface 214 configured to make an electrical contact switch with the LLD circuit ring end 366 of the LLD circuit 364 and radially outwardly extending from the central interior annular surface 212 to a circumscribing outer edge surface 215.

Furthermore, the annular wedge 210 comprises a radially outwardly proximally inclined side surface 216 radially upwardly and outwardly extending from a bottom annular end 218 to an underside of an annular peripheral lip 219 that radially extends outwardly and terminates to the circumscribing outer edge surface 215. Accordingly, radially outwardly proximally inclined side surface 216 defines a distally tapering wedge surface 216.

As illustrated in FIG. 15, the central annular opening 213 of the annular wedge 210 is dimensioned to allow passage of the distal mounting flange 36 and elongated tubular upper shank member 108 so as to allow a seating abutment of the radially outwardly proximally inclined side surface 216 of the annular wedge 210 with the inner surfaces 192 of the plurality of radially outwardly projecting segments 200 such that distal axial translation of annular wedge 210 results in the radial projection of the radially outwardly projecting segments 200 of the expanding mandrel collet 170 and subsequent proximal translation of annular wedge 210 results in the radial retraction of the radially outwardly projecting segments 200 of the expanding mandrel collet 170.

As further illustrated in FIG. 15, the shank member 108 of the expanding mandrel collet coupling device 100 is configured to fit within the distal mounting flange 36 of the aspirating and dispensing cylinder 34 for operatively coupling the expanding mandrel collet coupling device 100 to the pipette device 20 of the pipette device assembly 10 such that the longitudinal channel axis 80 and longitudinal central axis 90 form a coincident or common axis.

The expanding collet 170 is further configured to radially outwardly expand the segmented collar 200 from an unexpanded state having a first circumference as generally illustrated in FIG. 7 to an expanded state having a second circumference greater than the first circumference as generally illustrated in FIG. 14 when, under a force provided by the squeeze sleeve 46, the annular wedge 210 moves axially downwardly.

Actuation of Squeeze Motor

Referring to FIG. 15, the expanding mandrel collet coupling device 100 is configured to be fitted within the distal mounting flange 36 with the top planar circular surface 214 of the annular wedge 210 disposed adjacent the distal end 50 of the squeeze sleeve 46. Accordingly, and referring to FIGS. 4 and 15, the actuation of the squeeze motor 52 in the first direction results in linear axial translation of the squeeze sleeve 46 in a distal or vertically downward direction for applying a force axially on top surface 214 of the annular wedge 210 resulting in the distally tapering wedge surface 216 axially sliding down further into the cone gap 204 for forcing the distally tapering wedge surface 216 against the interior surfaces 192 of the plurality of radially outwardly projecting segments 200 for pushing the exterior radially outwardly facing surfaces 202 (FIG. 11) of the segments 200 radially outwardly against the spring tension of upwardly extending collet arms 180 and into contact with a first working surface of a pipette tip in the form of a surface 244 defining a groove 246 of the disposable pipette tip 220 as exemplified in FIG. 29 described below.

Subsequent actuation of the squeeze motor 52 in the second direction, opposite the first direction, returns the distal end 50 of the squeeze sleeve 46 to a home position illustrated in FIG. 15 such that the annular wedge member 210 axially slides up as a result the release of the stored potential energy in the upwardly extending collet arms 180 thereby resulting in the retraction of the exterior radially outwardly facing surfaces 202 of the plurality of radially outwardly projecting segments 200 from the groove 246 of the disposable pipette tip 220.

Pipette Tip 220

As illustrated in FIGS. 2 and 16, and as noted above, the expanding mandrel collet coupling device 100 provides an open communication coupling between the disposable pipette tip 220 and the pipette device 20 of the pipette device assembly 10.

Figure 17:
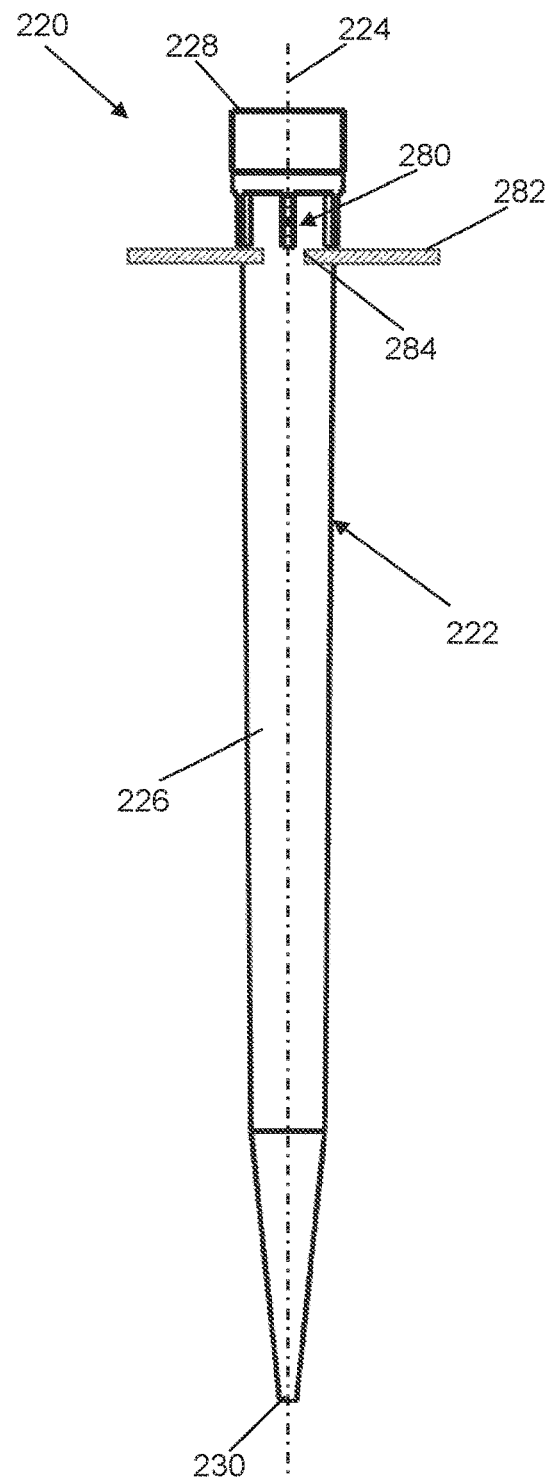
FIG. 17 is a side elevational view of the example embodiment of the disposable pipette tip illustrated in a supported position.
Figure 18:
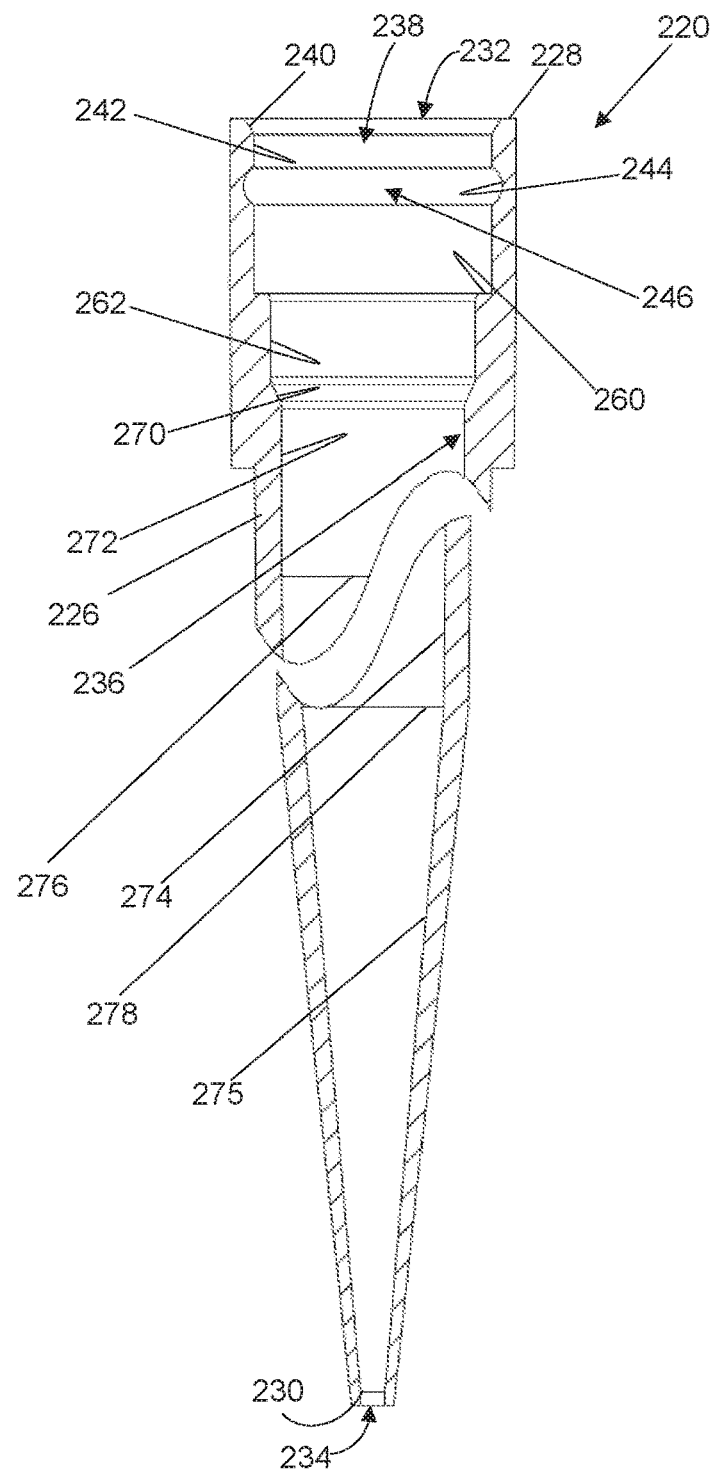
FIG. 18 is a fragmentary, longitudinal sectional, side elevational view of the example embodiment of the disposable pipette tip detailing the interior thereof.

Referring to FIGS. 16 through 18, and in one example embodiment, the disposable pipette tip 220 comprises an elongated tubular pipette tip body 222 having a central longitudinal axis 224. Pipette tip body 222 comprises an elongated circumscribing sidewall 226 longitudinally extending along the central longitudinal axis 224 between a proximal or upper annular end face 228 and a distal or lower annular end face 230 defining circumscribing open proximal and distal annular ends 232 and 234 respectively. The elongated circumscribing sidewall 226 comprises an interior surface 236 defining a pipette tip passage opening 238 extending longitudinally along the central longitudinal axis 224 of the pipette tip body 222 between the open upper annular end 232 and the open lower annular end 234.

Accordingly, the pipette tip passage opening 238 provides open communication from an area exterior to the open distal annular end 234 (FIG. 18), through the pipette tip 220, and to the pipette device channel 40 (FIG. 15) by way of the central channel 136 of the expanding mandrel collet coupling device 100 (FIG. 16) when the coupling device 100 is coupled between the pipette device 20 and the pipette tip 220. In this coupling configuration, the central longitudinal axis 224 of the pipette tip body 222 is coextensive with the longitudinal channel axis 80 of the pipette device 20.

First Interior Surface Section

Referring to FIG. 18, and in one example embodiment, the interior surface 236 of the elongated circumscribing sidewall 226 comprises an uppermost annular chamfered interior surface 240 that distally extends radially inward from the proximal annular end face 228 of the pipette tip 220 and terminates by transitioning into a first substantially cylindrical interior surface section 242 having a first diameter.

Axially Arcuate Circumferential Surface Defining a Groove

As illustrated in FIG. 18, and in one example embodiment, the first substantially cylindrical interior surface section 242 comprises an axially arcuate circumferential interior surface 244 formed into the elongated circumscribing sidewall 226 defining a circumferential annular groove 246. Annular groove 246 divides the first substantially cylindrical interior surface section 242 into an upper first substantially cylindrical interior surface portion and a lower first substantially cylindrical interior surface portion of substantially equal diameter. Accordingly, the annular groove 246 provides a circumferential radially outwardly extending concave shaped interior surface interruption of the first substantially cylindrical interior surface section 242 with an arcuate surface longitudinal cross section. The arcuate circumferential interior surface 244 is also configured in alternative surface cross sections as discussed below. And in one embodiment, the first substantially cylindrical interior surface section 242 is devoid of arcuate circumferential interior surface 244 defining the circumferential annular groove 246.

Figure 19:
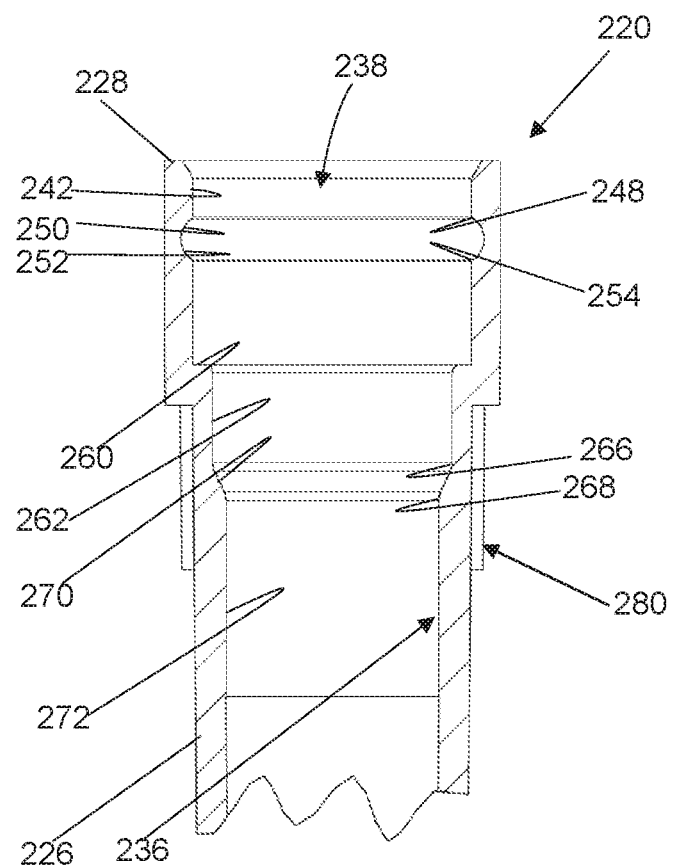
FIG. 19 is a fragmentary, longitudinal sectional, side elevational view of an upper coupling portion of the example embodiment of the disposable pipette tip detailing the upper coupling interior thereof.

Referring to FIGS. 18 and 19, the axially arcuate circumferential interior surface 244 defining the annular groove 246 comprises an upper annular transition edge 248 distally transitioning into an upper axially arcuate circumferential surface sector portion 250 of the axially arcuate circumferential interior surface 244. In succession, the upper axially arcuate circumferential surface sector portion 250 distally transitions into a lower axially arcuate circumferential surface sector portion 252 of the axially arcuate circumferential surface 244. Then, lower axially arcuate circumferential surface sector portion 252 terminates to a lower annular transition edge 254.

The upper axially arcuate circumferential surface sector portion or upper portion 250 provides the annular groove 246 with an increasing radius relative to the central longitudinal axis 224 (FIG. 17) of the pipette tip 220 from the upper annular transition edge 248 to a maximum radius of the annular groove 246 relative to the central longitudinal axis 224 that defines a circumferential annular center of the annular groove 246. The lower axially arcuate circumferential surface sector portion or lower portion 252 provides the annular groove 246 with a decreasing radius relative to the central longitudinal axis 224 of the pipette tip 220 from the maximum radius defining the circumferential annular center of the of the annular groove 246 to the lower annular transition edge 254.

Second Interior Surface Section and Annular Shoulder Stop Surface

As illustrated in FIG. 18, the first substantially cylindrical interior surface section 242 is axially distally proceeded by a second substantially cylindrical interior surface section 262 having a second diameter less than the first diameter of the first substantially cylindrical interior surface section 242 for forming a proximally facing, radially inwardly extending annular shoulder seat surface or axial stop surface 260 interposed between the first and second substantially cylindrical interior surface sections 242, 262.

In one example embodiment, the proximally facing axial stop surface 260 is substantially planar and generally perpendicular to the central longitudinal axis 224 of the pipette tip body 222 as illustrated in FIG. 17.

Third Interior Surface Section and Sealing Seat

As also illustrated in FIGS. 18 and 19, the second substantially cylindrical interior surface section 262 is axially distally proceeded by a third substantially cylindrical interior surface section 272 having a third diameter less than the second diameter of section 262.

Interposed between the second section 262 and the third section 272 is a frustoconical annular sealing seat or stop surface 270 defining a circumferential radially inwardly angled and distally extending distal working surface 270. The frustoconical annular sealing seat surface 270 comprises an upper annular sealing seat edge 266 defining an annular border between the second substantially cylindrical interior surface section 262 and the frustoconical annular sealing seat surface 270. In addition, the frustoconical annular sealing seat surface 270 comprises a lower annular sealing seat edge 268 defining an annular border between the frustoconical annular sealing seat surface 270 and the third interior surface section 272 wherein a diameter of the upper annular sealing seat edge 266 is greater than a diameter of the lower annular sealing seat edge 268.

Accordingly, the frustoconical annular sealing seat surface 270 defines the circumferential radially inwardly angled and distally extending second working surface or sealing seat surface 270 interposed between the second substantially cylindrical interior surface section 262 and the third substantially cylindrical interior surface section 272.

Figure 41:
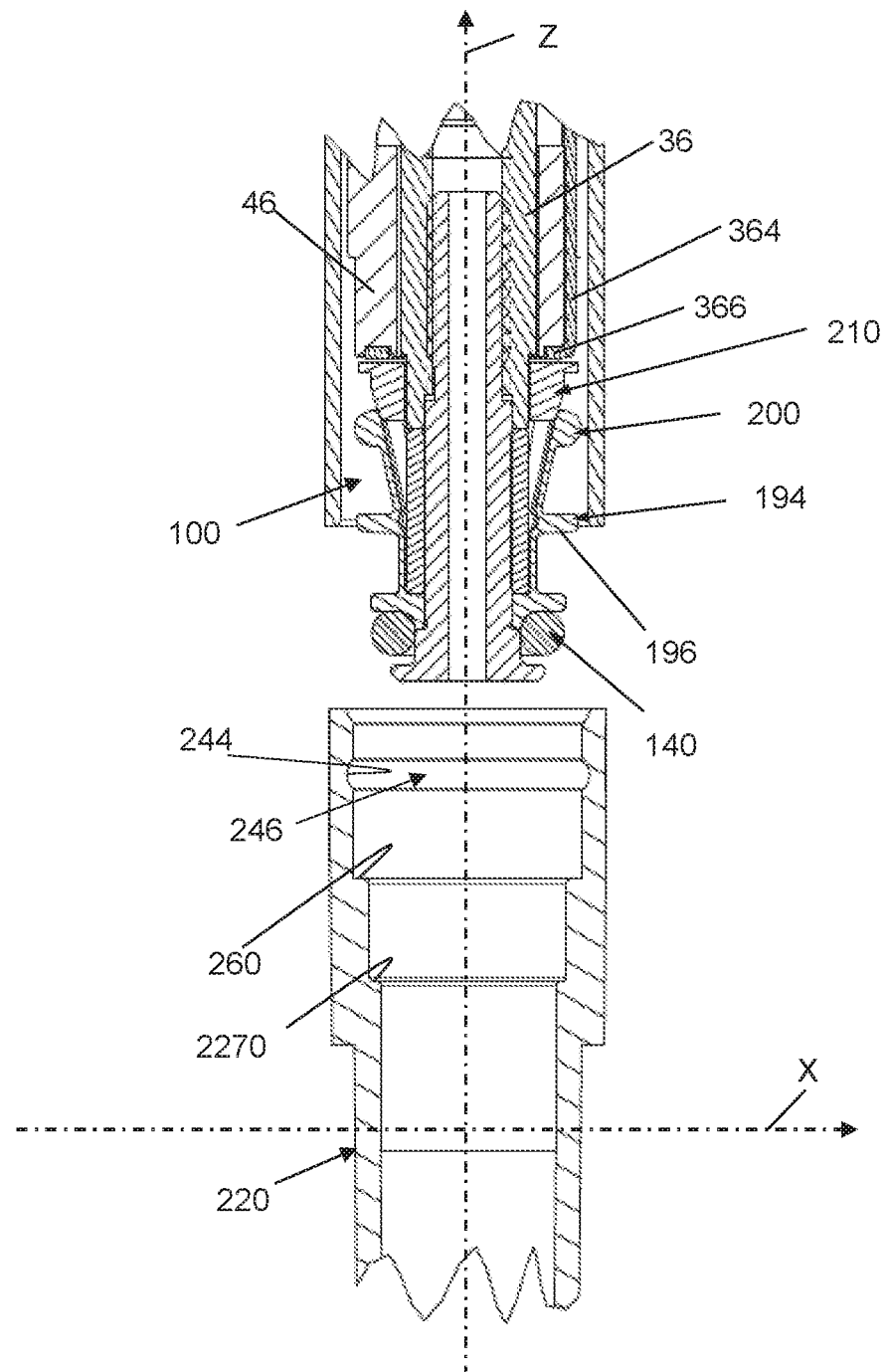
FIG. 41 is a fragmentary, longitudinal sectional, side elevational view of the example embodiment of the expanding mandrel collet coupling device positioned over the example embodiment of the disposable pipette tip comprising an alternative sealing seat surface angle of substantially ninety degrees relative to the central longitudinal axis of the pipette tip.

As illustrated, the sealing seat surface 270 is disposed at an acute angle relative to the central longitudinal axis 224 wherein the acute angle defines an acute sealing seat surface angle relative to the central longitudinal axis 224 (FIG. 17). In one embodiment, the preferred acute sealing seat surface angle relative to the central longitudinal axis 224 is about 15 degrees to about 35 degrees with a preferred angle of about twenty-five degrees. As illustrated in FIG. 41, the acute sealing seat surface angle of an alternative sealing seat surface 2270 relative to the central longitudinal axis 224 is about 90 degrees.

Lower Interior Surface Portion

FIG. 18 further illustrates that in succession to the third substantially cylindrical interior surface section 272 is a fourth interior surface section 274 that is distally followed by a fifth interior surface section 275.

In one example embodiment, the fourth interior surface section 274 distally tapers or decreases in diameter from a distal annular end 276 of the third substantially cylindrical interior surface section 272 to a proximal annular end 278 of the fifth interior surface section 275. In turn, the fifth interior surface section 275 distally tapers or decreases in diameter from the proximal annular end 278 of the fifth interior surface section 275 to the open distal annular end 234 of the pipette tip 220 that is intended for immersion. Additionally, and in one example embodiment, the fifth interior surface section 275 has a greater taper than the fourth interior surface section 274.

External Longitudinal Ribs

Referring to FIG. 17, one example embodiment of the pipette tip 220 comprises a plurality of circumferential spaced apart longitudinally extending external ribs 280 disposed on the tubular pipette tip body 222 adjacent the periphery of the proximal annular end face 228 and longitudinally extending externally therefrom to an exterior area of the circumscribing sidewall 226 that is adjacent to the third substantially cylindrical interior surface section 272 as illustrated in FIG. 18.

In one example embodiment, the plurality of circumferential spaced apart longitudinally extending external ribs 280 may be utilized to provide support for the pipette tip 220 on or in a support surface 282 through which the pipette body 222 has passed via, for example, a support surface aperture opening 284. One example embodiment of the support surface 282 can be in the form of, but not limited to, lab ware in the form of a tip rack as is known in the art, and informed by the present disclosure.

Automated Pipetting Workstation or System

Figure 20:
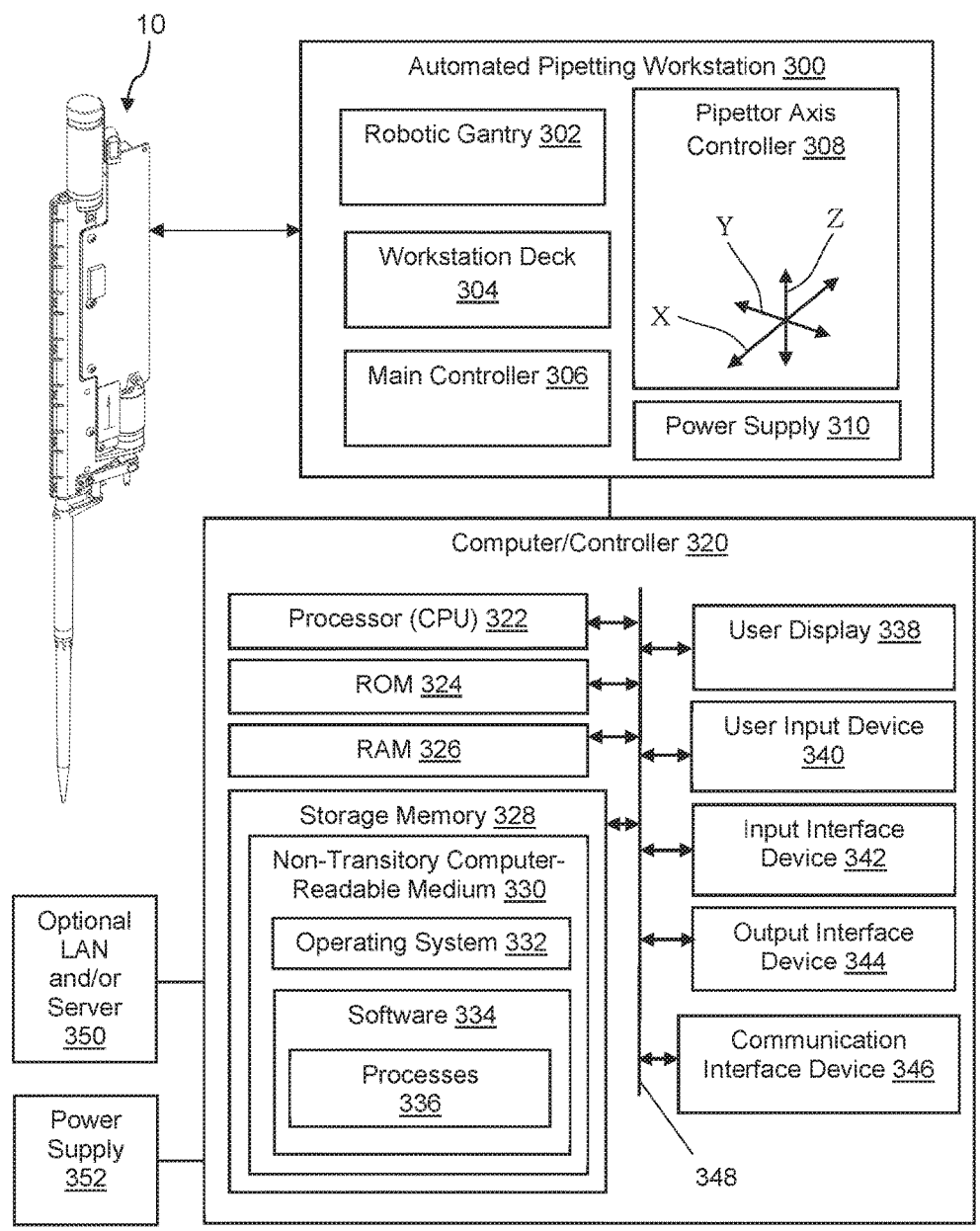
FIG. 20 diagrammatical block diagram view of an example embodiment of an automated pipetting workstation or system.

Referring to FIGS. 5 and 20, and in one example of use and operation, one or more of the pipette device assemblies 10 is employed in an automated pipetting workstation or system 300 that generally provides, but is not limited to, programmed transfers of liquid between containers which comprises mounting and ejection processes of one or more disposable pipette tips 220 to the expanding mandrel collet coupling device 100 operatively carried by the pipette device 20 for carrying out, for example, the programmed transfers of liquid between containers.

In one example embodiment, the automated pipetting workstation 300 generally comprises a robotic gantry 302 that carries at least one pipette device assembly 10 vertically above a horizontally disposed workstation deck 304. The pipette device assembly 10 can comprise a single channel pipetting head or a multi-channel pipetting head.

Additionally, the robotic gantry 302 typically provides two or three degrees of freedom wherein three degrees of freedom comprises longitudinal translation along an axis defining an X-axis, latitudinal translation along an axis defining a Y-axis, and vertical (up and down) translation along an axis defining a Z-axis so that the pipette device assembly 10 can move along the length (X-axis) and width (Y-axis) of the deck and vertically up and down (Z-axis) relative thereto. With two degrees of freedom, the robotic gantry is typically provided with the ability to translate the pipette device assembly 10 vertically and either longitudinally or laterally.

In one example embodiment, the automated pipetting workstation 300 further comprises a main controller 306, a pipette axis controller 308, and a power supply 310 that provides power for the main controller 306, the pipette axis controller 308, and the pipette device assembly 10.

Additionally, and in one example embodiment, a computer/controller 320 can also be employed with the workstation 300 and communicate with the main controller 306 and the pipette axis controller 308 for controlling the robotic gantry 302 and pipette device assembly 10 including the associated process protocols of the pipette device assembly 10 such as the disposable pipette tip 220 attaching and ejection (coupling and decoupling) processes detailed below.

In one example embodiment, the computer/controller 320 typically comprises a processor device or central processing unit (CPU) 322, a hardware read only memory device (ROM) 324, a hardware main memory device (RAM) 326, a hardware storage memory 328 comprising a non-transitory computer readable medium or memory 330 having an operating system 332 and software 334 such as user defined processes 336 for the pipette device assembly 10 stored thereby, a user display 338, a user input device 340, an input interface 342, an output interface 344, a communication interface device 346, and a system bus 348 which comprises one or more conductor or communication paths that permit communication among the devices of the computer/controller 320. Computer/controller 320 may also be operatively couple to LAN and/or server 350. A power supply 352 provides power for the computer/controller 320.

Examples of the above delineated automated pipetting workstation 300 including software are presently manufactured and sold by Hamilton Company, the assignee of the present patent application, located at 4970 Energy Way, Reno, Nev. 89502, United States of America.

Pipette Tip Pickup Process with Expanding Mandrel Collet Coupling Device

FIGS. 21 through 31 illustrate details of an example embodiment of successive stages of a pipette tip pickup process and, in particular, a method of securing attachment of the pipette tip 220 to the expanding mandrel collet coupling device 100 operatively carried by the pipette device 20. As noted above, and in one example embodiment, the pipette tip 220 may be supported by a support surface 282.

As illustrated in FIG. 21, the expanding mandrel collet coupling device 100 is connected to the pipette device 20, and upon command, the coupling device 100 is positioned over the open proximal end 232 of the pipette tip 220 wherein each of their respective central longitudinal axis is aligned along the Z-axis. The eject sleeve 62 is in the eject position, the squeeze sleeve 46 is in the unsqueezed position, the expanding mandrel collet 170 is in the relaxed state, and the distal O-ring 140 is in the unsqueezed state.

Figure 22:
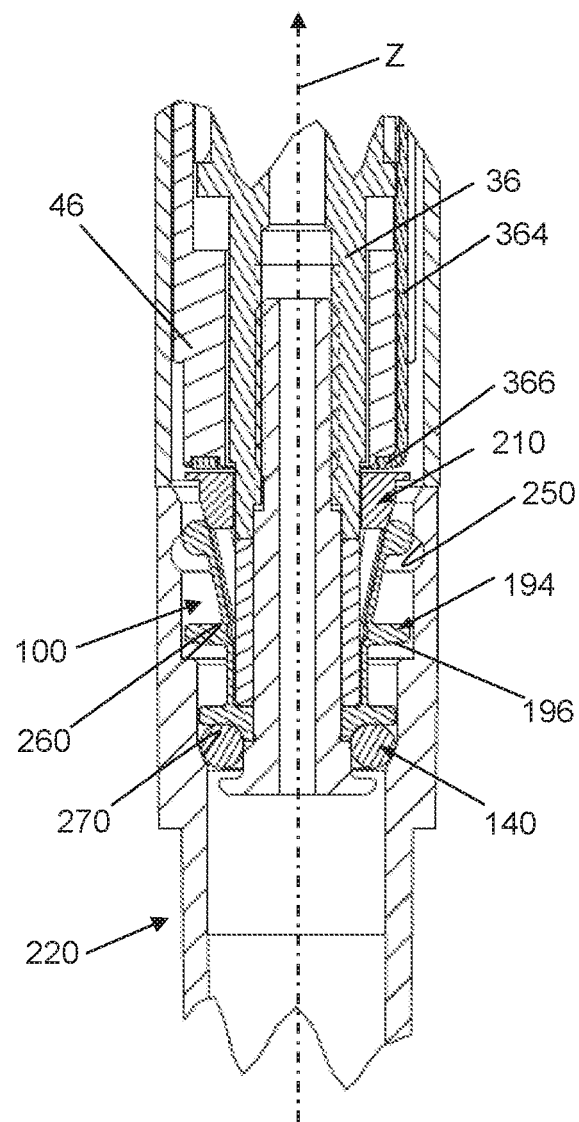
FIG. 22 is a fragmentary, longitudinal sectional, side elevational view of the example embodiment of the expanding mandrel collet coupling device positioned over and into the disposable pipette tip defining a coupling stage with the distal elastomeric element initially contacting a sealing seat surface of the pipette tip and with the plurality of discrete coupling elements or segments in an unsqueezed or radially outwardly unextended state, the sealing seat surface having an acute sealing seat surface angle relative to the central longitudinal axis of the pipette tip.

Next, FIG. 22 illustrates the expanding mandrel collet coupling device 100 being moved down along the Z-axis into the pipette tip 220 for lowering the distal, elastomeric carrying portion of the coupling device 100 to pass into the interior cylindrical proximal end portions of the pipette tip 220 to bring the distal O-ring 140 into contact with the annular sealing seat or stop surface 270 of the tip 220 while maintaining the distal O-ring 140 in the unsqueezed state and before the upwardly facing annular shoulder seat or stop surface 260 of the pipette tip 220 and the downwardly facing axial stop disk surface 196 of the stop disk 194 are mated.

Figure 23:
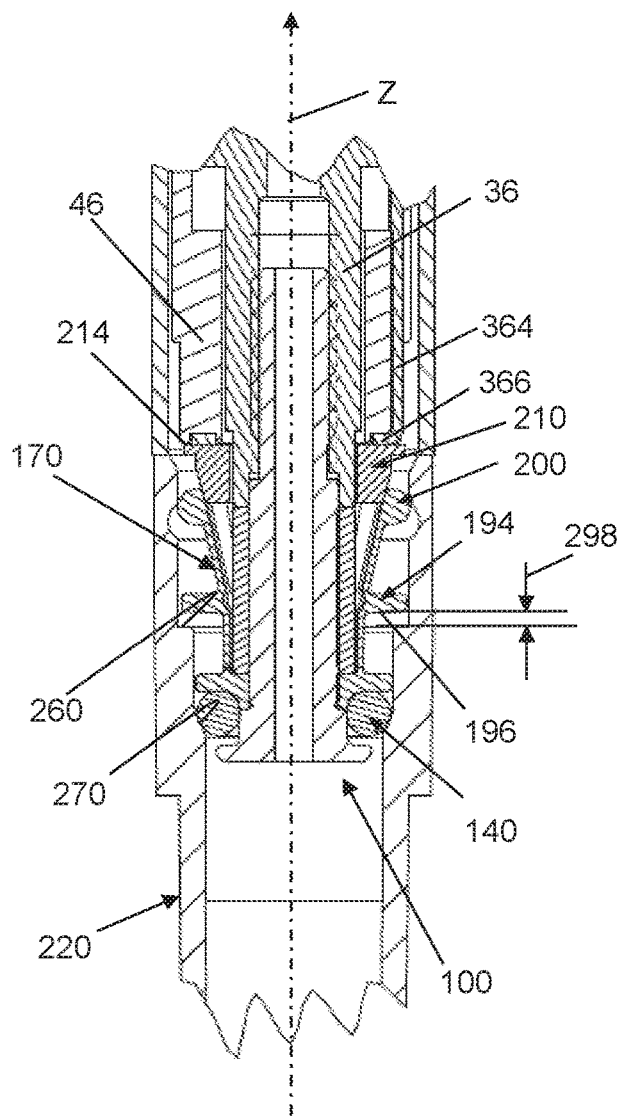
FIG. 23 is a fragmentary, longitudinal sectional, side elevational view of the example embodiment of the expanding mandrel collet coupling device and pipette tip with the pipette tip being lifted as a result of the piston sleeve pushing down on the annular wedge for radially extending a rounded part of a plurality of expanding mandrel collet segments against an upper corner of a groove formed in the pipette tip resulting in an axial force that lifts or pulls the pipette tip up which starts the process of seating the pipette tip and compressing the distal elastomeric element against the sealing seat surface of the pipette tip.
Figure 24:
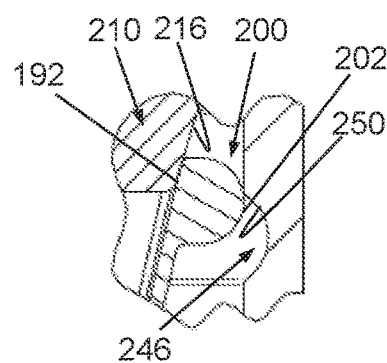
FIG. 24 is a fragmentary, longitudinal sectional, side elevational detailed view of the rounded surface of one of the plurality of expanding mandrel collet segment arms of the expanding mandrel collet of the segmented coupler being extended into contact with the corner of the groove of the pipette tip as is illustrated in FIG. 23.
Figure 25:
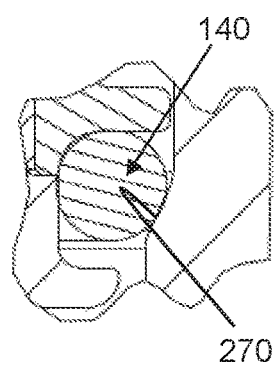
FIG. 25 is a fragmentary, longitudinal sectional, side elevational detailed view of the distal elastomeric element in an initial compressed state against the sealing seat surface of the pipette tip as is illustrated in FIG. 23.

Next, FIG. 23 illustrates the coupling device 100 being further moved down along the Z-axis. Additionally, and referring to FIGS. 23 through 25, the squeeze sleeve 46 is moved down along the Z-axis and pushes against the LLD circuit ring end 366 which contacts with and pushes against the top surface 214 of the annular wedge 210 that surmounts the expanding mandrel collet 170 while maintaining the plurality of radially outwardly projecting segments 200 in the unexpanded state as detailed in FIG. 24, maintaining the distal O-ring 140 in the uncompressed state as detailed in FIG. 25, and before the stop surface 260 of the pipette tip 220 and the axial stop shoulder surface 196 of the stop disk 194 are mated such that a gap 298 is maintained between the stop surface 260 of the pipette tip 220 and the axial stop shoulder surface 196 of the stop disk 194 of the expanding mandrel collet 170 as detailed in FIG. 23.

Figure 26:
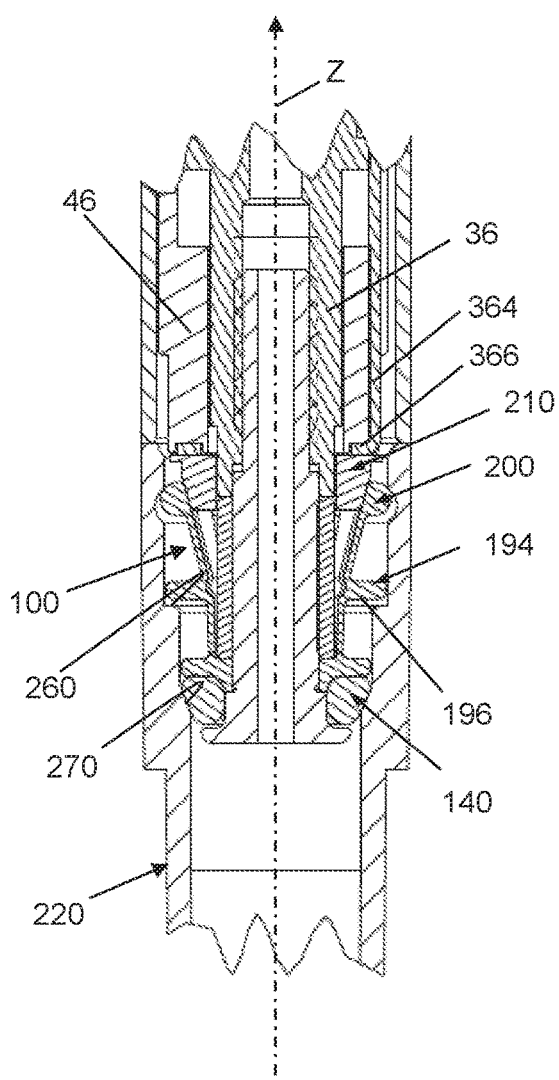
FIG. 26 is a fragmentary, longitudinal sectional, side elevational view of the example embodiment of the expanding mandrel collet coupling device positioned yet further into the pipette tip with the pipette tip being lifted while the piston sleeve further forces down on the annular wedge to continue radially extending the rounded surface of the plurality of expanding mandrel collet segments into the groove of the pipette tip further pulling the pipette tip up and further compressing the distal elastomeric element against the sealing seat surface of the pipette tip.
Figure 27:
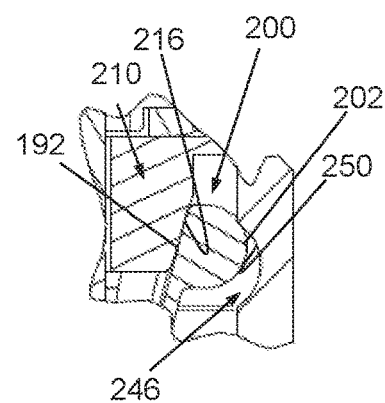
FIG. 27 is a fragmentary, longitudinal sectional, side elevational detailed view of the rounded surface of one of the plurality of expanding mandrel collet segments being further extended into the groove of the pipette tip as is illustrated in FIG. 26.
Figure 28:
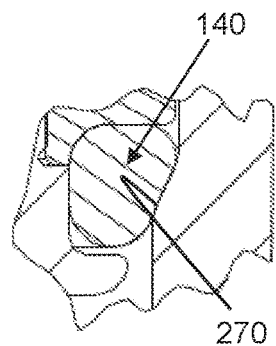
FIG. 28 is a fragmentary, longitudinal sectional, side elevational detailed view of the distal elastomeric element being further compressed from the initial compressed state against the sealing seat surface of the pipette tip as is illustrated in FIG. 26.

Next, FIG. 26 illustrates the squeeze sleeve 46 being moved further down along the Z-axis for pushing the annular wedge 210 against the interior surface 192 of the plurality of radially outwardly projecting segments 200 for pushing them radially outwardly out and abutting the exterior radially outwardly facing rounded surfaces 202 of the plurality of radially outwardly projecting segments 200 against the upper axially arcuate circumferential surface sector portion 250 of the groove 246 of the disposable pipette tip 220 as detailed in FIG. 27 for starting the process of squeezing or pushing the plurality of radially outwardly projecting segments 200 into the groove 246 and initially into abutment with the upper axially arcuate circumferential surface sector portion 250 of the axially arcuate circumferential interior surface 244 defining the groove 246. As illustrated in FIG. 26, the action of the plurality of radially outwardly projecting segments 200 extending or being projected into the groove 246 as detailed in FIG. 27 causes an axial upward force that starts the process of pulling the pipette tip 220 up for starting a process of seating the annular shoulder seat surface 260 of the pipette tip 220 with the axial stop shoulder surface 196 of the stop disk 194 for closing the gap 298 (FIG. 23) and compressing the distal O-ring 140 with the sealing seat or stop surface 270 of the tip 220 as detailed in FIG. 28.

FIG. 29 illustrates the squeeze sleeve 46 being moved down along the Z-axis a configured predetermined length until it is locked in position resulting in the annular wedge 210 being stopped and locked in position by the squeeze sleeve 46.

Figure 30:
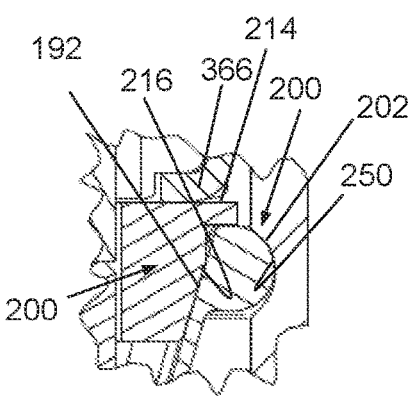
FIG. 30 is a fragmentary, longitudinal sectional, side elevational detailed view of the rounded surface of one of the plurality of expanding mandrel collet segments being extended into abutment with the surface defining the groove as is illustrated in FIG. 29.

As a result, the plurality of radially outwardly projecting segments 200 are radially extended to a desired distance or value as exemplified in FIG. 30 for fully seating the axial stop shoulder surface 196 of the expanding mandrel collet coupling device 100 against the annular shoulder seat surface 260 of the pipette tip 220 with the seating of the two surfaces 196, 260 being along an X-axis substantially perpendicular to the Z-axis for forming a normal datum between the two axes.

Figure 31:
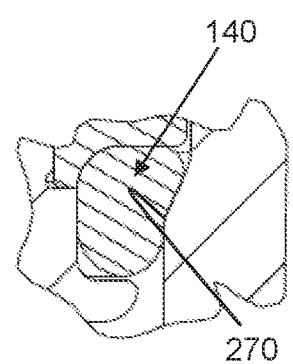
FIG. 31 is a fragmentary, longitudinal sectional, side elevational detailed view of the distal elastomeric element in the final compressed seated sealing state against the sealing seat surface of the pipette tip as is illustrated in FIG. 29.

Concurrently, the distal O-ring 140 is compressed to a desired distance or value as exemplified in FIG. 31 for seating the distal O-ring 140 with the annular sealing seat surface 270 of the tip 220 such that its cross-section is in its final compressed non-circular form thereby completing the coupling of securing the attachment of the pipette tip 220 with the expanding mandrel collet coupling device 100 operatively carried by the pipette device 20.

Upon completion of the above detailed securing attachment process, the plurality of radially outwardly projecting segments 200 and the distal elastomeric element 140 work in combination to produce a segment and seal coupling that provides a fluid-tight seal wherein the plurality of radially outwardly projecting segments 200 are at least partially received within the circumferential groove 246 and at least partially seated on the circumferential arcuate interior surface 244 (FIG. 18) defining the circumferential groove 246 and wherein the distal elastomeric element 140 seals against the surface 270 of the pipette tip 220 wherein in one embodiment surface 270 provides a radially inwardly angled and distally or downwardly extending surface.

Accordingly, the plurality of radially outwardly projecting segments 200 move radially outward to engage the circumferential groove 246 (FIG. 18) to couple with the tip 220 and move radially inward for releasing the tip 220 as a function of movement of the annular wedge 210. Applying a force for moving the annular wedge 210 axially downwards results in the plurality of radially outwardly projecting segments 200 being urged to a radially outward position and releasing the force on the annular wedge 210 results in a release of energy from the cantilevered arms 180 (FIG. 11) supporting the plurality of radially outwardly projecting segments 200 such that the segments spring back from the radially outward position to the radially inward position.

Disposable Pipette Tip Ejection Process

Figure 34:
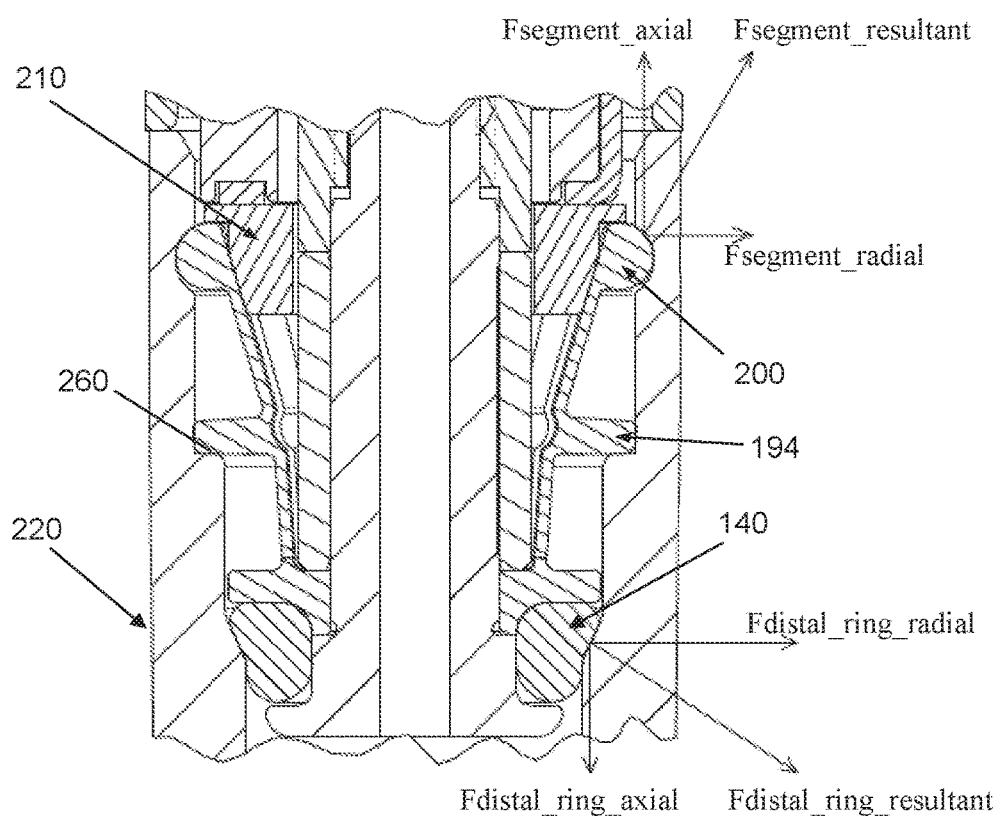
FIG. 34 is a fragmentary, longitudinal sectional, side elevational, detailed view of the completed coupling state between the example embodiments of the expanding mandrel collet coupling device and disposable pipette tip with an illustration of associated forces.

FIGS. 21 through 31 illustrate, in reverse, details of successive stages of an example method or process of ejecting the pipette tip 220 from the expanding mandrel collet coupling device 100 operatively carried by the pipette device 20. This tip ejection process sequence is similar to the attachment or tip pickup securing process sequence except in reverse and FIG. 34 illustrates a distal O-ring axial force component of the compressed distal O-ring 140 that provides a force to help remove the tip 220 during the ejection process.

In one example embodiment, the ejection process comprises the steps of: (1) positioning the tip where it is to be discarded, such as a waste container; (2) moving the squeeze sleeve 46 upward wherein force is released from the annular wedge 210 and, as a result, this force is also released from the plurality of radially outwardly projecting segments 200 so as to allow retraction from the groove 246 in the tip 220, the distal O-ring 140 starts to release stored elastic potential energy or spring energy as a force against the tip 220, and wherein the spring loaded eject sleeve 62 also pushes against the tip 220 to push it off such that the tip begins to release from the plurality of radially outwardly projecting segments 200; (3) continuing the movement of the squeeze sleeve 46 upward wherein the plurality of radially outwardly projecting segments 200 continue to retract from the groove 246 in the tip 220 and wherein the distal O-ring 140 and the spring loaded eject sleeve 62 pushes against the tip 220 to push it off wherein the tip 220 continues to release from the plurality of radially outwardly projecting segments 200; and (4) further continuing the movement of the squeeze sleeve 46 to its upmost position wherein the plurality of radially outwardly projecting segments 200 return to their original retracted free state and are completely free of the groove 246 in the tip 220 and wherein the distal O-ring 140 returns to its original shape and the spring loaded eject sleeve 62 pushes against the tip 220 until the tip is pushed off of the coupler 100 by the spring loaded eject sleeve 62 and the spring loaded eject sleeve 62 becomes fully extended.

In light of the foregoing, those skilled in the art will appreciate that these tip mounting and ejection processes are applicable to a wide range of mechanically and/or automatically driven pipette types and designs.

Coupling and Ejection Forces

Figure 32:
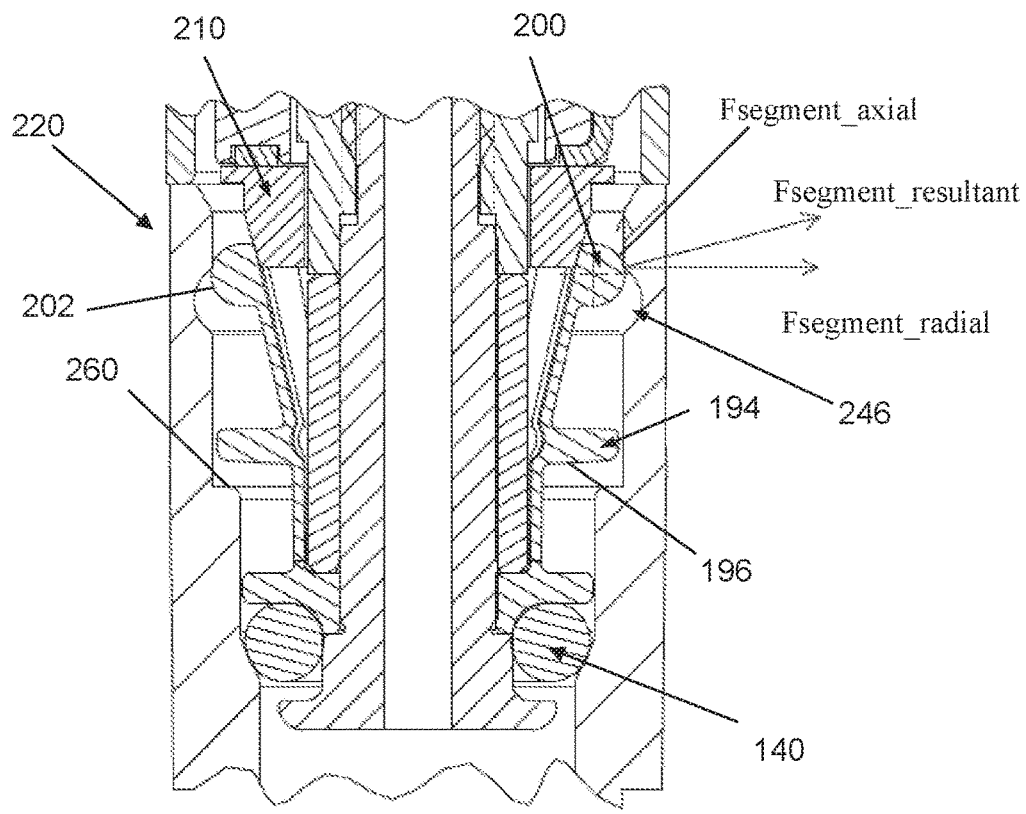
FIG. 32 is a fragmentary, longitudinal sectional, side elevational, detailed view of onset of a coupling between the example embodiments of the expanding mandrel collet coupling device and disposable pipette tip with an illustration of associated forces.

FIG. 32 illustrates a diagrammatical vector diagram of a plurality of radially outwardly projecting segments 200 of the expanding mandrel collet coupling device 100 initially extending into the groove 246 with radially rounded surface 202 of the plurality of radially outwardly projecting segments 200 contacting the upper corner of the tip groove above the center of the segment radius resulting in an axial upward force pulling the pipette tip 220 upward. As illustrated in FIG. 32, the segment force (Fsegment_resultant) for each of the plurality of radially outwardly projecting segments 200 is comprised of two components: an axial force (Fsegment_axial) component and a radial force (Fsegment_radial) component.

As long as the plurality of radially outwardly projecting segments 200 are contacting the upper corner of the tip groove above the center of the segment radius (dimension Z in FIG. 33) Fsegment_axial increases as the distance between the center of the segment radius and corner of the groove increases. Accordingly, at the beginning of the tip pickup process, the segment axial force (Fsegment_axial) starts out low as illustrated in FIG. 32 and, in detail in FIG. 33, and increases to its maximum at the end of the tip pickup process as illustrated in FIG. 34.

Figure 33:
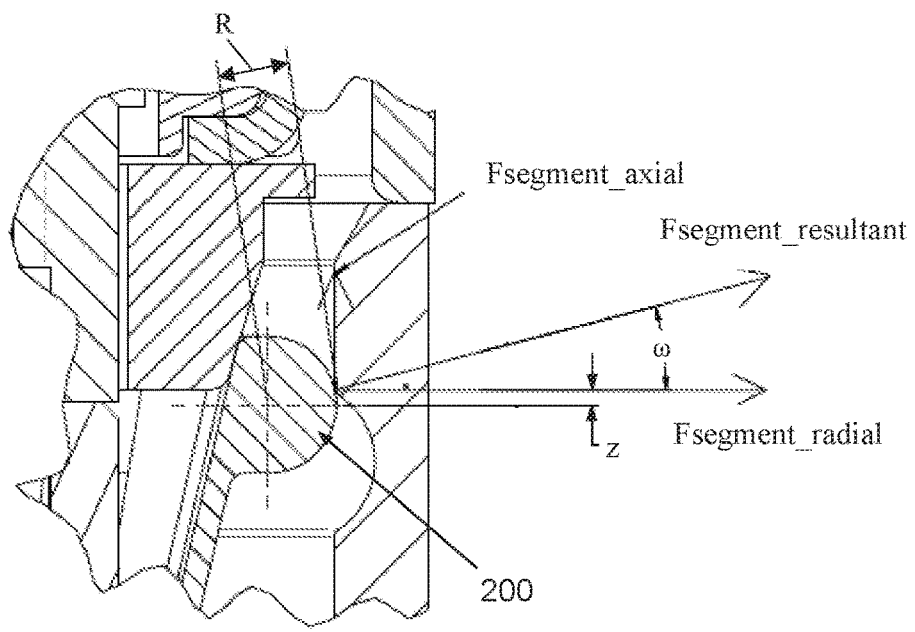
FIG. 33 is a fragmentary, longitudinal sectional, side elevational, detailed view of the onset of coupling of one of a plurality of arcuate or rounded segment surfaces of one of the plurality of expanding mandrel collet segments with the groove of the example embodiment of the disposable pipette tip with an illustration of associated forces.

Referring to FIG. 33, the ratio of Z/R equals SIN (ω) and SIN (ω) is equal to (Fsegment_axial)/(Fsegment_resultant). As a result, (Fsegment_axial) is equal to (Fsegment_resultant) multiplied by the ratio of Z/R. From this, the result is that (Fsegment_axial) increases as Z increases.

Referring to FIG. 34, the segment axial force (Fsegment_axial) seats the stop disc 194 against the seat 260 of the tip 220 and provides the force required to overcome an O-ring axial force (Fdistal_ring_axial) and compress the distal O-ring 140. The O-ring 140 has an O-ring force (Fdistal_ring_resultant) that results from being compressed and this O-ring force comprises two components: an axial component (Fdistal_ring_axial) and a radial component (Fdistal_ring_radial). Additionally, the segment radial force (Fsegment_radial) provides the radial force needed to lock the segment into the tip groove 246 (FIG. 18) and the distal O-ring radial force component (Fdistal_ring_radial) provides the radial force needed to maintain the seal against the tip. Furthermore, the segment to tip groove geometry that causes Fsegment_axial to increase as the segment enters the groove (increasing dimension Z) helps to overcome the O-ring axial force (Fdistal_ring_axial) so that the distal O-ring 140 can be completely compressed to the desired extent. Moreover, the distal O-ring axial force component (Fdistal_ring_axial) provides force to help remove the tip 220 during the ejection process.

Alignment/Misalignment

The axial shoulder surface 196 of coupler 100 and the axial shoulder seat 260 of tip 220 are important for correct tip alignment. Accordingly, the coupler 100 and tip 220 are configured so that plurality of radially outwardly projecting segments 200 push the axial shoulder surface 196 and the axial shoulder seat 260 together to preclude misalignment because if the shoulders are not properly mated, especially if they are tilted, the misalignment error (E) may be significant.

Figure 35:
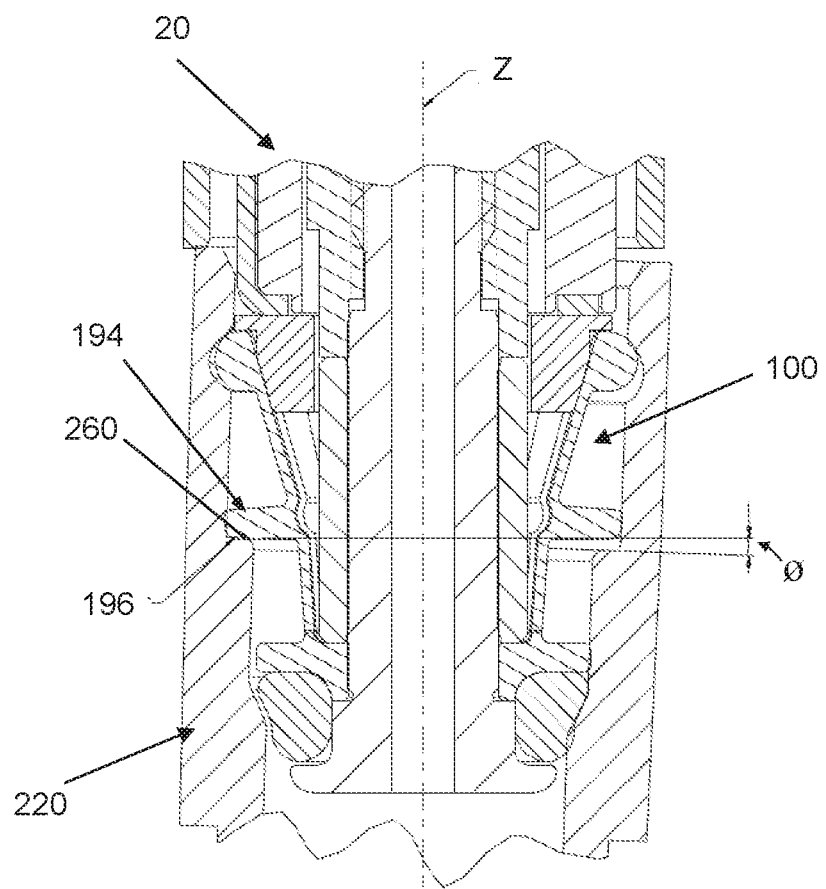
FIG. 35 is a fragmentary, longitudinal sectional, side elevational view illustrating a misaligned coupling between example embodiments of an expanding mandrel collet coupling device and disposable pipette tip for defining misalignment parameters.
Figure 36:
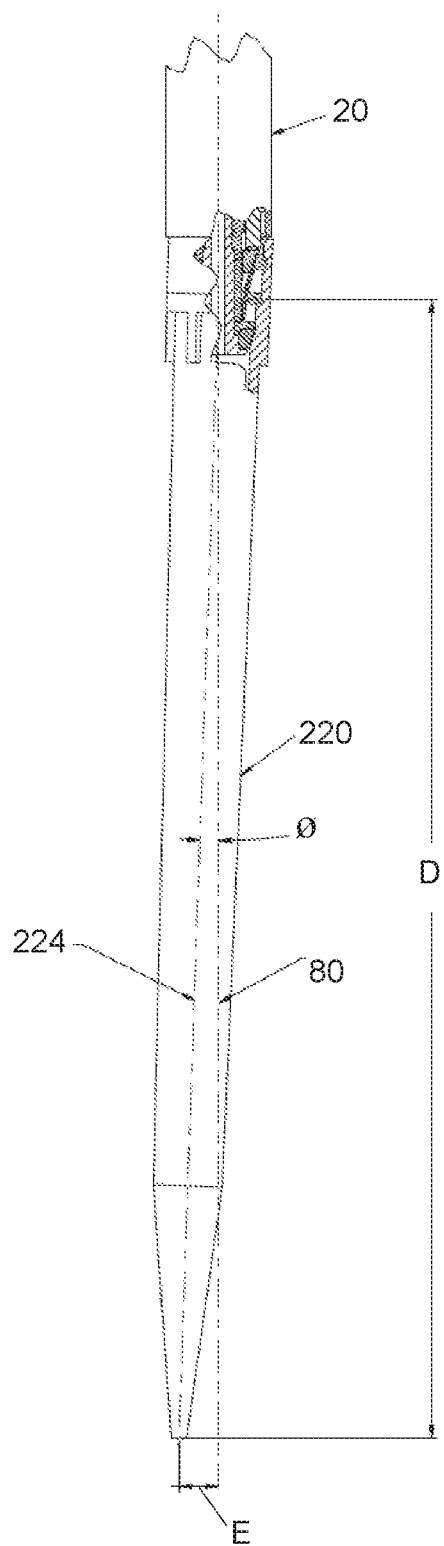
FIG. 36 is a fragmented and cutaway, longitudinal sectional, side elevational view of an embodiment of a pipette device operatively coupled to a misaligned coupling between example embodiments of an expanding mandrel collet coupling device and disposable pipette tip for defining misalignment parameters.

For example, and as illustrated in FIGS. 35 and 36, the relationship between the misalignment angle (Ø), the tip axial distance (D) and positional error (E) is: E=D*TAN (Ø). For example, with a misalignment angle (Ø) of two degrees and a tip axial distance of ninety millimeters, the positional error (E) is 3.14 millimeters. This is considered to be very high considering typical positional error tolerances are typically plus or minus 0.5 millimeters.

Figure 37:
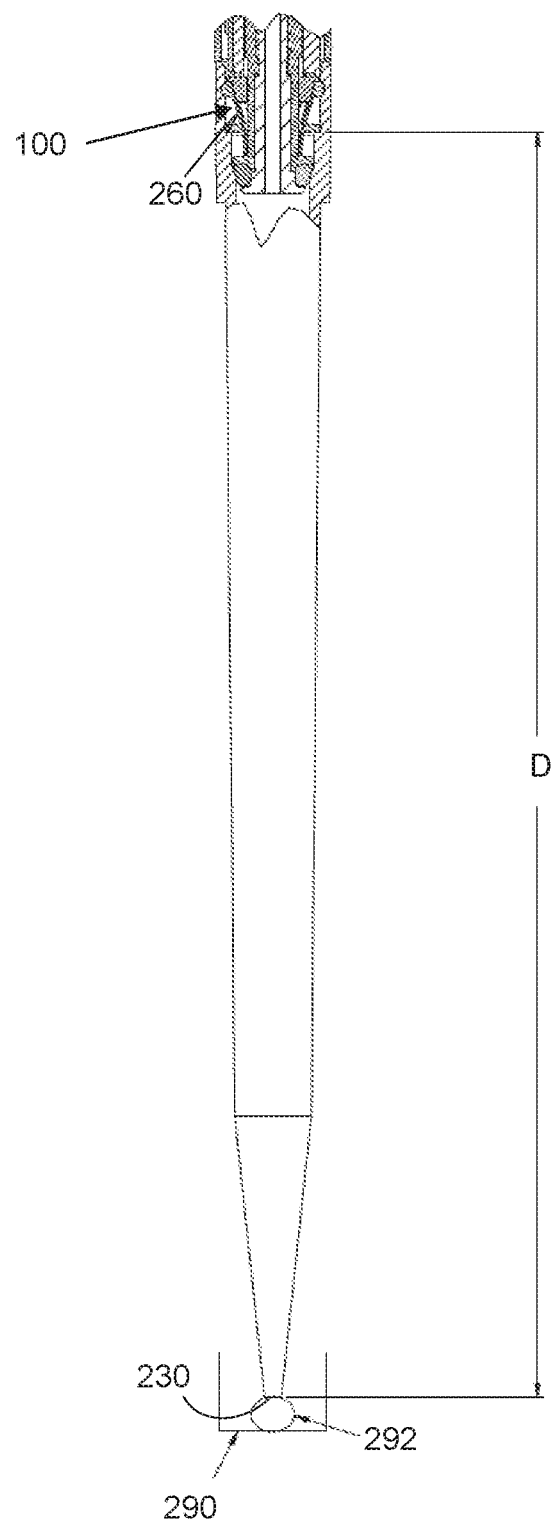
FIG. 37 is a fragmented and cutaway, longitudinal sectional, side elevational view of the example embodiments of the air displacement pipette device coupled to the expanding mandrel collet coupling device that is coupled to the disposable pipette tip that has a small liquid volume interposed between the end of the pipette tip and a working surface and the view further having dimensioning lines illustrated and identified.

FIG. 37 illustrates correct tip alignment with the axial shoulder surface 196 and the axial shoulder seat 260 in flush contact with one another to provide proper alignment and to maintain the tip axial distance D from the tip seat 260 to the distal end 230 constant to establish a known and controlled distance of the pipette tip end 230 along the vertical or axial axis Z and a perpendicular axis X. This is important to allow the pipette device to target small holes and small volumes of liquid. Additionally, smaller volumes of liquid can be transferred resulting from the known fixed distance of the pipette tip allowing for a controlled touch of the pipette tip/liquid to the working surface 290 onto or from which liquid 292 is to be transferred.

Dimensions and Relationships

Accordingly, for proper use and operation, dimensions between the coupler 100 and tip 220 are related accordingly.

Figure 38:
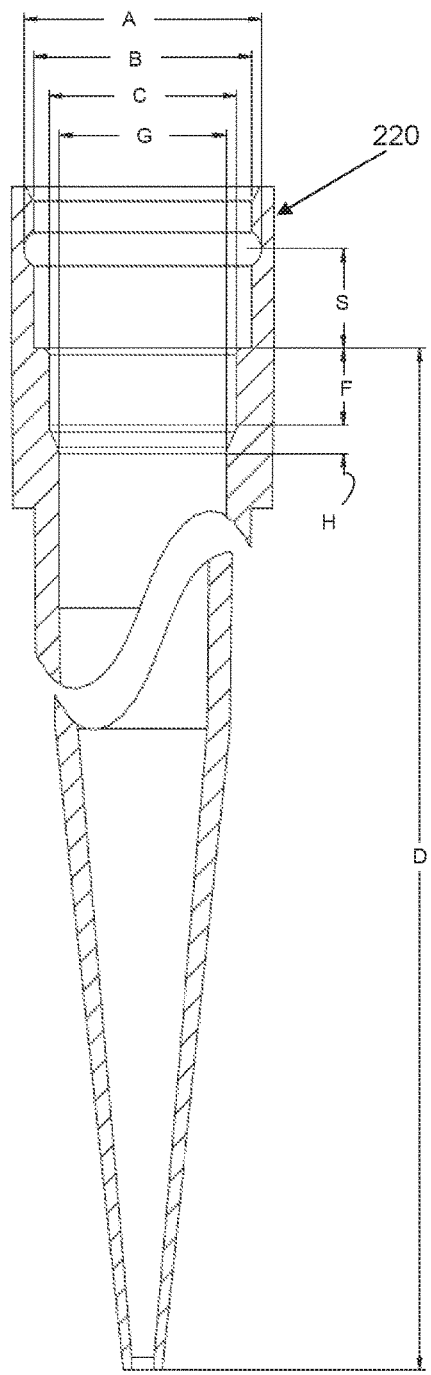
FIG. 38 is a fragmentary, longitudinal sectional, side elevational view detailing the interior of the example embodiment of the disposable pipette tip and the view further having dimensioning lines illustrated and identified.
Figure 39:
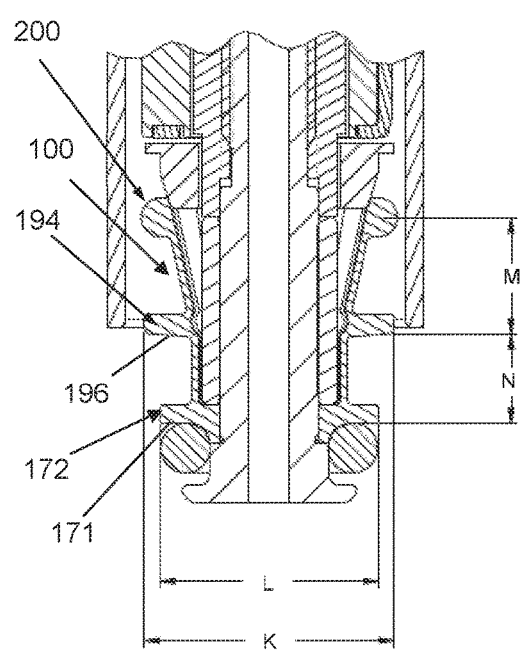
FIG. 39 is a fragmentary, longitudinal sectional, side elevational view of the example embodiment of the pipette device operatively coupled to the example embodiment of the expanding mandrel collet coupling device with dimensioning lines relative to the dimensioning lines in FIG. 38 illustrated and identified.

Referring to FIGS. 15, 38, and 39, the tip groove diameter A must be large enough to allow the segments 200 to pull the tip 220 up and adequately lock the tip 220 in place. Conversely, if it is too big, the segments 200 may not be able to be pushed in sufficiently to get a good lock. Additionally, internal diameters B and C must be larger than external diameter K of stop disc 194 and external diameter L of annular base 172, respectively. However, they must not be too much bigger, as this may result in a poor fit and/or misalignment.

Referring to FIGS. 38 and 39, the tip seat to groove dimension S must be matched to the stop disk seat surface 196 to segment 200 center dimension M. This relationship is critical to the coupling between the tip 220 and stop disc 194.

Referring to FIGS. 19, 38, and 39, the dimension of the tip seat surface 260 to the O-ring seal land 266 in FIG. 19, dimension F in FIG. 38, must match the stop disk surface 196 to the distally facing perpendicular lip surface 171, dimension N in FIG. 39. These dimensions control the amount that the distal O-ring 140 is compressed, and thus how well it seals. The tip surface 260 and stop disc seating/coupling surface 196 must be fully mated in order to provide proper alignment and maintain the tip axial distance D.

Referring to FIGS. 37 through 39, the dimension D between the tip seat 260 to the distal end 230 (or axial distance) along with the mating of the coupling seats establish a known and controlled distance of the pipette tip end. This is important to allow the pipette device to target small holes and small volumes of liquid. Additionally, smaller volumes of liquid can be transferred resulting from the known fixed distance of the pipette tip allowing for a controlled touch of the pipette tip/liquid to the working surface onto or from which liquid is to be transferred.

Referring to FIGS. 15, 38, and 39, the tip internal diameter G must be smaller than diameter L of base 172 in order to create a seat or land for the distal O-ring 140 to seal against. If diameter G is too large, then the distal O-ring may not seal well. If the diameter is too small, then the distal O-ring 140 may not fully compress and may prevent the stop disc 194 from seating, or may cause harm to the distal O-ring 140. Additionally, the ramp length H along with the diameter G control the seat or land that mates with the O-ring 140. These dimensions are critical in providing a good O-ring seal. If ramp length H is too long, then the O-ring may not seal well. If H is too short, then the O-ring may not fully compress and may prevent the stop disc 194 from seating, or may cause harm to the O-ring 140.

Liquid Level Detection (LLD) Circuit Contacts

Figure 40:
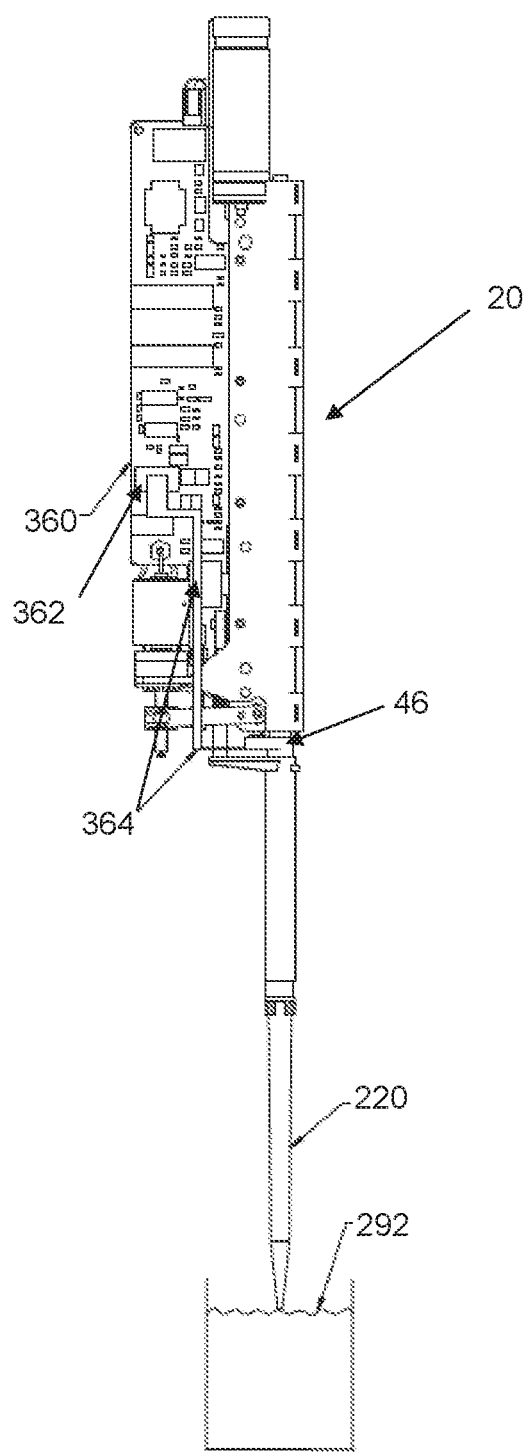
FIG. 40 is a longitudinal side elevational view of the pipette device assembly illustrating a circuit board that processes the signal from a Liquid Level Detection (LLD) circuit contact wherein the LLD circuit contact is connected between the circuit board and squeeze sleeve that is in contact with via an annular wedge the plurality of segments or elements coupling with the pipette tip wherein the distal end of the pipette tip is illustrated in contact with the liquid.

Referring to FIG. 40, and in one example embodiment, the pipette device assembly 10 further comprises a liquid level detection circuit assembly. The liquid level detection circuit assembly comprises a liquid level detection or LLD circuit board 360 comprising processing circuitry 362 electrically coupled to a LLD circuit contact 364 operatively coupled to the squeeze sleeve 46 that is made from an electrically non-conducting material so it is insulated from the rest of the assembly and wherein the contact 364 terminates to a circuit contact ring end 366 recessed in the bottom area of the squeeze sleeve 46 that is configured for selectively contacting the circuit contact ring end 366 with annular wedge 210 between the non-contact state illustrated in FIG. 22 and the contact state illustrated in FIG. 29 and therefore in contact with the plurality of conductive segments or elements coupling with the interior first working surface of a conductive tip 220.

As illustrated in FIG. 29, the LLD circuit contact 364 comprises the ring end 366 captured between the squeeze sleeve 46 and the annular wedge 210 wherein electrical closure or contact is made between the processing circuitry 362 of the LLD circuit board 360 (FIG. 40) and the annular wedge 210 which is made from electrically conductive material. The annular wedge 210 pushes and makes electrical contact with the plurality of radially outwardly projecting segments 200 which are made using an electrically conductive nonpliable material.

Accordingly, with the tip attached and the plurality of radially outwardly projecting segments 200 squeezed or pushed and locked into the tip groove 246 of the tip 220, the plurality of radially outwardly projecting segments 200 make electrical contact with the tip 220 which is also made from an electrically conductive material. As a result, and referring to FIG. 40, this completes the circuit between the processing circuitry 362 of the LLD circuit board 360 and the tip 220.

Additionally, the stop disk mounting post or distal mounting flange 36 is formed from a non-conducting material. Therefore, the body member 102 and the plurality of radially outwardly projecting segments 200 are insulated from the rest of the assembly.

Furthermore, the processing circuitry 362 of the LLD circuit board 360 detects a signal change when the tip 220 contacts liquid thereby having an ability to detect a surface of a liquid being transferred or a surface onto or from which liquid is being transferred. Again, actuation occurs when the coupling device 100 is attached to the tip 220 and the plurality of radially outwardly projecting segments 200 are radially pushed circumferentially and locked into the tip groove of the tip 220.

Alternative Example Embodiments

FIG. 41 illustrates the example embodiment of the expanding mandrel collet coupling device 100 positioned over the example embodiment of the disposable pipette tip 220 comprising an alternative sealing seat surface 2270 having an angle of substantially ninety degrees relative to the central longitudinal Z axis of the pipette tip 220.

Figures 42, 43:
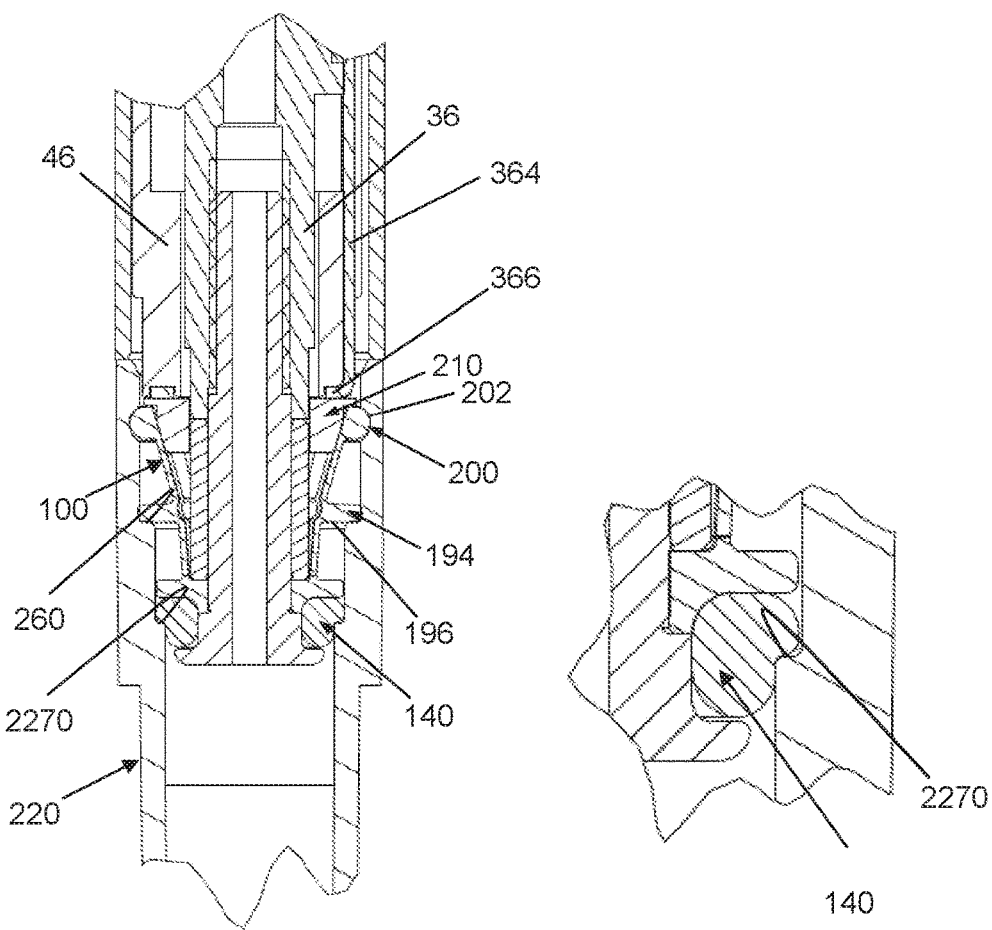
FIG. 42 is a fragmentary, longitudinal sectional, side elevational view of the example embodiment of the expanding mandrel collet coupling device positioned in the disposable pipette tip comprising the alternative sealing seat surface angle of substantially ninety degrees wherein the pipette tip is lifted up to its final seated state and the annular wedge moved into its final position for defining a final coupling state with the distal elastomeric element in a final compressed and seated sealing state against the alternative sealing seat surface angle of substantially ninety degrees.
FIG. 43 is a fragmentary, longitudinal sectional, side elevational detailed view of the distal elastomeric element in the final compressed state against the alternative sealing seat surface angle of substantially ninety degrees as is illustrated in FIG. 42.

FIG. 42 illustrates the example embodiment of the expanding mandrel collet coupling device 100 positioned in the disposable pipette tip comprising the alternative sealing seat surface 2270 wherein the tip 220 is lifted up to its final seated state and the annular wedge 210 moved into its final position for defining the final coupling state with the distal elastomeric element 140 in the final compressed and seated sealing state against the alternative sealing seat surface 2270.

FIG. 43 details the final compressed state of the distal elastomeric element 140 against the alternative sealing seat surface 2270.

Figure 44:
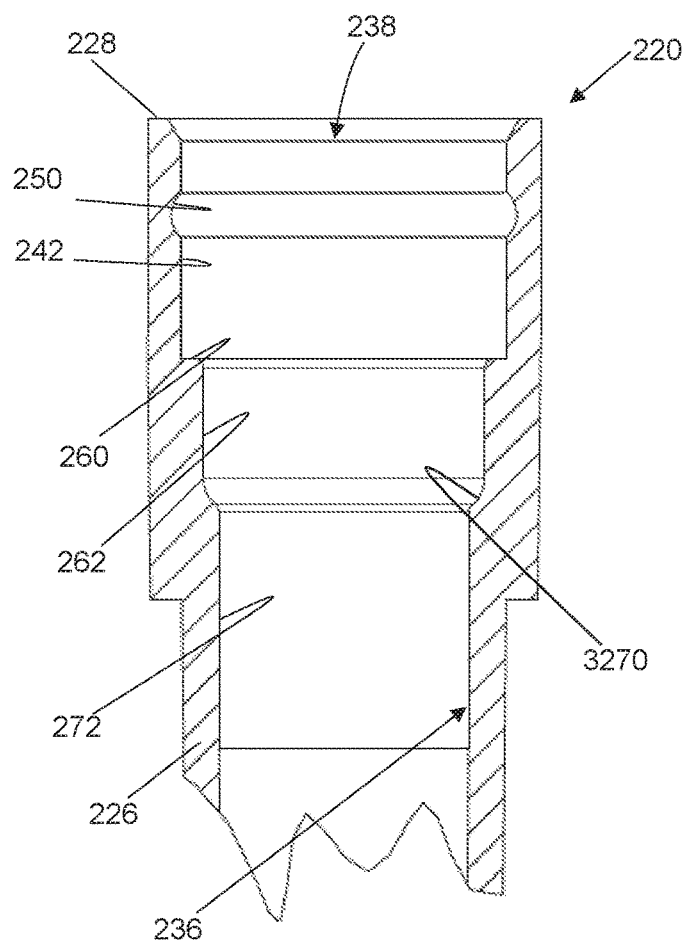
FIG. 44 is a fragmentary, longitudinal sectional, side elevational view of the example embodiment of the disposable pipette tip illustrating detail of the upper interior of the disposable pipette tip comprising another alternative sealing seat surface in the form of a circumferential radially concave sealing seat surface.
Figure 45:
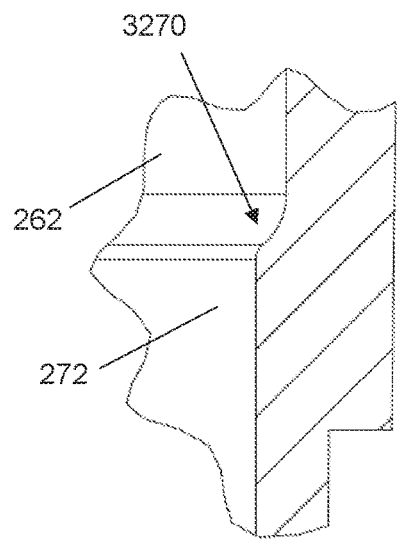
FIG. 45 is a fragmentary, longitudinal sectional, side elevational detailed view of the example embodiment of the disposable pipette tip illustrating detail of the circumferential radially concave sealing seat surface illustrated in FIG. 44.

FIG. 44 illustrates the upper interior of the disposable pipette tip 220 comprising another alternative sealing seat surface in the form of a circumferential radially concave sealing seat surface 3270. FIG. 45 details the circumferential radially concave sealing seat surface 3270 illustrated in FIG. 44.

Figure 46:
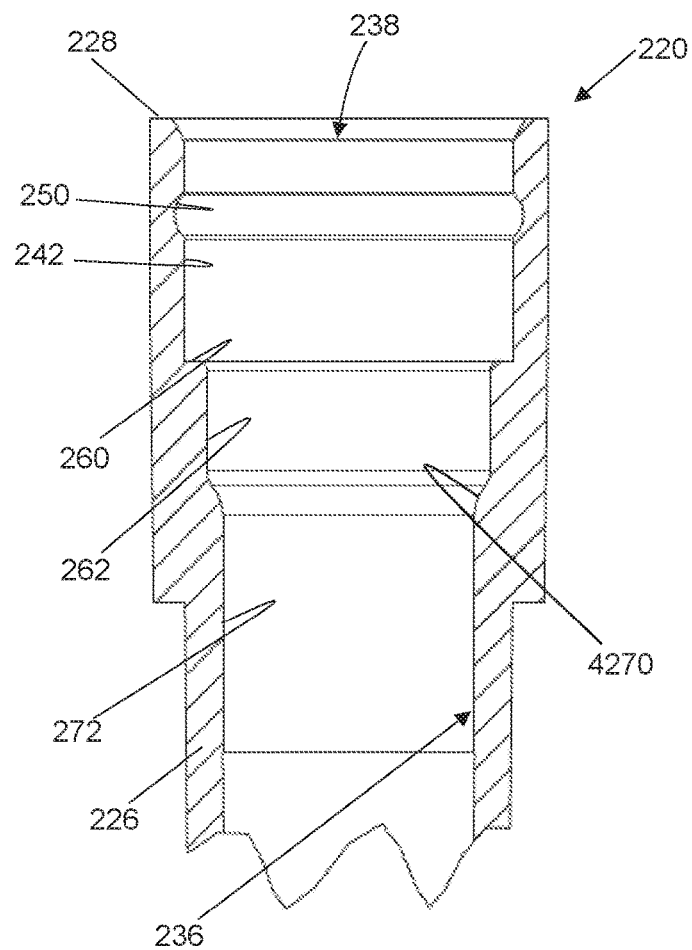
FIG. 46 is a fragmentary, longitudinal sectional, side elevational view of the example embodiment of the disposable pipette tip illustrating detail of a further alternative sealing seat surface in the form of a circumferential radially convex sealing seat surface.
Figure 47:
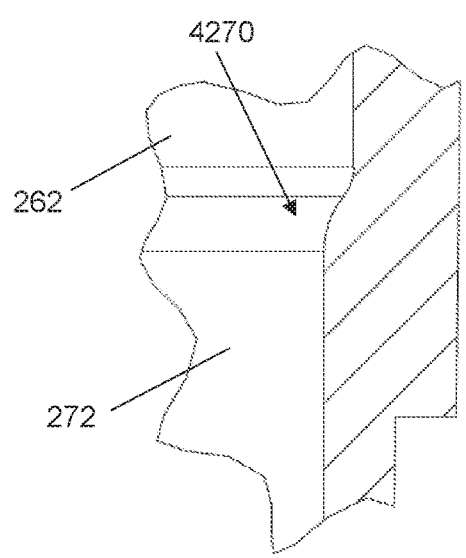
FIG. 47 is a fragmentary, longitudinal sectional, side elevational detailed view of the example embodiment of the disposable pipette tip illustrating detail of the circumferential radially convex sealing seat surface illustrated in FIG. 46.

FIG. 46 illustrates the example embodiment of the disposable pipette tip 220 illustrating detail of a further alternative sealing seat surface in the form of a circumferential radially convex sealing seat surface 4270. FIG. 47 details the circumferential radially convex sealing seat surface 4270 illustrated in FIG. 46.

Figure 48:
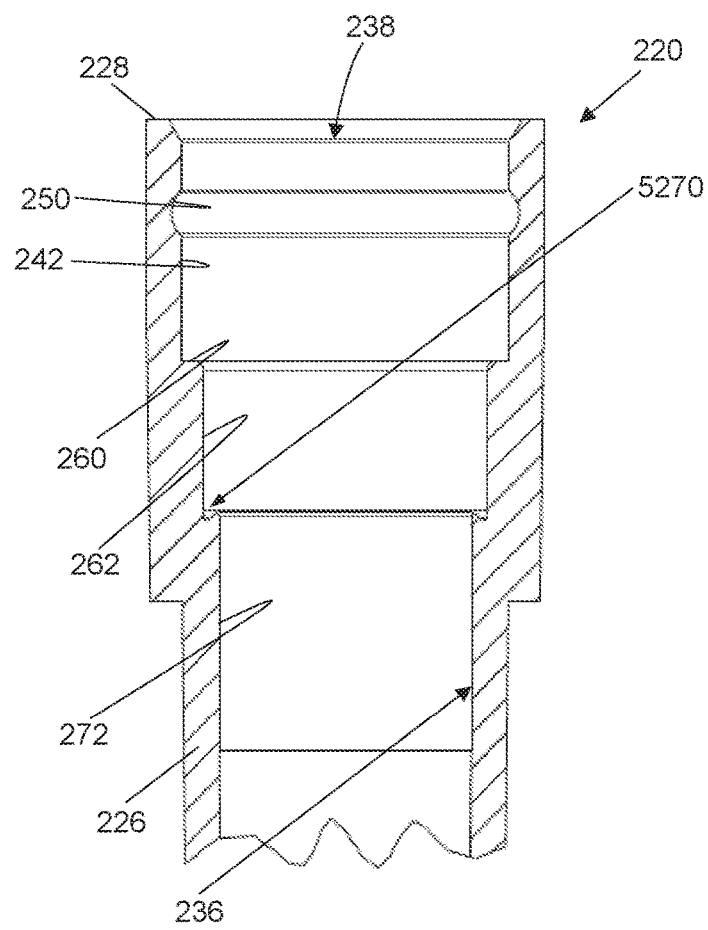
FIG. 48 is a fragmentary, longitudinal sectional, side elevational view of the example embodiment of the disposable pipette tip illustrating a yet further alternative sealing seat surface in the form of a circumferential upward facing tooth edge sealing seat surface.
Figure 49:
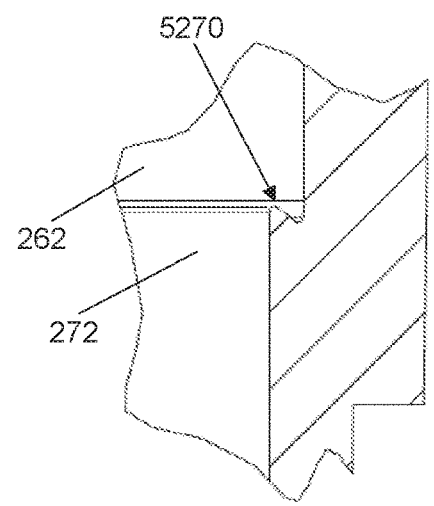
FIG. 49 is a fragmentary, longitudinal sectional, side elevational detailed view of the example embodiment of the disposable pipette tip illustrating detail of the circumferential upward facing tooth edge sealing seat surface illustrated in FIG. 48.

FIG. 48 illustrates the example embodiment of the disposable pipette tip 220 illustrating a yet further alternative sealing seat surface in the form of a circumferential upward facing tooth edge sealing seat surface 5270. FIG. 49 details the circumferential upward facing tooth edge sealing seat surface illustrated in FIG. 48.

Figure 50:
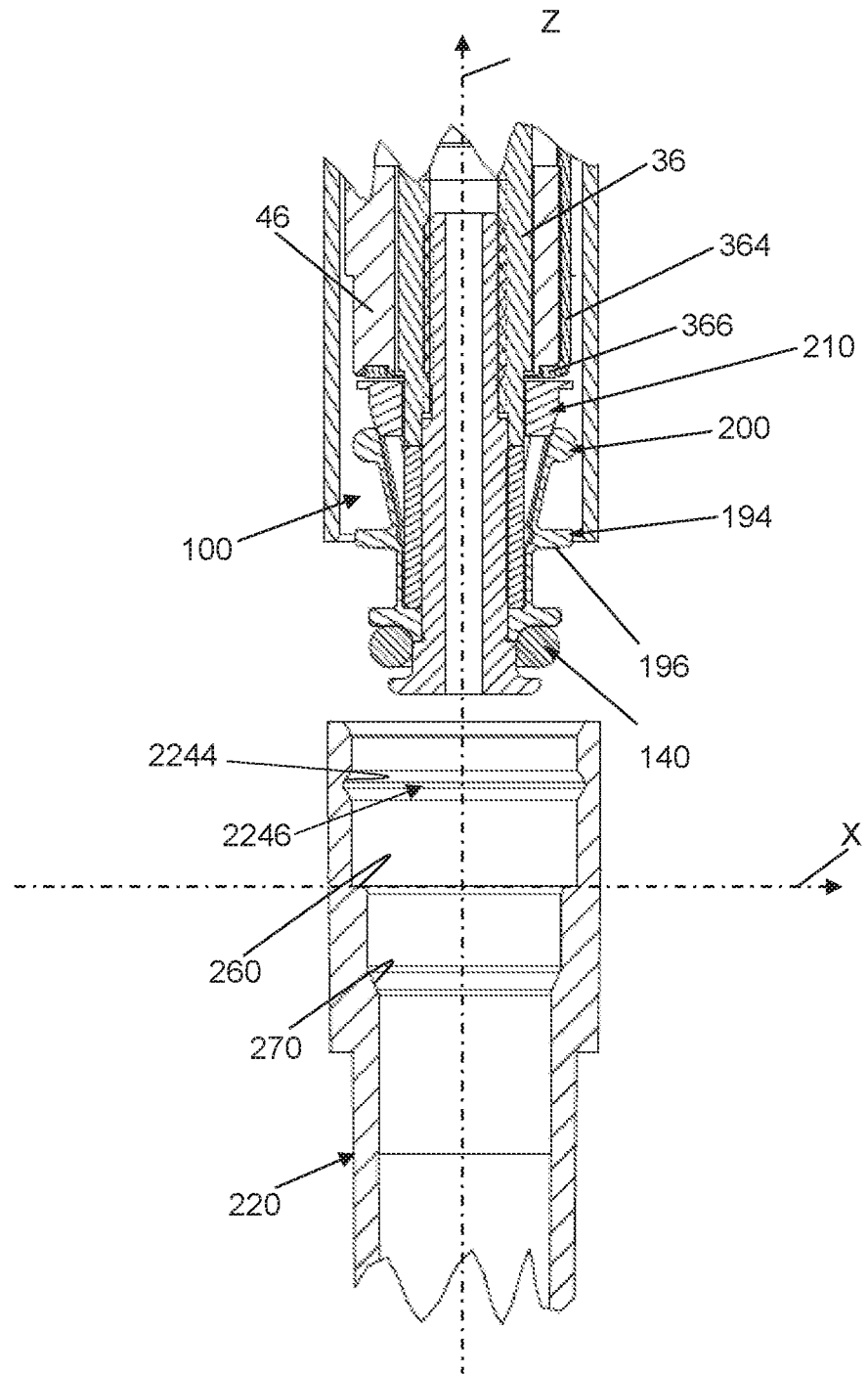
FIG. 50 is a fragmentary, longitudinal sectional, side elevational view of the example embodiment of the expanding mandrel collet coupling device positioned over the example embodiment of the disposable pipette tip comprising an alternative V-shaped groove defined by an V-shaped circumferential interior surface of the disposable pipette tip opening toward the longitudinal axis and having a V-shaped cross section as illustrated.

FIG. 50 is a fragmentary, longitudinal sectional, side elevational view of the example embodiment of the expanding mandrel collet coupling device 100 positioned over the example embodiment of the disposable pipette tip 220 comprising an alternative V-shaped groove 2246 defined by an V-shaped circumferential interior surface 2244 of the disposable pipette tip 220 opening toward the longitudinal Z axis and having a V-shaped cross section as illustrated.

Figures 51, 52:
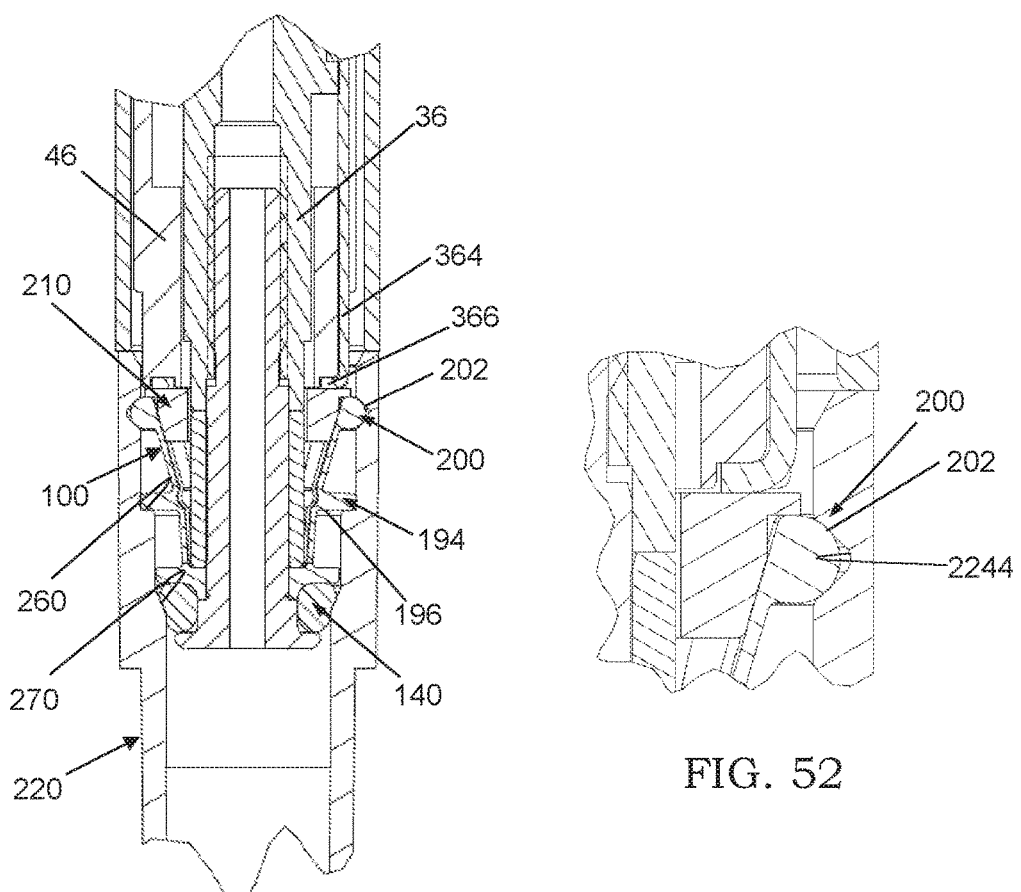
FIG. 51 is a fragmentary, longitudinal sectional, side elevational view of the example embodiment of the expanding mandrel collet coupling device positioned in the disposable pipette tip comprising the alternative V-shaped groove wherein the pipette tip is lifted up to its final state with the rounded surfaces of the plurality of expanding mandrel collet segments being extended into the V-shaped groove and into abutment against the V-shaped circumferential interior surface with the distal elastomeric element in a final compressed and seated sealing state against the sealing seat surface of the pipette tip.
FIG. 52 is a fragmentary, longitudinal sectional, side elevational detailed view of the rounded surface of one of the plurality of expanding mandrel collet segments being extended into the V-shaped groove and abutting against the V-shaped circumferential interior surface defining the V-shaped groove as is illustrated in FIG. 51.

FIG. 51 illustrates the expanding mandrel collet coupling device 100 being positioned in the disposable pipette tip 220 comprising the alternative V-shaped groove 2246 (FIG. 50) wherein the tip 220 is lifted up to its final state with the rounded surfaces 202 of the plurality of expanding mandrel collet segments 200 being extended into the V-shaped groove 2246 and into abutment against the V-shaped circumferential interior surface with the distal elastomeric element 140 in the final compressed and seated sealing state against the sealing seat surface 270 of the tip.

FIG. 52 illustrates the rounded surface 202 of one of the plurality of expanding mandrel collet segments 200 being extended into the V-shaped groove 2246 and abutting against the V-shaped circumferential interior surface 2244 defining the V-shaped groove 2246.

Figure 53:
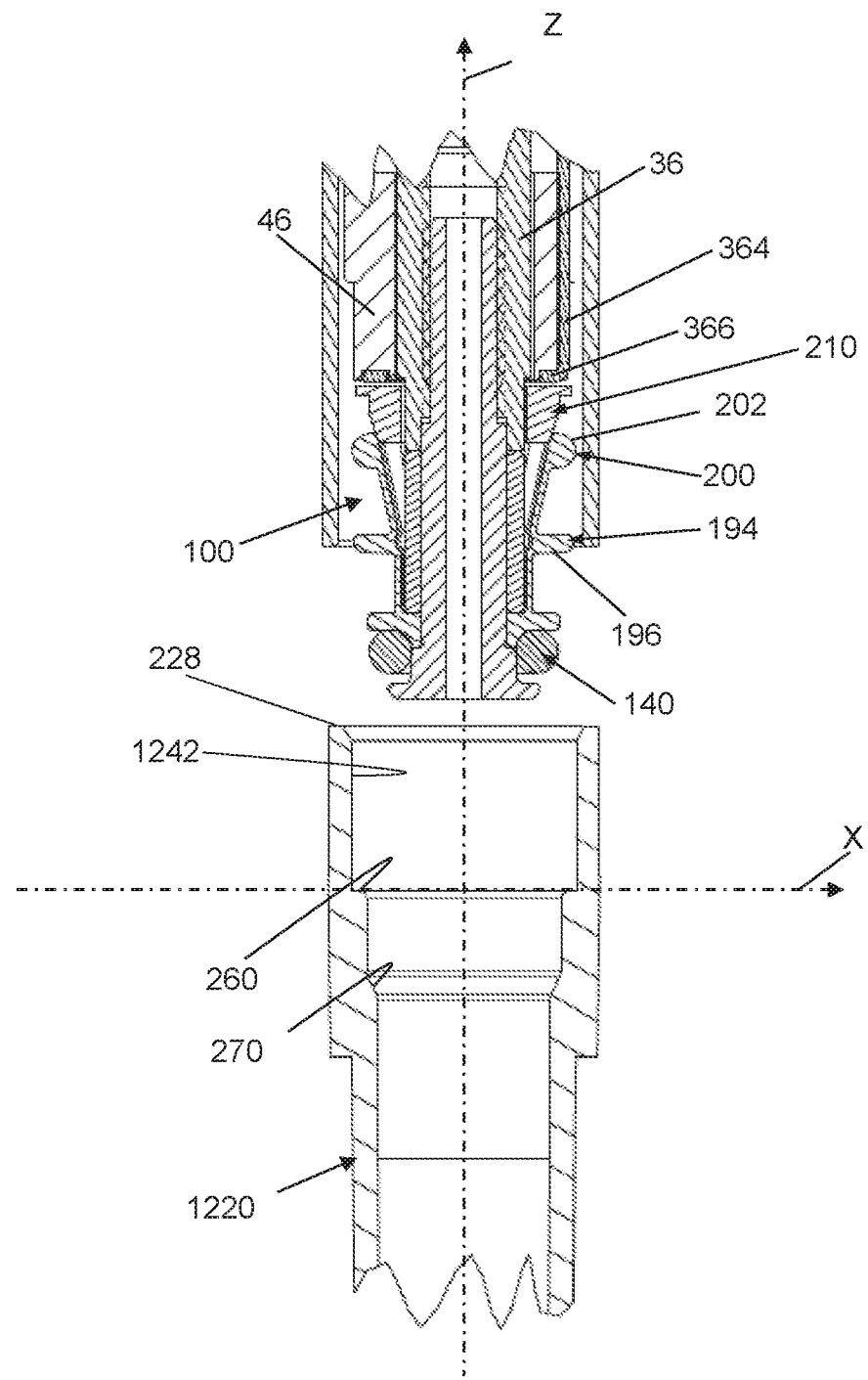
FIG. 53 is a fragmentary, longitudinal sectional, side elevational view of the example embodiment of the expanding mandrel collet coupling device positioned over a second example embodiment of the disposable pipette tip.

FIG. 53 illustrates the example embodiment of the expanding mandrel collet coupling device positioned over a second example embodiment of a disposable pipette tip 1220 devoid of arcuate circumferential interior surface 244 defining the circumferential annular groove 246.

Figure 54:
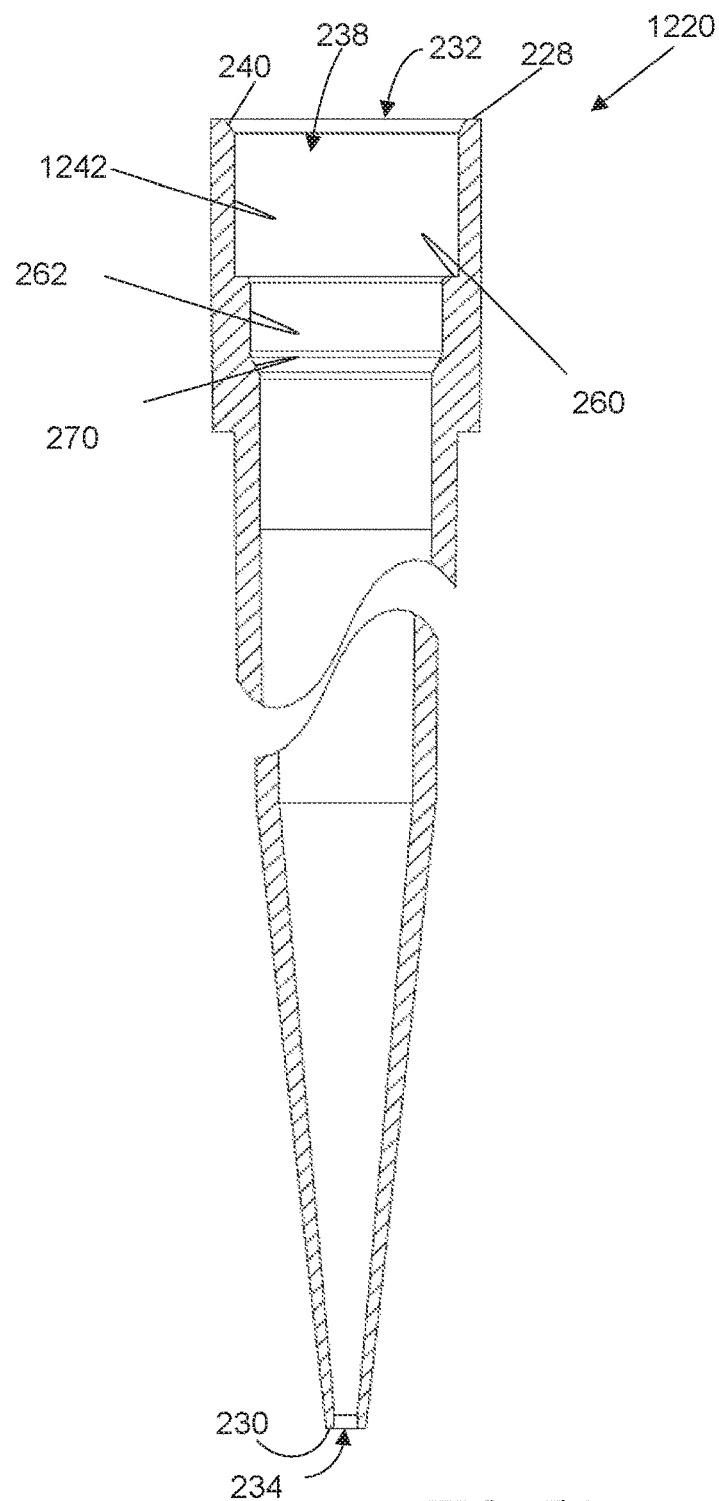
FIG. 54 is a fragmentary, longitudinal sectional, side elevational detailed view detailing the interior of the second example embodiment of the disposable pipette tip.

FIG. 54 details the interior of the second example embodiment of the disposable pipette tip 1220 which is analogous in all portions with the exception that interrupted interior surface section 242 of the first substantially cylindrical interior surface section 242 illustrated in FIG. 18 is devoid of interruption thereby defining uninterrupted interior surface section 1242 of the disposable pipette tip 1220 wherein the interior surface section 1242 defines the first working surface.

Figure 55:
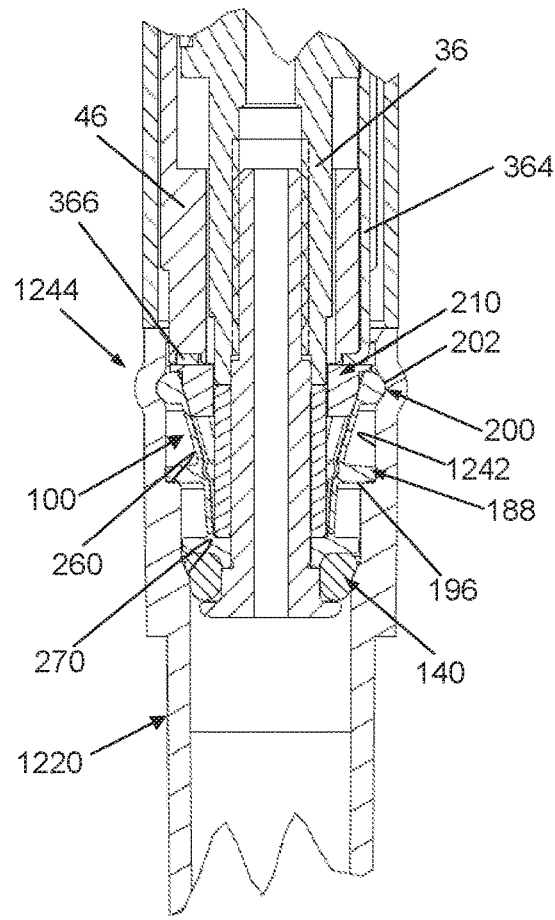
FIG. 55 is a fragmentary, longitudinal sectional, side elevational view of the example embodiment of the expanding mandrel collet coupling device positioned in the second example embodiment of the disposable pipette tip with a stop disk shoulder surface of the coupling device abutting against an axial stop surface of the second example embodiment of the disposable pipette tip and the rounded surfaces of the plurality of expanding mandrel collet segments being extended against an interior surface of a circumscribing sidewall of the second example embodiment of the disposable pipette tip resulting in a deformation of the interior surface and with the distal elastomeric element in a final compressed and seated sealing state against the sealing seat surface of the second example embodiment of the disposable pipette tip.

FIG. 55 illustrates the example embodiment of the expanding mandrel collet coupling device 100 positioned in the second example embodiment of the disposable pipette tip 1220 with the stop disk shoulder surface 196 of the coupling device 100 abutting against an axial stop surface 260 of the second example embodiment of the disposable pipette tip 1220 and the rounded surfaces 202 of the plurality of expanding mandrel collet segments 200 being extended against the interior surface 1242 of the circumscribing sidewall of the second example embodiment of the disposable pipette tip 1220 resulting in a deformation 1244 of the interior surface 1242 and with the distal elastomeric element 140 in the final compressed and seated sealing state against the sealing seat surface 270 of the second example embodiment of the disposable pipette tip 1220.

Figure 56:
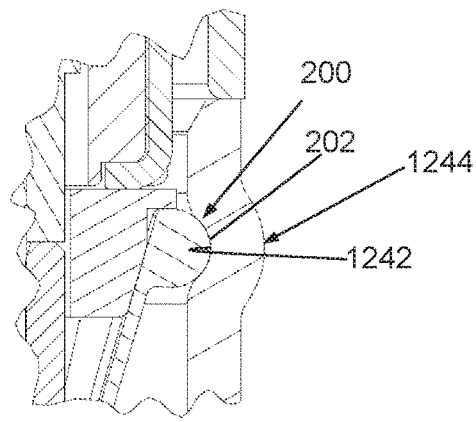
FIG. 56 is a fragmentary, longitudinal sectional, side elevational detailed view of the rounded surface of one of the plurality of expanding mandrel collet segments of the expanding mandrel collet coupling device being extended against and deforming the interior surface of the circumscribing sidewall of the second example embodiment of the disposable pipette tip as is illustrated in FIG. 55.
Figure 57:
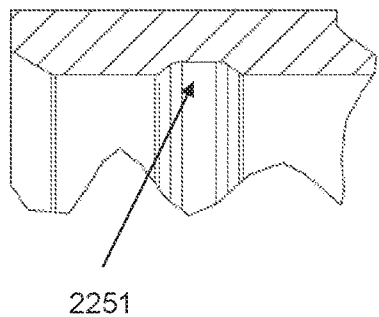
FIGS. 57 through 67 are fragmentary, longitudinal sectional, side elevational views of the example embodiment of the disposable pipette tip comprising alternative groove shape embodiments relative to the circumferential annular tip groove illustrated in at least FIG. 19.
Figure 58:
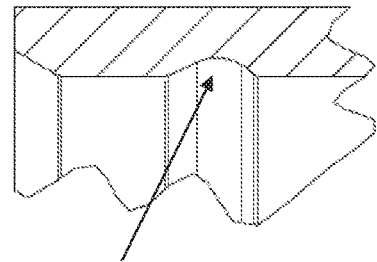
Figure 59:
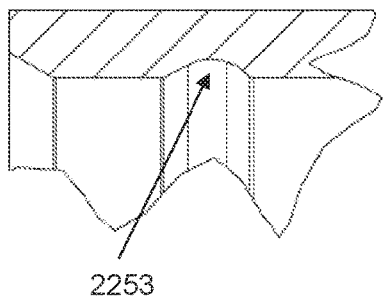
Figure 60:
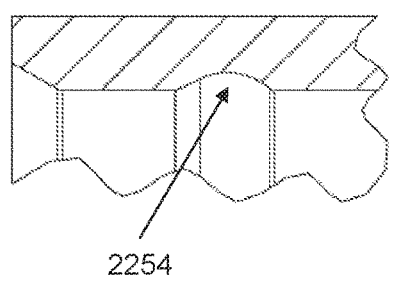
Figure 61:
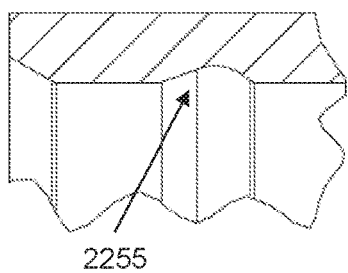
Figure 62:
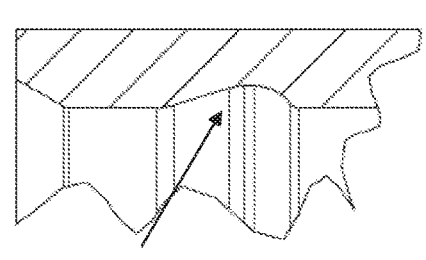
Figure 63:
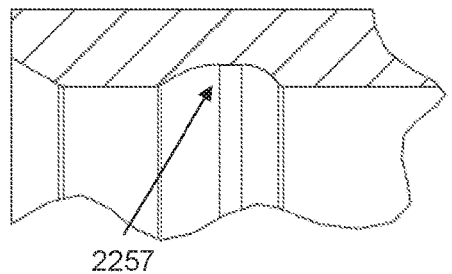
Figure 64:
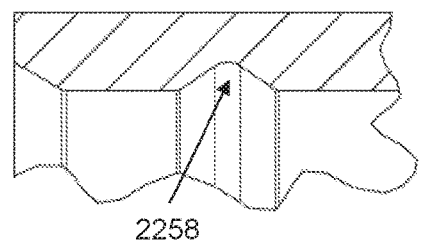
Figure 65:
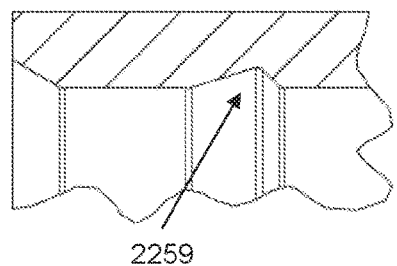
Figure 66:
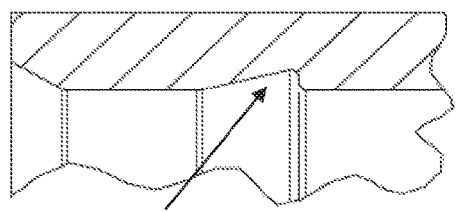
Figure 67:
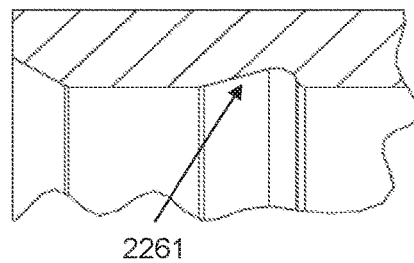

FIG. 56 details the rounded surface 202 of one of the plurality of expanding mandrel collet segments 200 of the expanding mandrel collet coupling device 100 being extended against and deforming 1244 the interior surface 1242 of the circumscribing sidewall of the second example embodiment of the disposable pipette tip as is illustrated in FIG. 55.

FIGS. 57 through 67 are fragmentary, longitudinal sectional, side elevational views of the example embodiment of the disposable pipette tip comprising alternative groove shape embodiments relative to the circumferential annular tip groove for segments 200 illustrated in at least FIG. 19 and the V-shaped groove segments 200 illustrated in at least FIG. 50.

In particular, FIGS. 57 through 67 illustrate respective alternative groove configurations 2251 through 2261 for receipt of segments 200.

Alternative Example Embodiment Collet 2170

Figure 68:
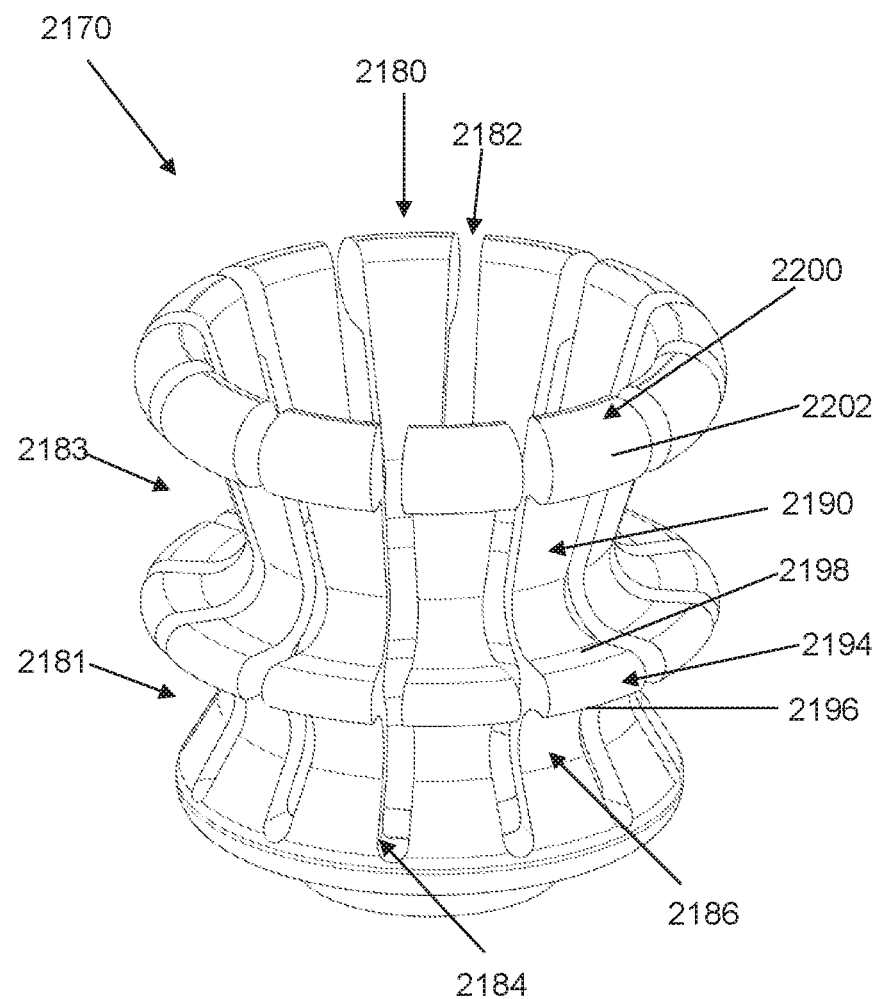
FIG. 68 is a top and side perspective view of a second or alternative example embodiment of an expanding mandrel collet of the expanding mandrel collet coupling device.

FIG. 68 illustrates a second or alternative example embodiment of an expanding mandrel collet 2170 which is configured as a direct alternative to the expanding mandrel collet 170 (FIG. 5) of the expanding mandrel collet coupling device 100 (FIG. 5). The expanding mandrel collet 2170 is analogous in function to collet 170, but configured to improve performance and longevity.

Figure 69:
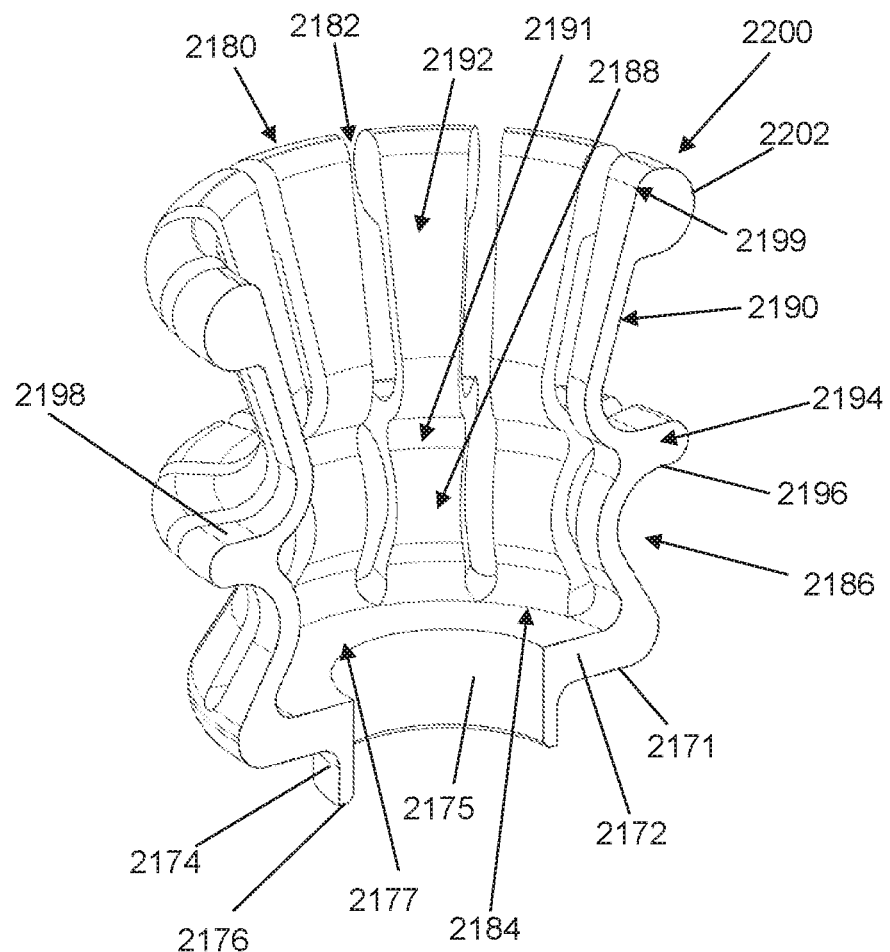
FIG. 69 is a longitudinal sectional, side perspective view of the second or alternative example embodiment of the expanding mandrel collet of the expanding mandrel collet coupling device.

Referring to FIGS. 68 and 69, the expanding mandrel collet 2170 comprises a plurality of circumferentially spaced apart upwardly extending collet arms 2180 that radially outwardly extend and arcuately transition upwardly from the lower annular base portion 2172 and terminating to free segmented ends 2200 defining the segmented collar disposed axially above the lower annular base portion 2172. The plurality of circumferentially spaced apart upwardly extending collet arms 2180 are separated from one another by one of a plurality of circumferentially spaced apart upwardly extending kerfs or slots 2182.

Referring to FIGS. 68 and 69, each of the plurality of upwardly extending collet arms 2180 comprises a respective lower arm portion 2186 transitioning into a respective upper arm portion 2190. In one embodiment, the plurality of circumferentially spaced apart lower arm portions 2186 form a circumscribing lower body portion 2181 and the plurality of circumferentially spaced apart upper arm portions 2190 form a frustoconically shaped circumscribing upper body portion 2183 radially outwardly and upwardly transitioning from the lower body portion 2181.

Referring to FIGS. 68 and 69, the distal or lower annular base portion 2172 comprises a distally or downwardly facing base surface 2171. The distally facing base surface 2171 downwardly transitions into an abbreviated distal or lower end annular stem surface 2174 that terminates to a distal or lower annular base portion end 2176 of the lower annular base portion 2172. The base surface 2171 and lower end annular stem surface 2174 define an abbreviated distal end annular groove.

As illustrated in FIG. 69, the lower annular base portion 2172 further comprises an inner cylindrical surface 2175 upwardly transitioning into the interior annular shoulder stop surface 2177.

As further illustrated in FIG. 69, the lower arm portions 2186 comprise the circumferentially spaced apart lower end portions 2184 that are attached to the lower annular base portion 2172. The lower arm portions 2186 further comprise upper end portions defining medial arm portions having interior annular recessed segmented surfaces or grooves 2191 and exterior radially outwardly extending annularly segmented stop disk portions 2194. The segmented stop disks 2194 circumscribe and radially extend from an exterior of the medial arm portions of the plurality of circumferentially spaced apart upwardly extending collet arms 2180 defining an annular segmented stop disk. Each of the segmented stop disks 2194 comprises a proximally or upwardly facing stop disk surface 2198 and a distally or downwardly facing stop disk surfaces 2196. Additionally, the plurality of lower arm portions 2186 comprise inner cylindrical or interior segmented surfaces 2188 dimensioned with an inner diameter that closely circumscribes the spacer 160 (FIG. 10) which circumscribes the elongated central body member 102 (FIG. 10).

Referring to FIGS. 68 and 69, the plurality of circumferentially spaced apart upper arm portions 2190 upwardly and radially outwardly transition from the respective lower arm portions 2186 and terminate into a plurality of free ends 2199 disposed above and radially outwardly from the lower arm portions 2186 wherein the plurality of free ends 2199 comprise radially outwardly projecting segments defining segmented collar 2200 wherein each segment comprises an exterior outwardly facing surface 2202 which, in one embodiment is outwardly rounded or arcuate in shape. Accordingly, the upper arm portions 2190 upwardly and radially outwardly transition from the segmented stop disks 2194 to a plurality of radially outwardly projecting segments defining segmented collar 2200. Additionally, the plurality of circumferentially spaced apart radially outwardly and upwardly extending upper arm portions 2190 including the segments respectively comprise interior surfaces 2192 forming an inclined segmented interior surface complemental to the proximally inclined annular side surface 216 (FIG. 13) of the annular wedge 210 (FIG. 13).

Comparing FIGS. 12 and 69, the expanding mandrel collet 2170 widens the base of each of the ends 2184 of each of the respective arms 2180 relative to the expanding mandrel collet 170 and radially extends the ends 2184 of arms 2180 outward in order to increase the radius of each of the arms 2180 relative to the expanding mandrel collet 170. Pushing the lower ends outward and increasing their diameter allows a larger chord segment or width at the bottom ends 2184 of each of extending arms 2180 wherein the increased width of each of extending arms 2180 improves the strength of each of extending arms 2180. Additionally, increasing radial extension at the lower ends 2184 of arms 2180 provides increased strength. The coupling function is unchanged.

From an engineering perspective, the extending arms 2180 can be modelled as a cantilever beam in bending. Classical strength of materials techniques can be used to evaluate material stress when the beam is subject to bending, as occurs when the coupler is engaged and disengaged. In addition, when bending is done repeatedly, or cyclically, the material stress can be analyzed with regard to fatigue strength to provide adequate product life. Increasing the width at the base of the beam, as well as increasing associated radii, are geometry modifications used to lower stress and improve strength.

Device Aspects

In one aspect, the pipette tip coupling device or expanding mandrel collet coupling device 100 provides improved life span.

In another aspect, the radially outwardly projecting segments 200 of the expanding mandrel collet 170 provide a more rigid coupling for providing a stiffer joint between the pipette tip 220 and coupler 100.

In another aspect, the radially outwardly projecting segments 200 of the expanding mandrel collet 170 pulls the tip 220 up and seats it efficiently.

In another aspect, the coupler 100 will not be affected by ejecting a tip in free air. O-ring coupling life is adversely affected when the tip is ejected in free air because the O-ring is scuffed and abraded by the groove in the tip as the tip is pushed off by the spring loaded eject sleeve. The hardness of the radially outwardly projecting segments 200 resists the harmful acts of this scuffing and abrasion.

In another aspect, the material of the expanding mandrel collet 170 can easily be made from conductive material in order to provide an electrical circuit to the tip for liquid level detection or other uses as detailed above.

In another aspect, the radially outwardly projecting segments 200 of the expanding mandrel collet 170 are formed from hard and durable materials such as, but not limited to, metallic or hard plastic to provide improved life and because the discrete elements or segments are much harder than the plastic tip, they work into the tip groove more efficiently than soft elastomeric material such as an O-ring.

In another aspect, the radially outwardly projecting segments 200 can be activated with a low squeeze/axial force because the mechanical design is efficient. A lower squeeze/axial force requirement improves the life on the associated parts providing the axial force. As a result of this lower squeeze/axial force requirement, the radially outwardly projecting segments 200 allows the lower or distal seal 140 to have improved life span because the elastomeric material in not compressed as much.

In another aspect, the coupler 100 allows the lower or distal seal 140 to be easily accessed if replacement is required. Also, the lower or distal seal 140 can be made from a greater variety of materials because it does not need to be conductive for the LLD circuit.

In another aspect, maintenance costs are lower because of the improved life and easier accessibility to the lower or distal seal.

In yet another aspect, tip alignment to the pipette device 20 is improved because of improved seating.

Method Aspects

In light of the above, and in a further aspect, an example embodiment of a method is provided for securing attachment of at least one pipette tip to at least one pipette tip coupler in the form of an expanding mandrel collet coupling device carried by a pipette device, the method comprising: (1) providing a pipette tip comprising a sidewall having an interior circumscribing surface defining a passage opening extending between an open distal end intended for immersion in a medium to be pipetted and an open proximal end opposite in an axial direction to the open distal end; (2) providing a pipette tip coupler comprising a distally facing axial stop shoulder surface formed by an axially stepped coupler shoulder of an exterior circumscribing surface of the pipette tip coupler, the distally facing axial stop shoulder surface complementary to a proximally facing axial stop surface formed by an axially stepped shoulder surface of the interior circumscribing surface of the sidewall of the pipette tip; (3) providing a plurality of discrete coupling elements or segments spaced apart and disposed circumferentially on said upper seating surface of said pipette tip coupler body; (4) providing a distal elastomeric element carried by the pipette tip coupler at a location inferior to the axially stepped coupler shoulder; (5) locating a distal end of the pipette tip coupler over the open proximal end of the pipette tip with an axial alignment between a central longitudinal axis of the pipette tip coupler and a central longitudinal axis of the pipette tip; (6) translating the distal end of the pipette tip coupler through the open proximal end of the pipette tip until the distal elastomeric element contacts a circumferential radially inwardly angled and distally extending interior working surface of the interior circumscribing surface of the sidewall of the pipette tip distal from the axially stepped shoulder of the interior circumscribing surface of the sidewall of the pipette tip; and (7) axially squeezing or pushing the plurality of discrete coupling elements or segments into a radially extended state of abutment with an upper axially arcuate circumferential surface sector portion of an axially arcuate circumferential interior surface defining a groove formed into the interior circumscribing surface of the sidewall of the pipette tip at a location superior to the axial stop surface of the pipette tip for providing a proximally directed radial and axial resultant pre-stress force to the pipette tip for energizing the distal elastomeric element into a compressed state configured for providing the axial and radial sealing abutment of the outer circumferential portion of the distal elastomeric element with the circumferential radially inwardly angled and distally extending interior working surface of the interior circumscribing surface of the sidewall of the pipette tip, and for abutting the proximally facing axial stop surface of the pipette tip with the distally facing axial stop surface of said pipette tip coupler body to define an axial coupling position of the pipette tip on the pipette tip coupler device.

In light of the present disclosure as set forth above, further structural modifications and adaptations may be resorted to without departing from the scope and fair meaning of the embodiments of the present disclosure as set forth above. For example, FIGS. 57 through 67 are fragmentary, longitudinal sectional, side elevational views detailing different alternative example embodiments to the circumferential annular tip groove 246 illustrated in at least in FIG. 19 and the V-shaped groove segments 200 illustrated in at least FIG. 50. In particular, FIGS. 57 through 67 illustrate respective alternative groove configurations 2251 through 2261 for receipt of segments 200. Additionally, the segments of the coupler may comprise radially outwardly faces complementary to the respective different alternative example embodiments of the respective groove configurations 2251 through 2261. Accordingly, the first working surface is in the form of, but not limited to, the respective groove configurations or the uninterrupted configuration illustrated in FIGS. 53-56 wherein the first substantially cylindrical interior surface section 242 is devoid of interruption thereby defining uninterrupted interior surface section 1242 of the disposable pipette tip 1220. Furthermore, the tip distal O-ring sealing seat 270 may have different geometries in the form of, but not limited to, flat conical, concave radius, convex radius, step, et cetera. Moreover, the distal O-ring may have alternate shapes than an O-ring and may be in the form of, but not limited to, configurations complementary to the tip distal O-ring sealing seat 270.

INDUSTRIAL APPLICABILITY

The above delineation of the systems, assemblies, devices, and methods including uses and operations, demonstrate the industrial applicability of embodiment(s) of the present disclosure.

Accordingly, it should be apparent that further numerous structural modifications and adaptations may be resorted to without departing from the scope and fair meaning of the embodiment(s) of the present disclosure as set forth hereinabove and as described hereinbelow by the claims. Hence, the spirit and scope of the appended claims should not be limited to the above delineated description of the embodiment(s) of the present disclosure. And, in the appended claims reference to an element in the singular is not intended to mean "one and only one" unless explicitly so stated, but rather "one or more." Moreover, it is not necessary for a device or method to address each and every problem sought to be solved by the present disclosure, for it to be encompassed by the present claims.

What is claimed is:

1. A pipette tip coupling device and pipette tip assembly comprising:
   a pipette tip comprising a circumscribing sidewall with an open interior passage including an interior surface and extending along a central longitudinal axis of the pipette tip between an open proximal end and an open distal end of the pipette tip;
   a pipette tip coupling device comprising:
   a central body terminating in a distal end, the central body comprising an interior circumscribing sidewall surface defining an open ended passageway extending through the central body;
   an elastomeric element circumscribing the central body adjacent to the distal end of the central body; and
   an expanding collet circumscribing the elongated central body comprising:
      an annular base, at least a portion of which is proximal to the elastomeric element; and
      a segmented collar comprising a plurality of circumferentially spaced apart arm segments with distal ends attached to the annular base and proximal free arm portions, wherein each circumferentially spaced apart arm segment comprises an outer surface and an inner surface,
   wherein an upper portion of each of the proximal free arm portions of the plurality of circumferentially spaced apart arm segments abuts against a first inner surface of the circumscribing sidewall of the pipette tip for securing the pipette tip to the pipette tip coupling device, and wherein the elastomeric element abuts against a second inner surface of the circumscribing sidewall of the pipette tip to form a seal between the pipette tip coupling device and the pipette tip.

2. The pipette tip coupling device and pipette tip assembly of claim 1 further comprising an annular wedge movably circumscribing the central body, the annular wedge comprising:
   a proximal wedge surface;
   a distal wedge surface, wherein a circumference of the proximal wedge surface is larger than a circumference of the distal wedge surface;
   an exterior surface, wherein the exterior surface connects the proximal wedge surface with the distal wedge surface; and
   wherein the exterior surface of the annular wedge abuts against the inner surface of each of the proximal free arm portions of the plurality of the circumferentially spaced apart arm segments.

3. The pipette tip coupling device and pipette tip assembly of claim 2 wherein the segmented collar, the annular wedge, and the pipette tip are made from an electrically conductive material.

4. The pipette tip coupling device and pipette tip assembly of claim 1 wherein the pipette tip further comprises:
   a first section comprising a substantially cylindrical surface formed in the interior surface of the circumscribing sidewall distal to the open proximal end, the first section having a first diameter;
   a second section comprising a substantially cylindrical surface formed in the interior surface of the circumscribing sidewall distal to the first section, the second section having a second diameter smaller than the first diameter;
   a stop shoulder surface formed in the interior surface of the circumscribing sidewall at an interface of the first section and the second section;
   a third section comprising a substantially cylindrical surface formed in the interior surface of the circumscribing sidewall distal to the second section, the third section having a third diameter smaller than the second diameter;
   a sealing seat surface formed in the interior surface of the circumscribing sidewall at an interface of the second section and the third section; and
   at least one frustoconical section formed in the interior surface of the circumscribing sidewall between the third section and the distal open lower end
   wherein an upper portion of each of the proximal free arm portions of the plurality of circumferentially spaced apart arm segments abuts against the first section of the pipette tip for securing the pipette tip to the pipette tip coupling device, and wherein the elastomeric element abuts against the sealing seat surface of the pipette tip to form a seal between the pipette tip coupling device and the pipette tip.

5. The pipette tip coupling device and pipette tip assembly of claim 4 further comprising an annular wedge movably circumscribing the central body, the annular wedge comprising:
   a proximal wedge surface;
   a distal wedge surface, wherein a circumference of the proximal wedge surface is larger than a circumference of the distal wedge surface;
   an exterior surface, wherein the exterior surface connects the proximal wedge surface with the distal wedge surface; and
   wherein the exterior surface of the annular wedge abuts against the inner surface of each of the proximal free arm portions of the plurality of the circumferentially spaced apart arm segments.

6. The pipette tip coupling device and pipette tip assembly of claim 5 wherein the segmented collar, the annular wedge, and the pipette tip are made from an electrically conductive material.

7. The pipette tip coupling device and pipette tip assembly of claim 1 wherein the pipette tip further comprises:
   a first section formed in the interior surface of the circumscribing sidewall distal to the open proximal end comprising:
      a substantially cylindrical upper first portion having a first diameter;
      a substantially cylindrical lower first portion having the first diameter; and
      an annular groove interposed between the substantially cylindrical upper first portion and the substantially cylindrical lower first portion;
   a second section comprising a substantially cylindrical surface formed in the interior surface of the circumscribing sidewall distal to the first section, the second section having a second diameter smaller than the first diameter;
   a stop shoulder surface formed in the interior surface of the circumscribing sidewall at an interface of the first section and the second section;
   a third section comprising a substantially cylindrical surface formed in the interior surface of the circumscribing sidewall distal to the second section, the third section having a third diameter smaller than the second diameter;
   a sealing seat surface formed in the interior surface of the circumscribing sidewall at an interface of the second section and the third section; and
   at least one frustoconical section formed in the interior surface of the circumscribing sidewall between the third section and the distal open lower end;
   wherein an upper portion of each of the proximal free arm portions of the plurality of circumferentially spaced apart arm segments abuts against the annular groove in the first section, and wherein the elastomeric element abuts against the sealing seat surface of the pipette tip to form a seal between the pipette tip coupling device and the pipette tip.

8. The pipette tip coupling device and pipette tip assembly of claim 7, the pipette tip further comprising an annular chamfered interior surface formed in the interior surface of the circumscribing sidewall extending radially inward from the open proximal end and terminating at a proximal end of the first section.

9. The pipette tip coupling device and pipette tip of claim 7 further comprising an annular wedge movably circumscribing the central body, the annular wedge comprising:
   a proximal wedge surface;
   a distal wedge surface, wherein a circumference of the proximal wedge surface is larger than a circumference of the distal wedge surface;
   an exterior surface, wherein the exterior surface connects the proximal wedge surface with the distal wedge surface; and
   wherein the exterior surface of the annular wedge abuts against the inner surface of each of the proximal free arm portions of the plurality of the circumferentially spaced apart arm segments.

10. The pipette tip coupling device and pipette tip assembly of claim 9 wherein the segmented collar, the annular wedge, and the pipette tip are each made from an electrically conductive material.

11. The pipette tip coupling device and pipette tip assembly of claim 7, the pipette tip further comprising:
   wherein the stop shoulder surface is an annular, substantially planar surface substantially perpendicular to the central longitudinal axis of the pipette tip; and
   wherein the sealing seat surface is an annular, substantially planar surface substantially perpendicular to the central longitudinal axis of the pipette tip.

12. The pipette tip coupling device and pipette tip assembly of claim 7, the pipette tip further comprising:
   wherein the stop shoulder surface is an annular, substantially planar surface substantially perpendicular to the central longitudinal axis of the pipette tip; and
   wherein the sealing seat surface is a frustoconical annular surface further comprising:
      an upper annular sealing seat surface edge at an intersection of the second section and the sealing seat surface;
      a lower annular sealing seat surface edge at an interface of the sealing seat surface and the third section; and
      wherein the upper annular sealing seat surface edge is greater in diameter than the lower annular sealing seat surface edge.

13. A pipette tip coupling device and pipette tip assembly comprising:
   a pipette tip comprising a circumscribing sidewall with an open interior passage including an interior surface and extending along a central longitudinal axis of the pipette tip between an open proximal end and an open distal end of the pipette tip;
   a pipette tip coupling device comprising:
      a central body terminating in a distal end, the central body comprising an interior circumscribing sidewall surface defining an open ended passageway extending through the central body;
      an elastomeric element circumscribing the central body adjacent to the distal end of the central body; and
      an expanding collet circumscribing the central body comprising:
         an annular base, at least a portion of which is proximal to the elastomeric element, the annular base comprising:
            a proximal annular disk; and
            a distal reduced diameter annular stem; and
         a segmented collar comprising a plurality of circumferentially spaced apart arm segments, each of the circumferentially spaced apart arm segments comprising:
            an outer surface;
            an inner surface
            a proximal free arm portion; and
            a distal arm end, wherein the distal arm ends are attached to the proximal annular disk and the proximal free arm portions extend above the annular base;
      wherein an upper portion of each of the proximal free arm portions of the plurality of circumferentially spaced apart arm segments abuts against a first inner surface of the circumscribing sidewall of the pipette tip for securing the pipette tip to the pipette tip coupling device, and wherein the elastomeric element abuts against a second inner surface of the circumscribing sidewall of the pipette tip to form a seal between the pipette tip coupling device and the pipette tip.

14. The pipette tip coupling device and pipette tip assembly of claim 13 further comprising an annular wedge movably circumscribing the central body, the annular wedge comprising:
a proximal wedge surface;
a distal wedge surface, wherein a circumference of the proximal wedge surface is larger than a circumference of the distal wedge surface;
an exterior surface, wherein the exterior surface connects the proximal wedge surface with the distal wedge surface; and
wherein the exterior surface of the annular wedge abuts against the inner surface of each of the proximal free arm portions of the plurality of the circumferentially spaced apart arm segments.

15. The pipette tip coupling device and pipette tip assembly of claim 13 wherein the segmented collar is capable of radially expanding between a first circumference and a second circumference greater than the first circumference.

16. The pipette tip coupling device and pipette tip assembly of claim 13 wherein each of the plurality of the outer surfaces of the circumferentially spaced apart arm segments further comprises a radially outwardly extending stop disk segment, and wherein the radially outwardly extending stop disk segments form a segmented stop disk.

17. The pipette tip coupling device and pipette tip assembly of claim 14 wherein the segmented collar, the annular wedge, and the pipette tip are made from an electrically conductive material.

18. A pipette tip coupling device and pipette tip assembly comprising:
a pipette tip comprising:
a circumscribing sidewall with an open interior passage including an interior surface and extending along a central longitudinal axis of the pipette tip between an open proximal end and an open distal end of the pipette tip;
a first section comprising a substantially cylindrical surface formed in the interior surface of the circumscribing sidewall distal to the open proximal end, the first section having a first diameter;
a second section comprising a substantially cylindrical surface formed in the interior surface of the circumscribing sidewall distal to the first section, the second section having a second diameter smaller than the first diameter;
a stop shoulder surface formed in the interior surface of the circumscribing sidewall at an interface of the first section and the second section;
a third section comprising a substantially cylindrical surface formed in the interior surface of the circumscribing sidewall distal to the second section, the third section having a third diameter smaller than the second diameter;
a sealing seat surface formed in the interior surface of the circumscribing sidewall at an interface of the second section and the third section; and
at least one frustoconical section formed in the interior surface of the circumscribing sidewall between the third section and the distal open lower end;
a pipette tip coupling device comprising:
a central body terminating in a distal end, the central body comprising an interior circumscribing sidewall surface defining an open ended passageway extending through the central body;
an elastomeric element circumscribing the central body adjacent to the distal end of the central body; and
an expanding collet circumscribing the central body comprising:
an annular base, at least a portion of which is proximal to the elastomeric element, the annular base comprising:
a proximal annular disk; and
a distal reduced diameter annular stem; and
a segmented collar comprising a plurality of circumferentially spaced apart arm segments, each of the circumferentially spaced apart arm segments comprising:
an outer surface;
an inner surface;
a proximal free arm portion; and
a distal arm end, wherein the distal arm ends are attached to the proximal annular disk and the proximal free arm portions extend above the annular base;
wherein an upper portion of each of the proximal free arm portions of the plurality of circumferentially spaced apart arm segments abuts against the first section of the pipette tip for securing the pipette tip to the pipette tip coupling device, and wherein the elastomeric element abuts against the sealing seat surface of the pipette tip to form a seal between the pipette tip coupling device and the pipette tip.

19. The pipette tip coupling device and pipette tip assembly of claim 18 wherein the stop shoulder surface is an annular, substantially planar surface substantially perpendicular to the central longitudinal axis of the pipette tip.

20. The pipette tip coupling device and pipette tip assembly of claim 18 wherein the sealing seat surface is an annular, substantially planar surface substantially perpendicular to the central longitudinal axis of the pipette tip.

21. The pipette tip coupling device and pipette tip assembly of claim 18 wherein the sealing seat surface is a frustoconical annular surface further comprising:
an upper annular sealing seat surface edge at an intersection of the second section and the sealing seat surface; and
a lower annular sealing seat surface edge at an interface of the sealing seat surface and the third section, wherein the upper annular sealing seat surface edge is greater in diameter than the lower annular sealing seat surface edge.

22. The pipette tip coupling device and pipette tip assembly of claim 18 further comprising an annular chamfered interior surface formed in the interior surface of the circumscribing sidewall of the pipette tip extending radially inward from the open proximal end and terminating at the proximal end of the first section.

23. The pipette tip coupling device and pipette tip assembly of claim 18 wherein the at least one frustoconical section further comprises:
a fourth section formed in the interior surface of the circumscribing sidewall distal to the third section; and
a fifth section formed in the interior surface of the circumscribing sidewall distal to the fourth section and proximal to the distal open end, wherein the fifth section has a greater taper than the fourth section.

24. A pipette tip coupling device and pipette tip assembly comprising:

a pipette tip comprising a circumscribing sidewall with an open interior passage including an interior surface and extending along a central longitudinal axis of the pipette tip between an open proximal end and an open distal end of the pipette tip;
a pipette tip coupling device comprising:
  a central body comprising:
    a proximal shank including a proximal end face;
    a distal stem portion;
    an end plate distal to the distal stem portion, the end plate having a diameter greater than a diameter of the distal stem portion; and
    an open-ended interior circumscribing surface forming an open passageway extending longitudinally from the proximal end face through the distal end plate;
  a distal elastomeric element, the distal elastomeric element disposed around the distal stem portion and adjacent to the distal end plate;
  an expanding collet disposed around the central body, the expanding collet comprising:
  an annular base comprising:
    a proximal disk portion; and
    a distal collet stem end portion;
  a plurality of circumferentially spaced apart, flexible, upwardly extending arms, each circumferentially spaced apart, flexible, upwardly extending arm comprising:
    a distal end attached to the disk portion;
    a proximal free arm portion; and
    an outer surface including a radially outwardly extending stop disk segment; and
  wherein the proximal free arm portions of the plurality of circumferentially spaced apart, flexible, upwardly extending arms are capable of expanding radially relative to the central body between an unexpanded state with a first circumference and an expanded state with a second circumference that is larger than the first circumference; and
  wherein an upper portion of each of the proximal free arm portions of the plurality of circumferentially spaced apart, flexible, upwardly extending arms abuts against a first inner surface of the circumscribing sidewall of the pipette tip for securing the pipette tip to the pipette tip coupling device, and wherein the elastomeric element abuts against a second inner surface of the circumscribing sidewall of the pipette tip to form a seal between the pipette tip coupling device and the pipette tip.

25. The pipette tip coupling device and pipette tip assembly of claim 24,
  wherein the distal stem portion comprises a proximal stem stop shoulder surface having a diameter greater than a diameter of the proximal shank; and
  wherein the distal collet stem end portion abuts against the proximal stem stop shoulder surface for securing the collet coaxially with the central body along the longitudinal central axis.

26. The pipette tip coupling device and pipette tip assembly of claim 24, wherein a circumference of the distal elastomeric element is greater than a circumference of the end plate of the central body.

27. The pipette tip coupling device and pipette tip assembly of claim 24,
  wherein the distal elastomeric element comprises a proximal surface and an interior surface; and
  wherein the expanding collet abuts against the proximal surface and the interior surface of the distal elastomeric element.

28. The pipette tip coupling device and pipette tip assembly of claim 24, further comprising an annular wedge movably circumscribing the central body, the annular wedge comprising:
  a proximal wedge surface;
  a distal wedge surface, wherein a circumference of the proximal wedge surface is larger than a circumference of the distal wedge surface;
  an exterior surface, wherein the exterior surface connects the proximal wedge surface with the distal wedge surface; and
  wherein the exterior surface of the annular wedge abuts against the inner surface of each of the proximal free arm portions of the plurality of circumferentially spaced apart, flexible, upwardly extending arms.

29. The pipette tip coupling device and pipette tip assembly of claim 24, further comprising a substantially cylindrical spacer circumscribing the central body.

30. The pipette tip coupling device and pipette tip assembly of claim 28, wherein the expanding collet and the annular wedge are made from an electrically conductive material.

* * * * *